United States Patent
Taylor et al.

(10) Patent No.: US 12,290,506 B2
(45) Date of Patent: May 6, 2025

(54) COMPOSITIONS AND FORMULATIONS FOR USE OF A PK INHIBITOR FOR THE PREVENTION, TREATMENT, AND IMPROVEMENT OF SKIN DISEASES, CONDITIONS, AND DISORDERS

(71) Applicant: DermBiont, Inc., Boston, MA (US)

(72) Inventors: Emma Taylor, San Francisco, CA (US); Karl Beutner, Fairfield, CA (US); Christopher Phillips, Doylestown, PA (US); Mark De Souza, Berkeley, CA (US); Ravi Kumar Pandrapragada, Clarksburg, MD (US); Vanessa Alexandra Cofré Urrutia, Santiago (CL); Brendan Philip Brady, Guildford (GB); Charles Rodney Greenaway Evans, Godalming (GB)

(73) Assignee: DermBiont, Inc., Boston, MA (US)

( * ) Notice: Subject to any disclaimer, the term of this patent is extended or adjusted under 35 U.S.C. 154(b) by 0 days.

(21) Appl. No.: 18/623,901

(22) Filed: Apr. 1, 2024

(65) Prior Publication Data

US 2024/0293368 A1    Sep. 5, 2024

Related U.S. Application Data

(63) Continuation of application No. PCT/US2023/023014, filed on May 19, 2023.

(60) Provisional application No. 63/489,697, filed on Mar. 10, 2023, provisional application No. 63/399,946, filed on Aug. 22, 2022, provisional application No. 63/344,422, filed on May 20, 2022.

(51) Int. Cl.

| | | |
|---|---|---|
| *A61K 31/407* | (2006.01) | |
| *A61K 9/00* | (2006.01) | |
| *A61K 9/06* | (2006.01) | |
| *A61K 47/08* | (2006.01) | |
| *A61K 47/10* | (2017.01) | |
| *A61K 47/38* | (2006.01) | |
| *A61P 17/00* | (2006.01) | |

(52) U.S. Cl.
CPC .......... *A61K 31/407* (2013.01); *A61K 9/0014* (2013.01); *A61K 9/06* (2013.01); *A61K 47/08* (2013.01); *A61K 47/10* (2013.01); *A61K 47/38* (2013.01); *A61P 17/00* (2018.01)

(58) Field of Classification Search
None
See application file for complete search history.

(56) References Cited

U.S. PATENT DOCUMENTS

| | | |
|---|---|---|
| 4,254,105 A | 3/1981 | Fukuda |
| 4,960,764 A | 10/1990 | Figueroa, Jr. et al. |
| 5,552,396 A | 9/1996 | Heath, Jr. et al. |
| 5,559,228 A | 9/1996 | Gillig et al. |
| 5,681,849 A * | 10/1997 | Richter ................... A61P 31/04 514/864 |
| 5,710,145 A | 1/1998 | Engel et al. |
| 5,962,417 A | 10/1999 | Gilchrest et al. |
| 5,962,524 A | 10/1999 | Rodelet |
| 6,015,807 A | 1/2000 | Engel et al. |
| 6,093,740 A | 7/2000 | Jirousek et al. |
| 6,387,383 B1 | 5/2002 | Dow et al. |
| 6,468,989 B1 | 10/2002 | Chang et al. |
| 6,514,506 B1 | 2/2003 | Mammone et al. |
| 6,517,847 B2 | 2/2003 | Dow et al. |
| 2004/0261280 A1 | 12/2004 | Znaiden et al. |
| 2005/0074497 A1 | 4/2005 | Schultz |
| 2007/0274936 A1 | 11/2007 | Kurfurst et al. |
| 2007/0274963 A1 | 11/2007 | Green et al. |
| 2007/0281988 A1 | 12/2007 | Cameron et al. |
| 2008/0096923 A1 | 4/2008 | Girach |
| 2010/0227879 A1 | 9/2010 | Mudumba et al. |
| 2012/0136037 A1 | 5/2012 | Czarnik |
| 2018/0185259 A1 | 7/2018 | Gilchrest et al. |
| 2019/0388321 A1 | 12/2019 | Gilchrest et al. |
| 2022/0110862 A1 | 4/2022 | Powala et al. |

FOREIGN PATENT DOCUMENTS

| | | | |
|---|---|---|---|
| CN | 1259866 A | 7/2000 | |
| EP | 0783887 A2 | 7/1997 | |
| WO | WO-9735998 A1 | 10/1997 | |
| WO | WO-9848795 A1 | 11/1998 | |
| WO | WO-2018118874 A1 * | 6/2018 | ........... A61K 31/407 |
| WO | WO-2019138291 A2 * | 7/2019 | ........... A61K 31/506 |
| WO | WO-2023225373 A1 | 11/2023 | |

OTHER PUBLICATIONS

Berge, Stephen M, et al., Pharmaceutical Salts. Journal of Pharmaceutical Sciences 66(1):1-19 (1977).
Bollag et al.: Protein Kinase Cα Puts the Handcuffs on Epidermal Keratinocyte Proliferation. Journal of Investigative Dermatology. 129:2330-2332 (2009) doi:10.1038/jid.2009.165.
Bos et al.: The 500 Dalton rule for the skin penetration of chemical compounds and drugs. Exp Dermatol. 9(3):165-169 (2000).
Cabodi et al.: A PKC-η/Fyn-Dependent Pathway Leading to Keratinocyte Growth Arrest and Differentiation. Molecular Cell. 6(5):1121-1129 (2000).
Chau et al.: Research Techniques Made Simple: Cutaneous Colorimetry: A Reliable Technique for Objective Skin Color Measurement. Elsevier. Jurnal of Investigative Dermatology. 140(1):pp. 3-12 (2020).
Clarke et al.: PKC inhibition and diabetic microvascular complications. Best Practice & Research Clinical Endocrinology & Metabolism,vol. 21(4):573-586 (2007) ISSN 1521-690X, https://doi.org/10.1016/j.beem.2007.09.007.

(Continued)

*Primary Examiner* — Melissa S Mercier
(74) *Attorney, Agent, or Firm* — Wilson Sonsini Goodrich & Rosati

(57) ABSTRACT

Provided herein are compositions comprising ruboxistaurin free base and its salts thereof and methods of use for treating conditions of the skin.

21 Claims, 13 Drawing Sheets

(56) References Cited

OTHER PUBLICATIONS

Denning et al.: Specific Protein Kinase C Isozymes Mediate the Induction of Keratinocyte Differentiation Markers by Calcium. Cell Growth Differ. 5(2):149-157 (1995).

Hu, Hong: Recent discovery and development of selective protein kinase C inhibitors. Elsevier. Drug Discovery Today. 1(10):438-447 (1996).

Jirousek et al.: (S)-13[(Dimethylamino)methyl]-10,11,14,15-tetrahydro-4,9:16,21-dimetheno-1H, 13H-dibenzo[e,k]pyrrolo[3,4-h][1,4,13]oxadiazacyclohexadecene-1,3(2H)-dione (LY333531) and related analogues: Isozyme selective inhibitors of protein kinase CBeta. J Med Chem. 39:2664-2671 (1996).

Kashiwagi et al.: Protein Kinase Cη (PKCη): Its Involvement in Keratinocyte Differentiation. Biochem. 132(6):853-857 (2002).

Kiss et al.: Bisindolylmaleimide I (GF 109203X) (CAS 133052-90-1). Biochim. Biophys. Acta. 1265:93-95 (1995).

Kramer et al.: Pityriarubins, Novel Highly Selective Inhibitors of Respiratory Burst from Cultures of the Yeast Malassezia furfur: Comparison with the Bisindolylmaleimide Arcyriarubin A. ChemBioChem. 6(12):2290-2297 (2005).

Martiny-Baron et al.: Selective inhibition of protein kinase C isozymes by the indolocarbazole Gö 6976. J. Biol. Chem. 268:9194-9197 (1993).

Narayanan et al.: Self-preserving personal care product. International Journal of Cosmetic Science. 39:301-309 (2017).

Park et al.: Protein Kinase C-beta Activates Tyrosinase by Phosphorylating Serine Residues in Its Cytoplasmic Domain. Journal of Biological Chem. 274(23):16470-16478 (1999).

Park et al.: The receptor for activated C-kinase-I (Rack-1) achors activated PKC-beta on melanosmoes. Journal of Cell Science. 117:3659-3668 (2004).

Park et al.: Topical Application of a Protein Kinase C Inhibitor Reduces Skin and Hair Pigmentation. Jurnal for Investigative Dermatology. 122:159-166 (2004).

PCT/US2017/067234 International Search Report and Written Opinion dated Apr. 3, 2018.

PCT/US2023/023014 International Search Report and Written Opinion dated Aug. 21, 2023.

Sehgal, Virendra N, et al., Melasma: Treatment Strategy. Journal of Cosmetic & Laser Therapy 13(6):265-279 (2011).

Seo et al.: PKCα induces differentiation through ERK1/2 phosphorylation in mouse keratinocytes. Experimental & Molecular Medicine. 36:292-299 (2004).

Sweetman: Martindale: The Completed Drug Reference, 33rd ed. Pharmaceutical Press. pp. 1576-1621 (2002).

The MERCK Index Online. entries for Enzastaurin (M4926), Midostaurin (M7534), Ruboxistaurin (M9693) and Staurosporine (M10198). Royal Society of Chemistry. pp. 1-7 (2013).

Toullec et al.: The bisindolylmaleimide GF 109203X is a potent and selective inhibitor of protein kinase C. J. Biol. Chem. 266(24):15771-15781 (1991).

U.S. Appl. No. 16/534,728 Final Office Action dated Feb. 14, 2022.
U.S. Appl. No. 16/534,728 Office Action dated Jun. 10, 2021.
U.S. Appl. No. 16/534,728 Office Action dated Jun. 14, 2022.
U.S. Appl. No. 16/534,728 Office Action dated Jun. 23, 2023.
U.S. Appl. No. 16/534,728 Restriction Requirement dated Feb. 4, 2021.
U.S. Appl. No. 15/846,629 Office Action dated Feb. 7, 2019.
U.S. Appl. No. 15/846,629 Restriction Requirement dated Aug. 15, 2018.
U.S. Appl. No. 16/534,728 Office Action dated Mar. 27, 2024.
U.S. Appl. No. 16/534,728, filed Aug. 7, 2019.

Vinik et al.: Treatment of symptomatic diabetic peripheral neuropathy with the protein kinase C beta-inhibitor ruboxistaurin mesylate during a 1 year, randomized, placebo-controlled, double-blind clinical trial. Clinical Therapeutics. 27(8):1164-1180 (2005).

Wilen et al., Tetrahedron Report No. 38. Strategies in Optical Resolutions. Tetrahedron. 33(21):2725-2736 (1977).

Zhou et al.: Bisindolylmaleimide VIII facilitates Fas-mediated apoptosis and inhibits T cell-mediated autoimmune diseases. Nat. Med. 5:42-48 (1999).

ICI Handbook. pp. 1673-1686 (1997).

* cited by examiner

Microscopic appearance of A) NA21, B) NA16, C) NA17, D) NA25 and E) NA26 following 2 mos. of storage at 25 °C (400 x magnification, non-polarised).

COMPOSITIONS AND FORMULATIONS FOR USE OF A PK INHIBITOR FOR THE PREVENTION, TREATMENT, AND IMPROVEMENT OF SKIN DISEASES, CONDITIONS, AND DISORDERS

CROSS-REFERENCE

This application is a continuation of International Application No. PCT/US2023/023014 filed on May 19, 2023, which claims the benefit of U.S. Provisional Application No. 63/344,422 filed May 20, 2022; U.S. Provisional Application No. 63/399,946 filed Aug. 22, 2022; and U.S. Provisional Application No. 63/489,697 filed Mar. 10, 2023, the contents of which are incorporated by reference in their entirety.

BACKGROUND

Hyperpigmentation is a commonly diagnosed disorder in which dark colored patches form in the skin. This skin darkening occurs in response to over production or irregular dispersion of melanin, a brown pigment which is produced by melanocytes in various skin layers, following cutaneous inflammation. Hyperpigmentation includes different skin discoloration disorders such as melasma, post-inflammatory hyperpigmentation, ephelides, and lentigines. The alterations in the skin color are the result of intrinsic factors and external insults to the skin including hormonal changes, inflammation, injury, acne, eczema, medication side effects, sun damage, etc. The hyperpigmentation of the skin can affect any race or gender but is most prevalent among skin-of-color patients and women.

Currently, the most commonly used therapy for hyperpigmentation is hydroquinone alone or in combination with other drugs. Hydroquinone is toxic to melanocytes and thus non-selectively inhibits melanin synthesis. Hydroquinone containing products are minimally effective at safe low concentrations and toxic at high concentrations, sometimes causing permanent pigment loss or dermal pigment deposition resulting in ochronosis. Topical application of bisindolylmaleimide, a selective PKC inhibitor, to a guinea pig model has been shown to inhibit UV induced neo-melanogenesis.

BRIEF SUMMARY

PKC-β inhibitors referred herein as ruboxistaurin or ruboxistaurin mesylate (also referred to herein as "methanesulfonic acid") monohydrate, represented by the formulas:

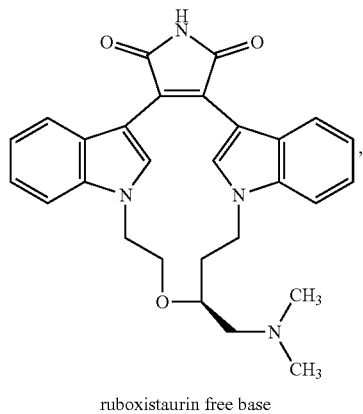

ruboxistaurin free base

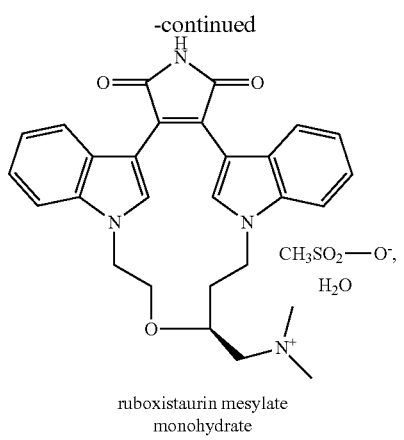

ruboxistaurin mesylate monohydrate and acceptable salts thereof, are particularly difficult to solubilize into a composition that is easily administered, effective, and is not irritating to the skin.

Common solvents used for formulating other small molecule compounds do not solubilize certain PK inhibitors as described herein, without limitation, including, ruboxistaurin free base, or ruboxistaurin salts (e.g., ruboxistaurin mesylate monohydrate) for use in a clinically or cosmetically acceptable composition. As such, there is urgent need for the development of a topical composition including a PK inhibitor as described herein, without limitation, including ruboxistaurin free base, or a ruboxistaurin salt (e.g., ruboxistaurin mesylate monohydrate) that can be delivered topically with reduced dermal irritation to treat skin disorders such as hyperpigmentation.

In a first aspect, the present disclosure provides a composition. The composition includes a compound having the structure:

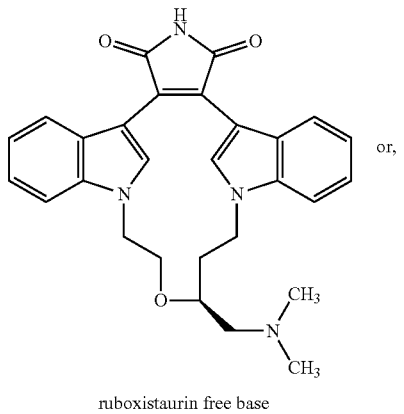

ruboxistaurin free base or,

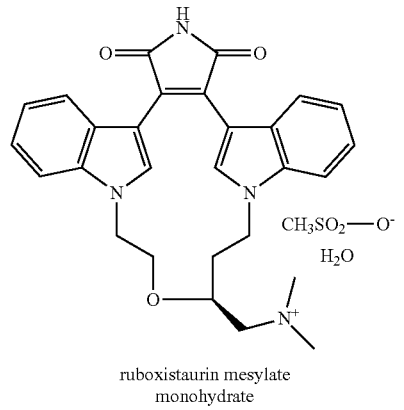

ruboxistaurin mesylate monohydrate or an acceptable salt thereof, and an excipient comprising:
a) an organic solvent and/or a penetration enhancer;
b) an antioxidant;
c) a gelling agent; or
d) an alcohol, or a combination thereof,
wherein the organic solvent and/or a penetration enhancer, the antioxidant, the alcohol and the gelling agent are defined and described herein. The composition may be formulated at 0.1% or 0.8% ruboxistaurin free base, ruboxistaurin mesylate monohydrate, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks.

In a second aspect, the present disclosure provides a composition comprising a compound having the structure:

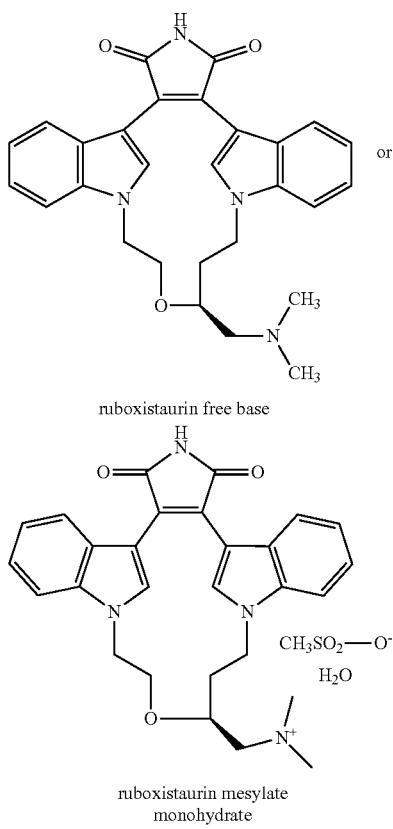

ruboxistaurin free base ruboxistaurin mesylate monohydrate or an acceptable salt thereof, and propylene glycol, 2-(2-ethoxyethoxy)ethanol, hydroxypropyl cellulose, polyethylene glycol, an antioxidant, and an alcohol. The composition may be formulated at 0.1% or 0.8% ruboxistaurin free base, ruboxistaurin mesylate monohydrate, or other salt thereof. The composition may be formulated at 0.08% to 0.8% ruboxistaurin mesylate monohydrate, ruboxistaurin free base, or a salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks.

In a third aspect, the present disclosure provides a method of treating a skin disease, condition or disorder in a subject in need thereof, the method including administering to the subject a composition, as described herein. In some aspects, the present disclosure additionally provides a method of treating conditions or disorders of the hair or hair follicles. The composition may be formulated at 0.08% to 0.8% PK inhibitor as described herein, without limitation, including ruboxistaurin free base, or a ruboxistaurin salt (e.g., ruboxistaurin mesylate monohydrate). In some cases the composition is administered once or twice daily. In some cases the composition is applied to 0.01% to 100% of the body surface area. In some cases, the composition is administered for about 12 weeks to about 6 months. In some cases, the composition is administered for about 4 weeks to about 8 weeks. In some cases, the composition is administered for about 8 weeks to about 12 weeks.

In a fourth aspect, the present disclosure provides a kit including a composition as described herein, in a container, a tube, a flexible aluminum tube or a laminated plastic tube, that may block UV light and/or minimize exposure to oxygen, with instructions for use. The composition may be formulated at 0.1% or 0.8% ruboxistaurin free base, ruboxistaurin mesylate monohydrate, or other salt thereof. The composition may be formulated at 0.08 to 0.8% ruboxistaurin, ruboxistaurin mesylate monohydrate, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks.

DETAILED DESCRIPTION OF THE INVENTION

General

Figure 1A:
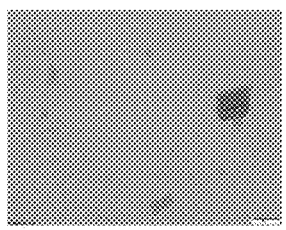
FIG. 1A-E Microscopic appearance of A) NA21, B) NA16, C) NA17, D) NA25 and E) NA26 following 2 mos. of storage at 25° C. (400× magnification, non-polarised).
Figure 1B:
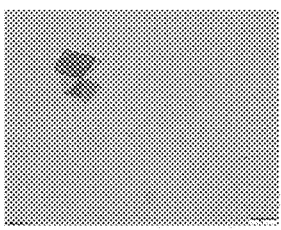
Figure 1C:
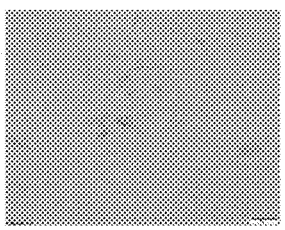
Figure 1D:
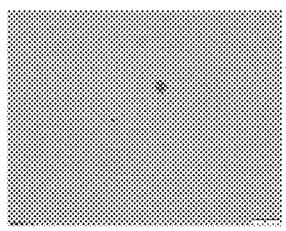
Figure 1E:
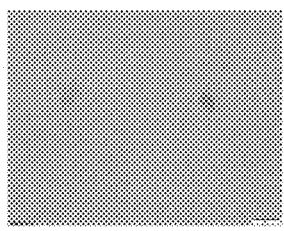

Protein kinase C (PKC or PRKC) is an intracellular signaling molecule that can regulate many vascular functions, including permeability, vasodilator release, endothelial activation, and growth factor signaling. Protein kinase C is a family of isoenzymes comprising at least 12 members of which the R isoform has been linked to the development of diabetic microvascular complications and to the production of melanin. In the skin, PKC-β expression, which leads to the production of melanin and pigmentation in human skin, appears to be restricted to melanocytes. Inhibition of PKC-0, and subsequently the inhibition of production of melanin, is an attractive and selective target for treatment of hyperpigmentation. While the normal redistribution and increased production of melanin following exposure to ultraviolet (UV) radiation may be beneficial, the excessive, or uneven production of melanin can produce undesired hyperpigmentation causing conditions such as melasma, lentigos, PIH, and other dyschromias (uneven and/or abnormal pigmentation). Tyrosinase, which converts tyrosine to DOPA and DOPA to dopaquinone, is the key enzyme in the melanin synthetic pathway and requires phosphorylation by PKC-β for activity. Inhibitors of PKC-β have been shown to decrease melanogenesis.

Provided herein are compositions including ruboxistaurin free base, ruboxistaurin mesylate, or an acceptable salt thereof, and methods of using these compositions for the treatment of skin diseases, conditions, or disorders. In some embodiments, the compositions are administered topically, thereby treating the skin diseases, conditions, or disorders. In some embodiments, the skin diseases, conditions or disorders include, but are not limited to, hyperpigmentation, hypopigmentation, dyschromia, melasma, post inflammatory hyperpigmentation or hypopigmentation, discoid lupus erythematous, phytophotodermatitis, lentigines (e.g., age spots), birth marks, café au lait macules, acanthosis nigricans, burn associated hyperpigmentation or hypopigmentation, drug-induced hyperpigmentation or hypopigmentation (e.g., sulfonamide, tetracycline, NSAID, barbiturate, and carbamazepine induced hyperpigmentation), injury induced hyperpigmentation or hypopigmentation, primary biliary cirrhosis associated hyperpigmentation or hypopigmentation, Addison's disease associated hyperpigmentation or hypopigmentation, hemochromatosis associated hyperpigmentation or hypopigmentation, hyperthyroidism associated hyperpigmentation or hypopigmentation, melanocytic naevi, ephelides (freckles), seborrheic keratosis, skin cancer-associated hyperpigmentation or hypopigmentation, infection associated hyperpigmentation or hypopigmentation (e.g., *Pityriasis versicolor*, tinea versicolor, erythrasma), eczema, photocontact, photoallergic, or phototoxicdermatitis, ichthyosis, axillary freckling or café au lait macules associated with neurofibromatosis, or hyperpigmentation or hypopigmentation associated with ultra-violet (UV) radiation exposure or photodamage, e.g., sun exposure or a tanning response, or a combination of two or more thereof. In some embodiments the condition, disease, or disorder includes aesthetic indications including skin lightening, skin brightening, skin tone evening, photodamage hyperpigmentation, or polychromatic pigmentation. In some embodiments this also includes evening out skin pigment irregularities resulting from vitiligo or other depigmenting conditions and dyspigmentation. The condition may also be a condition, disease, or disorder of the hair or hair follicles and may be hirsutism/hypertrichosis and hair pigmentation. In particular, the compositions are useful for treating hyperpigmentation disorders and dyschromia.

Definitions

The abbreviations used herein have their conventional meaning within the chemical and biological arts.

"Alkylene glycol" refers to a compound having the formula of H—[O-alkylene]-OH, wherein the alkylene group has 2 to 6, 2 to 4, or 2 to 3 carbon atoms. In some embodiments, the alkylene glycol is a $C_{2-6}$ alkylene glycol. In some embodiments, the $C_{2-6}$ alkylene glycol is propylene glycol (1.2-propanediol).

"Di-alkylene glycol" refers to a compound having the formula of HO-(alkylene-O)$_2$—H, wherein the alkylene group has 2 to 6, 2 to 4, or 2 to 3 carbon atoms. In some embodiments, the di-alkylene glycol is a di-($C_{2-6}$ alkylene) glycol. In some embodiments, the di-($C_{2-6}$ alkylene) glycol is dipropylene glycol. Dipropylene glycol can include one or more isomers, for example 4-oxa-2,6-heptandiol, 2-(2-hydroxy-propoxy)-propan-1-ol, 2-(2-hydroxy-1-methylethoxy)-propan-1-ol, and 3,3'-oxybis(propan-1-ol).

"Polyethylene glycol" refers to a polymer having the formula of HO—$(CH_2CH_2O)_n$—OH with variations in subscript "n". Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to PEG200, PEG300, PEG400, PEG600, and PEG900. The number following the "PEG" in the name refers to the average molecular weight of the polymer.

"USP/NF Grade, Ph. Eur. Grade, BP Grade and JP Grade, etc" excipients refers to excipients (e.g., propylene glycol, glycerol, polyethylene glycol, such as PEG200 and PEG400, and the like) meet or exceed requirements of the United States Pharmacopeia/National Formulary (USP/NF), European Pharmacopeia, British Pharmacopeia and Japanese Pharmacopeia, respectively.

"Super refined" excipients refer to excipients that are stripped of their impurities. Super refining removes polar impurities (including potentially reactive primary and secondary oxidation products) from an excipient without altering its chemical composition. The removal of these impurities helps to reduce excipient-Active Pharmaceutical Ingredient (API) interaction and subsequent API degradation, thereby maintaining both the stability of the drug and the final composition or formulation. In addition, the removal of these impurities can minimize cellular irritation, ideal for various drug administration routes. Super Refined excipients of the present invention include a super refined propylene glycol.

"Super refined propylene glycol" or "S.R. propylene glycol" refers to a highly purified propylene glycol that can enhance drug activity and composition (or formulation) stability. In some embodiments, S.R. propylene glycol has a purity of no less than about 99.5%, 99.6%, 99.7%, 99.8%, or 99.9%. In some embodiments, S.R. propylene glycol has a purity of no less than about 99.8% or 99.9%.

"Transcutol" is represented by the formula: $CH_3CH_2OCH_2CH_2OCH_2CH_2OH$, which has a preferred IUPAC name of 2-(2-ethoxyethoxy)ethanol. Other names for 2-(2-Ethoxyethoxy)ethanol includes diethylene glycol monoethyl ether (abbreviated as DGME or DEGEE), diethylene glycol ethyl ether (abbreviated as DEGEE), ethyldiglycol, dioxitol, 3,6-dioxa-1-octanol, Carbitol, Carbitol Cellosolve, Polysolv DE, or Dowanal DE. Transcutol includes "Transcutol P", "Transcutol CG", and "Transcutol HP".

"Transcutol P" refers to a high purity grade of 2-(2-ethoxyethoxy)ethanol. "Transcutol CG" refers to a specific grade of 2-(2-ethoxyethoxy)ethanol, which is a powerful solubilizer and efficacy booster that has been used in the cosmetic and pharmaceutical industries. "Transcutol HP" refers to a highly purified grade of 2-(2-ethoxyethoxy)ethanol that can enhance drug activity and composition (or formulation) stability. In some embodiments, Transcutol P, CG, or HP has a purity of no less than about 99.5%, 99.6%, 99.7%, 99.8%, or 99.9%. In some embodiments, Transcutol P or HP has a purity of no less than 99.8% or 99.9%. In some embodiments, Transcutol HP has a purity of about 99.90%.

"Fatty alcohol" refers to a primary alcohol with a long aliphatic chain, which is either saturated or unsaturated. The fatty alcohol can also range from as few as 4-6 carbons to as many as 22-26 carbons. The fatty alcohol includes, but is not limited to, capric alcohol, undecyl alcohol, lauryl alcohol, tridecyl alcohol, myristyl alcohol, pentadecyl alcohol, cetyl alcohol, palmitoleyl alcohol (unsaturated), heptadecyl alcohol, stearyl alcohol, oleyl alcohol (unsaturated), nonadecyl alcohol, arachidyl alcohol, heneicosyl alcohol, behenyl alcohol, erucyl alcohol (unsaturated), and lignoceryl alcohol.

"Fatty ester" or "fatty acid ester" refers to a type of ester that results from the combination of a fatty acid with an alcohol. When the alcohol is a polyethylene glycol, the fatty ester refers to a polyoxyethylene fatty ester or a polyoxyethylene fatty acid ester.

"Fatty ether" refers to a type of ether that results from the combination of a fatty alcohol with a second alcohol. When the second alcohol is a polyethylene glycol, the fatty ether refers to a polyoxyethylene fatty ether.

"Polysorbate" refers a type of fatty ester that results from an ethoxylated sorbitan (a polyethylene glycol derivative of sorbitol) with a fatty acid. Examples of polysorbates include Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), and Polysorbate 80 (polyoxyethylene (20) sorbitan monooleate). Suitable polysorbates include, but are not limited to the Tween™ series (available from Uniqema), which includes Tween 20 (polyoxyethylene (20) sorbitan monolaurate), Tween 40 (polyoxyethylene (20) sorbitan monopalmitate), Tween 60 (polyoxyethylene (20) sorbitan monostearate), and Tween 80 (polyoxyethylene (20) sorbitan monooleate). Other suitable polysorbates include the ones listed in R. C. Rowe and P. J. Shesky, Handbook of pharmaceutical excipients, (2006), 5th ed., which is incorporated herein by reference in its entirety.

"Glyceride" refers to a fatty ester when the alcohol component is glycerol. The glyceryl fatty esters (or glycerides) produced can be monoglycerides, diglycerides, or triglycerides. "Monoglyceride" is glyceride consisting of one fatty acid chain covalently bonded to a glycerol molecule through an ester linkage. "Diglyceride" is glyceride consisting of two fatty acid chains covalently bonded to a glycerol molecule through ester linkages. "Triglyceride" is glyceride consisting of three fatty acid chains covalently bonded to a glycerol molecule through ester linkages.

"Salt" refers to acid or base salts of the compounds of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound that is complexed to water molecule. The compounds of the present invention can be complexed with ½ water molecule or from 1 to 10 water molecules.

"Composition" or "formulation" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the composition (or formulation) and not deleterious to the recipient thereof.

For any one of topical compositions as described herein, the content of water refers to a total amount by weight including the portion from a pH adjusting solution (when present) (e.g., 0.1 M, 0.5 M, or 1 M solution of citric acid in water), ethanol (if ethanol is not absolute ethanol), and the final Q.S. 100 (Q.S stands for quantum satis).

"A relative purity of the compound in the topical composition" refers to the purity of the compound (e.g., a PK inhibitor as described herein, without limitation, including ruboxistaurin free base, or a ruboxistaurin salt (e.g., ruboxistaurin mesylate monohydrate)) at a certain time point (e.g., 8 weeks) stored under stressed conditions (e.g., 40° C.) or under normal storage conditions (e.g., room temperature or 25° C.) as compared to an initial purity of the compound at time zero (i.e., day 0). As always, the relative purity of the compound at time zero (i.e., day 0) is set as 100%.

"About" means a range of values including the specified value, which a person of ordinary skill in the art would consider reasonably similar to the specified value. In some embodiments, the term "about" means within a standard deviation using measurements generally acceptable in the art. In some embodiments, about means a range extending to +/−10% of the specified value. In some embodiments, about means the specified value.

"Substantially free of . . . " refers to a composition containing no more than 10% by weight of other excipients, such as a di-($C_{2-6}$ alkylene) glycol, glycerol, a fatty alcohol, a fatty ester (e.g., Polysorbate), a fatty ether, or combinations thereof, each of which is defined and described herein. Polyethylene glycol (e.g., PEG200 and/or PEG400) and/or $C_{1-3}$ alkyl-$(OCH_2CH_2)_{1-5}$—OH (e.g., 2-(2-ethoxyethoxy)ethanol or Transcutol HP) contain impurities including ethylene glycol and/or diethylene glycol. When the polyethylene glycol (e.g., PEG200 and/or PEG400) and/or $C_{1-3}$ alkyl-$(OCH_2CH_2)_{1-5}$—OH (e.g., 2-(2-ethoxyethoxy)ethanol or Transcutol HP) are present in a composition, the composition contains no more than 0.5% by weight of ethylene glycol and/or diethylene glycol as impurities. In some embodiments, when the polyethylene glycol (e.g., PEG200 and/or PEG400) and/or $C_{1-3}$ alkyl-$(OCH_2CH_2)_{1-5}$—OH (e.g., 2-(2-ethoxyethoxy)ethanol or Transcutol HP) are present in a composition, the composition contains no more than 0.25% by weight of ethylene glycol and/or diethylene glycol as impurities.

"Inhibition", "inhibits" and "inhibitor" refer to a compound that prohibits or a method of prohibiting, a specific action or function.

"Administering" refers to providing a composition or formulation to a subject (e.g., a patient, such as a human patient) via a desired route, such as via topical administration. Topical administration may comprise, for example, application of a composition in the form of a gel, ointment, lotion, foam, emollient, or as a component of a patch, tape, film, wafer, or bandage to a surface of a subject, such as to the skin of the subject. The area over which the composition is applied may vary based upon, e.g., the condition of the subject as well as the characteristics of the composition (e.g., form, drug load, etc.).

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, cats, primates, goat, sheep, cows, deer, and other non-mammalian animals. In some embodiments, the patient or subject is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Compositions

I. Compositions

In a first aspect, the present disclosure provides a composition. The composition includes a PK inhibitor as described herein, without limitation, including, ruboxistaurin free base, ruboxistaurin salt (e.g., mesylate, or another acceptable salt thereof), and one or more excipients. As will be appreciated, some of the one or more excipients of the compositions described herein can possess multiple functions. For example, a given substance may act as both a solvent and an enhancer, both an antioxidant and a stabilizer, both an emulsifier and a surfactant, both an emulsifier and a thickening agent, and so on. In some such cases, the function of a given substance can be considered singular, even though its properties may allow multiple functionality. The composition may be formulated at 0.1% or 0.8% PK inhibitor as described herein, without limitation, such as ruboxistaurin free base, or a ruboxistaurin salt (e.g., ruboxistaurin mesylate monohydrate). The composition may be formulated at 0.08% or 0.8% w/w ruboxistaurin free base, ruboxistaurin mesylate monohydrate, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks.

In some embodiments, as used herein example PK inhibitors include ruboxistaurin mesylate monohydrate, ruboxistaurin free base, or an acceptable salt thereof, includes a compound having the structure:

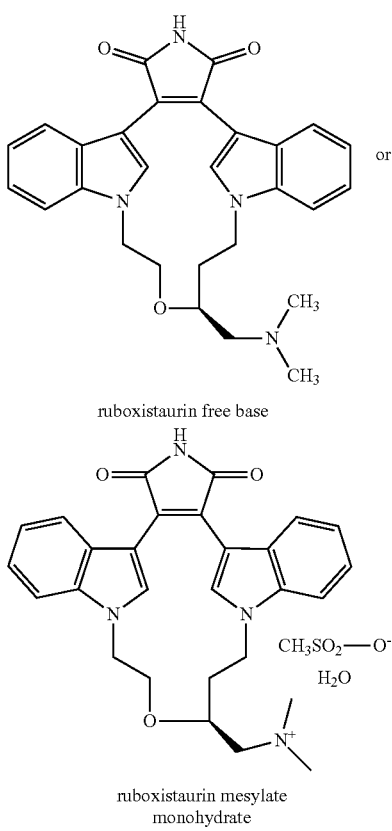

ruboxistaurin free base ruboxistaurin mesylate monohydrate or an acceptable salt thereof.

Non-limiting examples of excipients include: an organic solvent and/or penetration enhancer, an antioxidant, a gelling agent, and one or more additional agents such as an alcohol or a humectant. In some compositions, an excipient of the one or more excipients comprises an organic solvent, which includes one or more organic solvents, such as 1, 2, 3, 4, or 5 organic solvents. In some compositions, an excipient of the one or more excipients comprises a penetration enhancer, which includes one or more penetration enhancers, such as 1, 2, 3, 4 or 5 penetration enhancers. In some cases, the organic solvent is a penetration enhancer. In some compositions, an excipient of the one or more excipients comprises an antioxidant, which includes one or more antioxidants, such as 1, 2, 3, 4 or 5 antioxidants. In some compositions, an excipient of the one or more excipients comprises a gelling agent, which includes one or more gelling agents, such as 1, 2, 3, 4, or 5 gelling agents. In some compositions an excipient of the one or more excipients comprises one or more additional agents, such as an alcohol. In some compositions the alcohol is a humectant.

In some embodiments, the composition comprises an organic solvent and/or a penetration enhancer. The organic solvent may be a penetration enhancer. In some embodiments, the composition comprises an organic solvent or a penetration enhancer. Non-limiting example compositions comprise the organic solvent and/or penetration enhancer and one or more additional excipients. The one or more additional excipients may be an antioxidant. The one or more additional excipients may be an alcohol. The one or more additional excipients may be a gelling agent. The one or more additional excipients may comprise the antioxidant, alcohol, gelling agent, or two or more thereof. The one or more additional excipients may comprise the antioxidant, alcohol, and gelling agent.

In some embodiments, the composition comprises an antioxidant. Non-limiting example compositions comprise the antioxidant and one or more additional excipients. The one or more additional excipients may be an organic solvent and/or penetration enhancer. The one or more additional excipients may be an alcohol. The one or more additional excipients may be a gelling agent. The one or more additional excipients may comprise the organic solvent and/or penetration enhancer, alcohol, gelling agent, or two or more thereof. The one or more additional excipients may comprise the organic solvent and/or penetration enhancer, alcohol, and gelling agent.

In some embodiments, the composition comprises a gelling agent. Non-limiting example compositions comprise the gelling agent and one or more additional excipients. The one or more additional excipients may be an antioxidant. The one or more additional excipients may be an alcohol. The one or more additional excipients may be an organic solvent and/or penetration enhancer. The one or more additional excipients may comprise the antioxidant, alcohol, organic solvent and/or penetration enhancer, or two or more thereof. The one or more additional excipients may comprise the antioxidant, alcohol, and organic solvent and/or penetration enhancer.

In some embodiments, the composition comprises an alcohol. Non-limiting example compositions comprise the solvent and one or more additional excipients. The one or more additional excipients may be a penetration enhancer. The one or more additional excipients may be an antioxidant. The one or more additional excipients may be a gelling agent. The one or more additional excipients may comprise the antioxidant, penetration enhancer, gelling agent, or two or more thereof. The one or more additional excipients may comprise the antioxidant, penetration enhancer, and gelling agent.

II. PK Inhibitors

In some embodiments, compositions include PK inhibitors described herein that prevent, inhibit, or decrease melanin production by inhibiting or modulating a protein kinase. In some embodiments the composition the inhibits or modulates a protein kinase, including but not limited to Protein kinase C, Protein kinase C alpha, Protein kinase C beta, Protein kinase B, and/or Protein kinase A. In some embodiments the composition inhibits PKCα, PKCα, PKCβ$_1$, PKCβ$_2$, PKCδ, PKCε, PKCθ, PKCζ, PKCγ, PKCλ, PKCμ, PKCτ, PKCη. In some embodiments the composition inhibits or modulates PRKCA, PKCα, PRKCB, PKCα, PRKCG, PKCγ, PRKCD, PKCσ, PRKCQ, PKCθ, PRKCE, PKCε, PRKCH, PKCη, PRKCI, PKCζ, PRKCZ, PKCτ. In some embodiments the compound described here-in inhibits or modulates PKA. In some embodiments the compound inhibits or modulates PRKACA, PRKACB, PRKACG, PRKAR1A, PRKAR1B, PRKAR2A, PRKAR2B. In some embodiments the composition includes a pan-protein kinase inhibitor. In some embodiments the composition includes a pan-protein kinase C inhibitor. In some embodiments the composition inhibits or activates a modulator of a protein kinase.

In some embodiments described herein, the composition includes a PKC inhibitor. In some embodiments, the PKC inhibitor is a PKCβ inhibitor. In some embodiments, the PKC inhibitor is a PKCβ$_1$ and/or PKCβ$_2$ inhibitor. In some embodiments, the PKCβ inhibitor includes ruboxistaurin free base or a salt thereof. In some embodiments, the ruboxistaurin freebase or a salt thereof is ruboxistaurin free base. In some embodiments, the ruboxistaurin or a salt thereof is ruboxistaurin mesylate monohydrate, ruboxistaurin hydrochloride, ruboxistaurin sulfate, ruboxistaurin tartrate, ruboxistaurin succinate, ruboxistaurin acetate, or ruboxistaurin phosphate.

The present disclosure features PKC-β inhibitors for use to treat a disease or disorder described herein (e.g., a hyperpigmentation condition). In some embodiments, the PKC-β inhibitor comprises a bis-indolylmaleimide, a phthalimide, or a derivative thereof. In some embodiments, the PKC-β inhibitor is a compound of Formula (I):

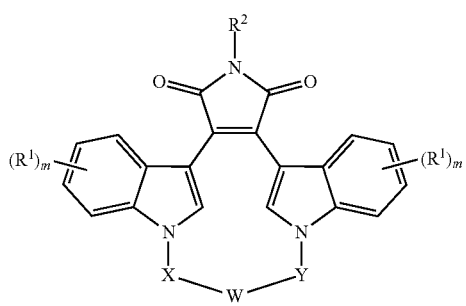

(I)

or a pharmaceutically acceptable salt, stereoisomer, racemate, or solvate thereof, wherein:

W is —O—, —S—, —S(O)—, —S(O)$_2$—, —C(O)—, $C_2$-$C_6$ alkylene, substituted alkylene, $C_2$-$C_6$ alkenylene, substituted alkenylene, aryl, aryl($CH_2$)$_m$O, heterocyclyl, heterocyclyl($CH_2$)$_m$O, —NR$^3$—, —N(O)R$^3$—, —C(O)NH—, or —NHC(O)—;

each of X and Y is independently $C_1$-$C_4$ alkylene, substituted alkylene, or X, Y, and W combine to form —($CH_2$)$_n$-AA-;

each R$^1$ is independently hydrogen, halo, $C_1$-$C_4$ alkyl, hydroxyl, $C_1$-$C_4$ alkoxy, $C_1$-$C_4$ haloalkyl, nitro, —NR$^4$R$^5$, or —NHC(O)($C_1$-$C_4$ alkyl);

R$^2$ is hydrogen, —$CH_3$C(O), —$NH_2$, or hydroxyl;

R$^3$ is hydrogen, ($CH_2$)$_m$aryl, $C_1$-$C_4$ alkyl, —C(O)O($C_1$-$C_4$ alkyl), —C(O)NR$^4$R$^5$, —(C=NH)$NH_2$, —S(O)($C_1$-$C_4$ alkyl), —S(O)$_2$(NR$^4$R$^5$), or —S(O)$_2$($C_1$-$C_4$ alkyl);

each R$^4$ and R$^5$ is independently hydrogen, $C_1$-$C_4$ alkyl, phenyl, benzyl, or R$^4$ and R$^5$ are taken together with the nitrogen to which they are bonded to form a saturated or unsaturated 5- or 6-membered ring;

AA is an amino acid residue;

each m is independently 0, 1, 2, or 3; and n is independently 2, 3, 4, or 5.

In some embodiments, X—W—Y contains 4 to 30 atoms, which may be further substituted or unsubstituted. In some embodiments, X—W—Y contains 5 atoms, 6 atoms, 7 atoms, 8 atoms, 9 atoms, 10 atoms, 11 atoms, 12 atoms, 13 atoms, 14 atoms, 15 atoms, 16 atoms, 17 atoms, 18 atoms, 19 atoms, 20 atoms, 21 atoms, 22 atoms, 23 atoms, 24 atoms, 25 atoms, 26 atoms, 27 atoms, 28 atoms, 29 atoms, or 30 atoms, which may be further substituted or unsubstituted. In some embodiments, X—W—Y contains 10 to 30 atoms, which may be further substituted or unsubstituted. In some embodiments, X—W—Y contains 20 to 30 atoms, which may be further substituted or unsubstituted.

In some embodiments, each of R$^1$ and R$^2$ is independently hydrogen. In some embodiments, each of X and Y is independently alkylene or substituted alkylene. In some embodiments, W is substituted alkylene, —O—, —S—, —C(O)NH—, —NHC(O)—, or NR$^3$. In some embodiments, each of R$^1$ and R$^2$ is independently hydrogen, each of X and Y is independently alkylene or substituted alkylene, and W is substituted alkylene, —O—, —S—, —C(O)NH—, —NHC(O)—, or NR$^3$.

In some embodiments, the compound of Formula (I) is a compound of Formula (Ia):

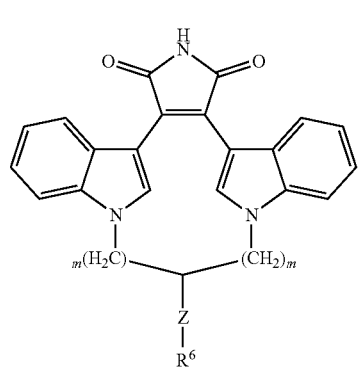

(Ia)

or a pharmaceutically acceptable salt, stereoisomer, racemate, or solvate thereof, wherein Z is —($CH_2$)$_p$— or —($CH_2$)$_p$—O—($CH_2$)$_p$;

R$^6$ is hydroxyl, —SH, $C_1$-$C_4$ alkyl, ($CH_2$)$_m$aryl, —NH(aryl), N($CH_3$)($CF_3$), NH($CF_3$), or —NR$^4$R$^5$;

R$^4$ is hydrogen or $C_1$-$C_4$ alkyl;

R$^5$ is hydrogen, $C_1$-$C_4$ alkyl, or benzyl;

p is 0, 1, or 2; and each m is independently 2 or 3.

In some embodiments, m is 2. In some embodiments, m is 3. In some embodiments, Z is $CH_2$. In some embodiments, R$^6$ is $NH_2$, NH($CF_3$), or N($CH_3$)$_2$. In some embodiments, Z is $CH_2$ and R$^6$ is $NH_2$, NH($CF_3$), or N($CH_3$)$_2$. In some embodiments, m is 2, Z is $CH_2$, and R$^6$ is $NH_2$, NH($CF_3$), or N($CH_3$)$_2$.

In other embodiments, the compound of Formula (I) is a compound of Formula (Ib):

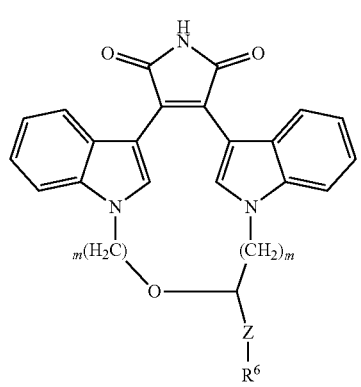

(Ib)

or a pharmaceutically acceptable salt, stereoisomer, racemate, or solvate thereof, wherein Z is —(CH$_2$)$_p$—;
R$^6$ is N(CH$_3$)(CF$_3$), NH(CF$_3$), or —NR$^4$R$^5$;
each of R$^4$ and R$^5$ is independently hydrogen or C$_1$-C$_4$ alkyl;
R$^5$ is hydrogen, C$_1$-C$_4$ alkyl, or benzyl;
p is 0, 1, or 2; and
each m is independently 2 or 3.

In some embodiments, m is 2. In some embodiments, m is 3. In some embodiments, p is 1 or 2. In some embodiments, p is 1. In some embodiments, p is 2. In some embodiments, R$^6$ is —NR$^4$R$^5$ and each of R$^4$ and R$^5$ is independently C$_1$-C$_4$ alkyl (e.g., CH$_3$). In some embodiments, R$^6$ is N(CH$_3$)$_2$. In some embodiments, m is 2 and p is 1. In some embodiments, m is 2, p is 1, and R$^6$ is N(CH$_3$)$_2$.

In other embodiments, the compound of Formula (I) is a compound of Formula (Ic):

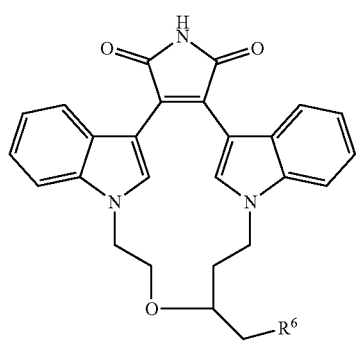

(Ic)

or a pharmaceutically acceptable salt, stereoisomer, racemate, or solvate thereof, wherein R$^6$ is N(CH$_3$)(CF$_3$), NH(CF$_3$), or —NR$^4$R$^5$.

In some embodiments, R$^6$ is —NR$^4$R$^5$ and each of R$^4$ and R$^5$ is independently C$_1$-C$_4$ alkyl (e.g., CH$_3$). In some embodiments, R$^6$ is N(CH$_3$)$_2$.

In other embodiments, the compound of Formula (I) is a compound of Formula (Id):

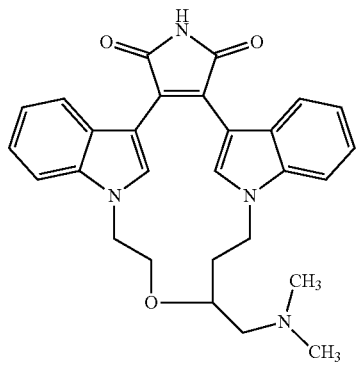

(Id)

or a pharmaceutically acceptable salt, stereoisomer, racemate, or solvate thereof. In some embodiments, the compound of Formula (Id) is 9-[(dimethylamino)methyl]-6,7,10,11-tetrahydro-9H,18H-5,21:12,17-di(metheno)dibenzo[e,k]pyrrolo[3,4-h][1,2,13]oxadiazacyclohexadecine-18,20-dione, e.g., ruboxistaurin, or a pharmaceutically acceptable salt, stereoisomer, racemate, or solvate thereof.

In other embodiments, the compound of Formula (I) is a compound of Formula (Ie):

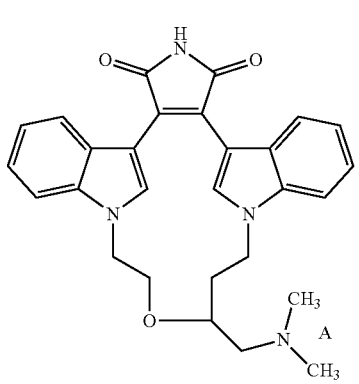

(Ie)

or a pharmaceutically acceptable salt, stereoisomer, racemate, or solvate thereof, wherein A is a counterion of the N(CH$_3$)$_2$ moiety. In some embodiments, the compound of Formula (Ie) is 9-[(dimethylamino)methyl]-6,7,10,11-tetrahydro-9H,18H-5,21:12,17-di(metheno)dibenzo[e,k]pyrrolo[3,4-h][1,2,13]oxadiazacyclohexadecine-18,20-dione salt, e.g., a ruboxistaurin salt, or a pharmaceutically acceptable salt, stereoisomer, racemate, or solvate thereof In some embodiments, A is acetic acid, benzoic acid, bromine, carbonic acid, chlorine, citric acid, fluorine, fumaric acid, gluconic acid, hydrochloric acid, hydrobromic acid, hydrofluoric acid, iodine, lactic acid, phosphonic acid, phosphoric acid, methanesulfonic acid, sulfonic acid, tartaric acid, or a salt thereof. In some embodiments, A is acetic acid, benzoic acid, citric acid, hydrochloric acid, hydrobromic acid, hydrofluoric acid, methanesulfonic acid, tartaric acid, or a salt thereof. In some embodiments, A is methanesulfonic acid or a salt thereof.

In other embodiments, the compound of Formula (I) is a compound of Formula (If):

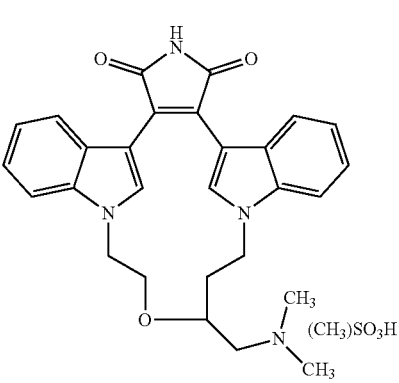

(If)

or a pharmaceutically acceptable salt, stereoisomer, racemate, or solvate thereof.

In some embodiments, the PKC-β inhibitor (e.g., a compound of Formula (If)) is 9-[(dimethylamino)methyl]-6,7,10,11-tetrahydro-9H,18H-5,21:12,17-di(metheno)dibenzo[e,k]pyrrolo[3,4-h][1,2,13]oxadiazacyclohexadecine-18,20-dione mesylate, e.g., ruboxistaurin mesylate, or a pharmaceutically acceptable salt, stereoisomer, racemate, or solvate thereof.

The compound of Formula (I) (e.g., a compound of Formulas (Ia), (Ib), (Ic), (Id), (Ie), or (If)) may exists as a solvate, e.g., a solvate with water (i.e., a hydrate), methanol, ethanol, dimethylformamide, ethyl acetate, and the like. Mixtures of solvates may also be prepared. The source of the solvate may be derived from a solvent encountered during the synthesis of the compound, e.g., the solvent of purification (e.g., crystallization) or in preparation of purification (e.g., crystallization), or adventitious to such solvent. In one embodiment, the compound of Formula (I) (e.g., a compound of Formulas (Ia), (Ib), (Ic), (Id), (Ie), or (If)) is present as a monohydrate or trihydrate solvate.

In some embodiments, the PKC-β inhibitor of Formula (I) may be a stereoisomer or racemate of the compound of Formula (I). In certain embodiments, the PKC-β inhibitor of Formula (If) is a compound of Formula (If-1) or a compound of Formula (If-2):

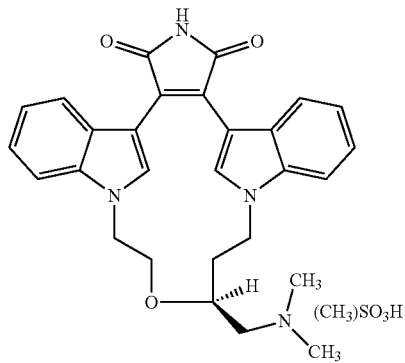

(If-1)

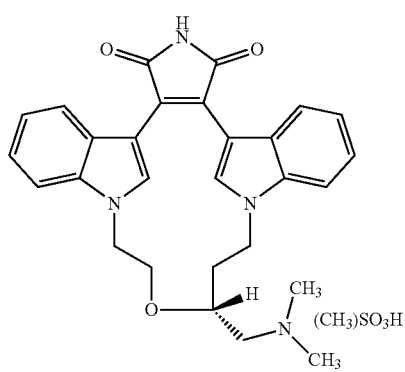

(If-2)

or a pharmaceutically acceptable salt, stereoisomer, racemate, or solvate thereof. In some embodiments, the PKC-β inhibitor (e.g., a compound of Formula (I)) is (9S)-9[(dimethylamino)methyl]-6,7,10,11-tetrahydro-9H,18H-5,21:12,17-di(metheno)dibenzo[e,k]pyrrolo[3,4-h][1,2,13]oxadiazacyclohexadecine-18,20-dione mesylate (e.g., Formula (If-1)) or (9R)-9[(dimethylamino)methyl]-6,7,10,11-tetrahydro-9H,18H-5,21:12,17-di(metheno)dibenzo[e,k]pyrrolo[3,4-h][1,2,13]oxadiazacyclohexadecine-18,20-dione mesylate (e.g., Formula (If-2)), e.g., ruboxistaurin mesylate, or a pharmaceutically acceptable salt, stereoisomer, racemate, or solvate thereof.

Preparation of a compound of Formula (I) (e.g., a compound of Formulas (Ia), (Ib), (Ic), (Id), (Ie), (If), (If-1), or (If-2)) may be achieved through the methods described in U.S. Pat. Nos. 5,552,396 and 6,015,807, each of which is incorporated herein by reference in its entirety. However, preparation of a compound of Formula (I) (e.g., a compound of Formulas (Ia), (Ib), (Ic), (Id), (Ie), (If), (If-1), or (If-2)) may be accomplished using other protocols or methods known to one of skill in the art.

In some embodiments, the PKC-β inhibitor is a compound of Formula (II):

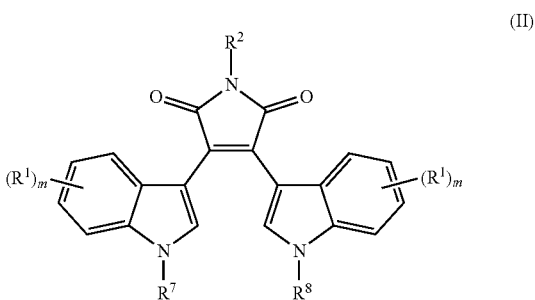

(II)

or a pharmaceutically acceptable salt, stereoisomer, racemate, or solvate thereof, wherein:

each $R^1$ is independently hydrogen, halo, $C_1$-$C_4$ alkyl, hydroxyl, $C_1$-$C_4$ alkoxy, haloalkyl, nitro, $NR^4R^5$, or —NHC(O)($C_1$-$C_4$ alkyl);

$R^2$ is hydrogen, —$CH_3C(O)$, —$NH_2$, or hydroxyl;

each $R^4$ and $R^5$ is independently hydrogen, $C_1$-$C_4$ alkyl, phenyl, benzyl, or $R^4$ and $R^5$ are taken together with the nitrogen to which they are bonded to form a saturated or unsaturated 5- or 6-membered ring;

$R^7$ is hydrogen or $C_1$-$C_4$ alkyl;

$R^8$ is cycloalkyl or heterocyclyl, each of which is substituted with one or more $R^9$;

$R^9$ is $C_1$-$C_4$ alkyl, $C_1$-$C_4$ alkoxy, $C_1$-$C_4$ haloalkyl, halo, cyano, nitro, aryl, arylalkyl, heteroaryl, or heteroarylalkyl, each of which is optionally substituted with one or more $R^{10}$;

each $R^{10}$ is independently halo, $C_1$-$C_4$ alkyl, $C_1$-$C_4$ alkoxy, $C_1$-$C_4$ haloalkyl, cyano, or nitro; and each m is independently 0, 1, 2, or 3.

In some embodiments, each m is 0.

In some embodiments, $R^2$ is hydrogen.

In some embodiments, $R^7$ is $C_1$-$C_4$ alkyl (e.g., methyl or ethyl). In some embodiments, $R^7$ is methyl.

In some embodiments, $R^8$ is heterocyclyl. In some embodiments, $R^8$ is a nitrogen-containing heterocyclyl. In some embodiments, $R^8$ is a 6-membered nitrogen-containing heterocyclyl. In some embodiments, $R^8$ is piperidinyl (e.g., 1,4-piperidinyl).

In some embodiments, $R^9$ is heteroarylalkyl. In some embodiments, $R^9$ is $(CH_2)_n$-pyridyl, wherein n is 1, 2, 3, or 4. In some embodiments, $R^9$ is $(CH_2)$-pyridyl. In some embodiments, $R^9$ is 2-$(CH_2)$-pyridyl.

In some embodiments, the compound of Formula (II) is a compound of Formula (IIa):

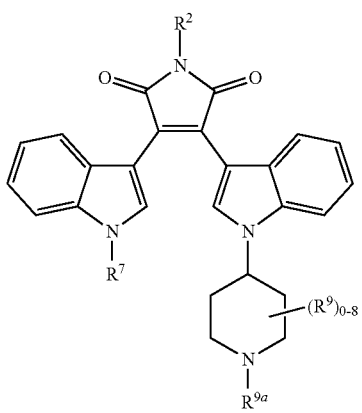

(IIa)

or a pharmaceutically acceptable salt, stereoisomer, racemate, or solvate thereof, wherein:
$R^2$ is hydrogen, —CH$_3$C(O), —NH$_2$, or hydroxyl;
$R^7$ is hydrogen or $C_1$-$C_4$ alkyl;
$R^9$ is $C_1$-$C_4$ alkyl, $C_1$-$C_4$ alkoxy, $C_1$-$C_4$ haloalkyl, halo, cyano, or nitro;
$R^{9a}$ is aryl, arylalkyl, heteroaryl, or heteroarylalkyl, each of which is optionally substituted with one or more $R^{10}$; and
each $R^{10}$ is independently halo, $C_1$-$C_4$ alkyl, $C_1$-$C_4$ alkoxy, $C_1$-$C_4$ haloalkyl, cyano, or nitro.

In some embodiments, each m is 0.
In some embodiments, $R^2$ is hydrogen.
In some embodiments, $R^7$ is $C_1$-$C_4$ alkyl (e.g., methyl or ethyl). In some embodiments, $R^7$ is methyl.
In some embodiments, $R^{9a}$ is heteroarylalkyl. In some embodiments, $R^{9a}$ is (CH$_2$)$_n$-pyridyl, wherein n is 1, 2, 3, or 4. In some embodiments, $R^{9a}$ is (CH$_2$)-pyridyl. In some embodiments, $R^{9a}$ is 2-(CH$_2$)-pyridyl.

In some embodiments, the compound of Formula (II) is a compound of Formula (IIb):

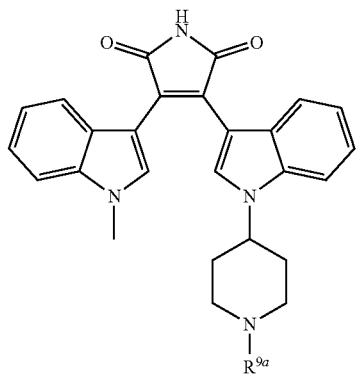

(IIb)

or a pharmaceutically acceptable salt, stereoisomer, racemate, or solvate thereof, wherein:
$R^{9a}$ is aryl, arylalkyl, heteroaryl, or heteroarylalkyl, each of which is optionally substituted with one or more $R^{10}$; and
each $R^{10}$ is independently halo, $C_1$-$C_4$ alkyl, $C_1$-$C_4$ alkoxy, $C_1$-$C_4$ haloalkyl, cyano, or nitro; and In some embodiments, $R^{9a}$ is heteroarylalkyl. In some embodiments, $R^{9a}$ is (CH$_2$)$_n$-pyridyl, wherein n is 1, 2, 3, or 4. In some embodiments, $R^{9a}$ is (CH$_2$)-pyridyl. In some embodiments, $R^{9a}$ is 2-(CH$_2$)-pyridyl.

In some embodiments, the PKC-β inhibitor of Formula (II) is a compound of Formula (IIc):

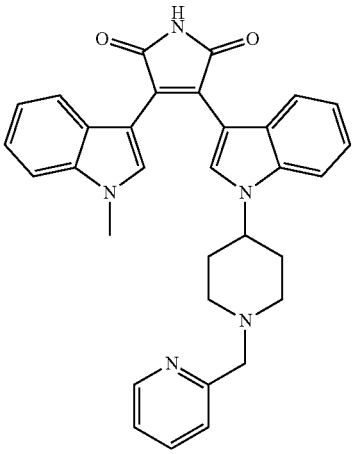

(IIc)

or a pharmaceutically acceptable salt, stereoisomer, racemate, or solvate thereof. In some embodiments, the PKC-β inhibitor (e.g., a compound of Formula (II)) is 3-(1-methyl-TH-indol-3-yl)-4-(1-(1-(pyridin-2-ylmethyl)piperidin-4-yl)-1H-indol-3-yl)-1H-pyrrole-2,5-dione (e.g., Formula (IIc)), e.g., LY-317615 or enzastaurin, or a pharmaceutically acceptable salt, stereoisomer, racemate, or solvate thereof. In some embodiments, the PKC-β inhibitor (e.g., a compound of Formula (II)) is enzastaurin hydrochloride.

In some embodiments, the PKC-β inhibitor is a compound of Formula (III):

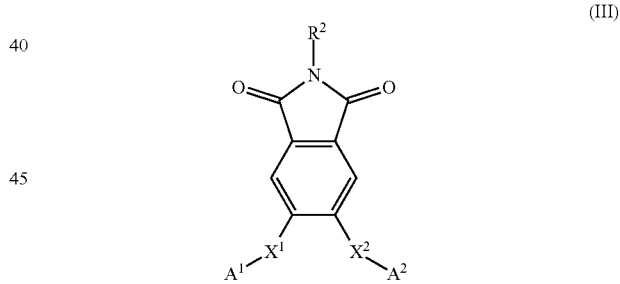

(III)

or a pharmaceutically acceptable salt, stereoisomer, racemate, or solvate thereof, wherein:
each of $X^1$ and $X^2$ is independently —O—, —NR$^4$—, or —S—;
each of $A^1$ and $A^2$ is independently aryl or heteroaryl, wherein each aryl or heteroaryl is optionally substituted with one or more $R^9$;
$R^2$ is hydrogen, —CH$_3$C(O), —NH$_2$, or hydroxyl;
$R^4$ is hydrogen or $C_1$-$C_4$ alkyl; and
$R^9$ is $C_1$-$C_4$ alkyl, $C_1$-$C_4$ alkoxy, $C_1$-$C_4$ haloalkyl, halo, cyano, or nitro.

In some embodiments, one of $X^1$ and $X^2$ is independently —NR$^4$—. In some embodiments, each of $X^1$ and $X^2$ is independently —NR$^4$—. In some embodiments, each of $X^1$ and $X^2$ is independently —NH—.

In some embodiments, one of $A^1$ and $A^2$ is independently aryl. In some embodiments, each of $A^1$ and $A^2$ is independently aryl. In some embodiments, each of $A^1$ and $A^2$ is independently phenyl. In some embodiments, each of $A^1$ and $A^2$ is independently phenyl substituted with 1 $R^9$. In some embodiments, each of $A^1$ and $A^2$ is independently phenyl substituted with 1 $R^9$ at the para position. In some embodiments, $R^9$ is halo (e.g., fluoro).

In some embodiments, the PKC-β inhibitor is a compound of Formula (IIIa):

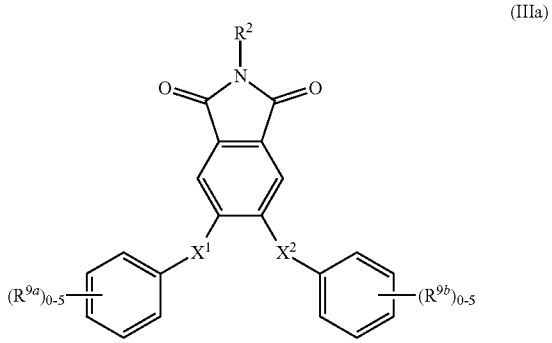

(IIIa)

or a pharmaceutically acceptable salt, stereoisomer, racemate, or solvate thereof, wherein:
each of $X^1$ and $X^2$ is independently —O—, —$NR^4$—, or —S—;
$R^2$ is hydrogen, —$CH_3C(O)$, —$NH_2$, or hydroxyl;
$R^4$ is hydrogen or $C_1$-$C_4$ alkyl; and
each of $R^{9a}$ and $R^{9b}$ is $C_1$-$C_4$ alkyl, $C_1$-$C_4$ alkoxy, $C_1$-$C_4$ haloalkyl, halo, cyano, or nitro.

In some embodiments, one of $X^1$ and $X^2$ is independently —$NR^4$—. In some embodiments, each of $X^1$ and $X^2$ is independently —$NR^4$—. In some embodiments, each of $X^1$ and $X^2$ is independently —NH—.

In some embodiments, each phenyl ring is substituted with 1 $R^{9a}$ and 1 $R^{9b}$. In some embodiments, each phenyl ring is substituted with 1 $R^{9a}$ and 1 $R^{9b}$ at the para position. In some embodiments, one of $R^{9a}$ and $R^{9b}$ is halo (e.g., fluoro). In some embodiments, each of $R^{9a}$ and $R^{9b}$ is halo (e.g., fluoro).

In some embodiments, the PKC-β inhibitor of Formula (III) is a compound of Formula (IIIb):

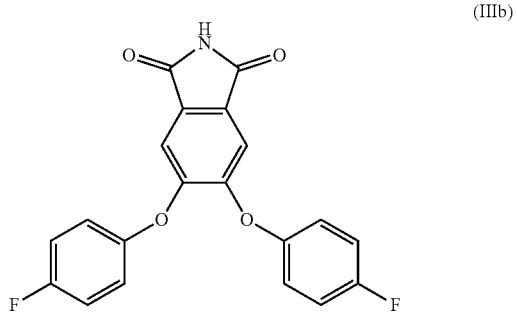 [SMILES: O=C1NC(=O)c2cc(Oc3ccc(F)cc3)c(Oc3ccc(F)cc3)cc21]

(IIIb)

or a pharmaceutically acceptable salt, stereoisomer, racemate, or solvate thereof. In some embodiments, the PKC-β inhibitor (e.g., a compound of Formula (III)) is 5,6-bis(4-fluorophenoxy)isoindoline-1,3-dione (e.g., Formula (IIb)), e.g., CGP 53353, CG 53353 or a pharmaceutically acceptable salt, stereoisomer, racemate, or solvate thereof.

Other PKCβ inhibitors disclosed herein include, e.g., a PKC R pseudosubstrate as described in Park et al (1999) Protein Kinase C-β Activates Tyrosinase by Phosphorylating Serine Residues in Its Cytoplasmic Domain. JBC Vol. 274, No. 23, Issue of June 4, pp. 16470-16478; and Park et al. (2004) The receptor for activated C-kinase-I (RACK-I) anchors activated PKC-β on melanosomes. Journal of Cell Science 117 (16) p. 3659. Exemplary PKC R pseudosubstrate includes e.g., an amino acid comprising the amino acid sequence Glu-Asp-Tyr-His-Ser-Leu-Tyr-Gln-Ser-His-Leu (SEQ ID NO: 1), an amino acid consisting essentially of the amino acid sequence Glu-Asp-Tyr-His-Ser-Leu-Tyr-Gln-Ser-His-Leu (SEQ ID NO:1); and an amino acid consisting of the amino acid sequence Glu-Asp-Tyr-His-Ser-Leu-Tyr-Gln-Ser-His-Leu (SEQ ID NO:1). PKC R pseudosubstrates with at least 75%, 80%, 85%, 90%, 95%, 99% homologous to SEQ ID NO: 1 are also contemplated.

III-1. Excipients

A. Organic Solvent and/or Penetration Enhancer

In some embodiments, the composition comprises an organic solvent and/or penetration enhancer. In some cases, the composition comprises the organic solvent. In some cases, the composition comprises the penetration enhancer. In some cases, the composition comprises the organic solvent and the penetration enhancer. The organic solvent may be a penetration enhancer. The penetration enhancer may be an organic solvent. Suitable solvents and/or penetration enhancers include, without limitation, a $C_{2-6}$ alkylene glycol (e.g., propylene glycol), a di-($C_{2-6}$ alkylene) glycol (e.g., dipropylene glycol), $C_{1-3}$ alkyl-$(OCH_2CH_2)_{1-5}$—OH (e.g., 2-(2-ethoxyethoxy)ethanol or Transcutol P), a polyethylene glycol (e.g., PEG200 and/or PEG400), glycerol, a fatty alcohol (e.g., octyldodecanol), a fatty ester (e.g., diisopropyl adipate, isopropyl myristate, medium-chain triglycerides, sorbitan monooleate, or the like), a fatty ether (e.g., Laureth-4), and combinations thereof. In some embodiments, the organic solvent and/or penetration enhancer comprises a $C_{2-6}$ alkylene glycol, $C_{1-3}$ alkyl-$(OCH_2CH_2)_{1-5}$—OH, a polyethylene glycol, glycerol, a fatty alcohol, a fatty ester, or a fatty ether, or combinations thereof.

In some embodiments, compositions herein comprise two or more organic solvents and/or penetration enhancers. For instance, in some embodiments, the composition comprises a first organic solvent and/or penetration enhancer, and a second organic solvent and/or penetration enhancer. In some cases, the first organic solvent and/or penetration enhancer comprises an organic solvent. In some cases, the first organic solvent and/or penetration enhancer comprises a penetration enhancer. In some cases, the first organic solvent and/or penetration enhancer is an organic solvent and a penetration enhancer. In some cases, the second organic solvent and/or penetration enhancer comprises an organic solvent. In some cases, the second organic solvent and/or penetration enhancer comprises a penetration enhancer. In some cases, the second organic solvent and/or penetration enhancer is an organic solvent and a penetration enhancer. In some embodiments, a composition herein comprises 2, 3, 4, or 5 organic solvents and/or penetration enhancers.

Non-limiting example organic solvents include a $C_{2-6}$ alkylene glycol (e.g., propylene glycol), a $C_{2-6}$ alcohol, a di-($C_{2-6}$ alkylene) glycol (e.g., dipropylene glycol), $C_{1-3}$ alkyl-$(OCH_2CH_2)_{1-5}$—OH (e.g., 2-(2-ethoxyethoxy)ethanol or Transcutol P), a polyethylene glycol (e.g., PEG200 and/or PEG400), glycerol, a fatty alcohol (e.g., octyldodecanol), a fatty ester (e.g., diisopropyl adipate, isopropyl myristate, medium-chain triglycerides, sorbitan monooleate, or the like), a fatty ether (e.g., Laureth-4), and combinations thereof. In some embodiments, the organic solvent comprises a $C_{2-6}$ alkylene glycol, $C_{1-3}$ alkyl-$(OCH_2CH_2)_{1-5}$—OH, a polyethylene glycol, a $C_{2-6}$ alcohol, a glycerol, a fatty alcohol, a fatty ester, or a fatty ether, or a combination of two or more thereof. In some embodiments, the solvent comprises a $C_{2-6}$ alkylene glycol, a $C_{2-6}$ alcohol, or $C_{1-3}$ alkyl-$(OCH_2CH_2)_{1-5}$—OH, or a combination thereof. In some embodiments, the solvent comprises a $C_{2-6}$ alcohol. In some embodiments, the solvent comprises a $C_{2-6}$ alkylene glycol. In some embodiments, the solvent comprises $C_{1-3}$ alkyl-$(OCH_2CH_2)_{1-5}$—OH. In some embodiments, the solvent comprises an $C_{2-6}$ alcohol and $C_{1-3}$ alkyl-$(OCH_2CH_2)_{1-5}$—OH. In some embodiments, the solvent comprises a mixture of a $C_{2-6}$ alcohol and a $C_{2-6}$ alkylene glycol. In some embodiments, the composition comprises a mixture of $C_{2-6}$ alcohol, a $C_{2-6}$ alkylene glycol and a $C_{1-3}$ alkyl-$(OCH_2CH_2)_{1-5}$—OH.

Non-limiting example penetration enhancers include $C_{2-6}$ alkylene glycol (e.g., propylene glycol), a $C_{2-6}$ alcohol, a di-$(C_{2-6}$ alkylene) glycol (e.g., dipropylene glycol), $C_{1-3}$ alkyl-$(OCH_2CH_2)_{1-5}$—OH (e.g., 2-(2-ethoxyethoxy)ethanol or Transcutol P), a polyethylene glycol (e.g., PEG200 and/or PEG400), glycerol, a fatty alcohol (e.g., octyldodecanol), a fatty ester (e.g., diisopropyl adipate, isopropyl myristate, medium-chain triglycerides, sorbitan monooleate, or the like), a fatty ether (e.g., Laureth-4), and combinations thereof. In some embodiments, the penetration enhancer comprises a $C_{2-6}$ alkylene glycol, $C_{1-3}$ alkyl-$(OCH_2CH_2)_{1-5}$—OH, a polyethylene glycol, a $C_{2-6}$ alcohol, a glycerol, a fatty alcohol, a fatty ester, or a fatty ether, or a combination of two or more thereof. In some embodiments, the penetration enhancer comprises a $C_{2-6}$ alkylene glycol, a $C_{2-6}$ alcohol, or $C_{1-3}$ alkyl-$(OCH_2CH_2)_{1-5}$—OH, or a combination thereof. In some embodiments, the penetration enhancer comprises a $C_{2-6}$ alcohol. In some embodiments, the penetration enhancer comprises a $C_{2-6}$ alkylene glycol. In some embodiments, the penetration enhancer comprises $C_{1-3}$ alkyl-$(OCH_2CH_2)_{1-5}$—OH. In some embodiments, the penetration enhancer comprises an $C_{2-6}$ alcohol and $C_{1-3}$ alkyl-$(OCH_2CH_2)_{1-5}$—OH. In some embodiments, the penetration enhancer comprises a mixture of a $C_{2-6}$ alcohol and a $C_{2-6}$ alkylene glycol. In some embodiments, the composition comprises a mixture of $C_{2-6}$ alcohol, a $C_{2-6}$ alkylene glycol and a $C_{1-3}$ alkyl-$(OCH_2CH_2)_{1-5}$—OH.

In some embodiments, the organic solvent and/or penetration enhancer comprises $C_{2-6}$ alkylene glycol and/or $C_{1-3}$ alkyl-$(OCH_2CH_2)_{1-5}$—OH. In some embodiments, the organic solvent and/or penetration enhancer comprises $C_{2-6}$ alkylene glycol. In some embodiments, the organic solvent and/or penetration enhancer comprises $C_{1-3}$ alkyl-$(OCH_2CH_2)_{1-5}$—OH. In some embodiments, the organic solvent and/or penetration enhancer comprises $C_{2-6}$ alkylene glycol and $C_{1-3}$ alkyl-$(OCH_2CH_2)_{1-5}$—OH. In some embodiments, the organic solvent and/or penetration enhancer comprises a mixture of $C_{2-6}$ alkylene glycol and $C_{1-3}$ alkyl-$(OCH_2CH_2)_{1-5}$—OH. In some embodiments, the composition comprises $C_{2-6}$ alkylene glycol and $C_{1-3}$ alkyl-$(OCH_2CH_2)_{1-5}$—OH.

In some embodiments, $C_{1-3}$ alkyl-$(OCH_2CH_2)_{1-5}$—OH is 2-(2-ethoxyethoxy)ethanol (e.g., Transcutol P). In some embodiments, the $C_{2-6}$ alkylene glycol is propylene glycol.

In some embodiments, the organic solvent and/or penetration enhancer comprises propylene glycol and/or 2-(2-ethoxyethoxy)ethanol. In some embodiments, the organic solvent and/or penetration enhancer comprises propylene glycol. In some embodiments, the organic solvent and/or penetration enhancer comprises 2-(2-ethoxyethoxy)ethanol. In some embodiments, the organic solvent and/or penetration enhancer comprises propylene glycol and 2-(2-ethoxyethoxy)ethanol. In some embodiments, the organic solvent and/or penetration enhancer comprises a mixture of propylene glycol and 2-(2-ethoxyethoxy)ethanol. In some embodiments, the composition comprises propylene glycol and 2-(2-ethoxyethoxy)ethanol.

In some embodiments, the organic solvent and/or penetration enhancer comprises $C_{2-6}$ alkylene glycol, $C_{1-3}$ alkyl-$(OCH_2CH_2)_{1-5}$—OH, or polyethylene glycol, or a combination or two or more thereof. In some embodiments, the organic solvent and/or penetration enhancer comprises $C_{2-6}$ alkylene glycol. In some embodiments, the organic solvent and/or penetration enhancer comprises $C_{1-3}$ alkyl-$(OCH_2CH_2)_{1-5}$—OH. In some embodiments the organic solvent and/or penetration enhancer comprises polyethylene glycol. In some embodiments, the organic solvent and/or penetration enhancer comprises $C_{2-6}$ alkylene glycol and $C_{1-3}$ alkyl-$(OCH_2CH_2)_{1-5}$—OH. In some embodiments, the organic solvent and/or penetration enhancer comprises $C_{1-3}$ alkyl-$(OCH_2CH_2)_{1-5}$—OH and polyethylene glycol. In some embodiments, the organic solvent and/or penetration enhancer comprises $C_{2-6}$ alkylene glycol and polyethylene glycol. In some embodiments, the organic solvent and/or penetration enhancer comprises $C_{2-6}$ alkylene glycol, $C_{1-3}$ alkyl-$(OCH_2CH_2)_{1-5}$—OH, and polyethylene glycol. In some embodiments, the organic solvent and/or penetration enhancer comprises a mixture of two or more of a $C_{2-6}$ alkylene glycol, $C_{1-3}$ alkyl-$(OCH_2CH_2)_{1-5}$—OH and polyethylene glycol.

In some embodiments, the organic solvent and/or penetration enhancer comprises a polyethylene glycol (PEG). In some embodiments, the polyethylene glycol comprises PEG200, PEG300, PEG400, PEG500, PEG600, PEG700, PEG800, or PEG900, or a combination thereof. In some embodiments, the polyethylene glycol comprises PEG-200 and/or PEG-400. In some embodiments, the polyethylene glycol comprises PEG200. In some embodiments, the polyethylene glycol comprises PEG400. In some embodiments, the polyethylene glycol comprises a mixture of PEG200 and PEG400. In some embodiments, the polyethylene glycol comprises PEG-200 and/or PEG-400. In some embodiments, the organic solvent and/or penetration enhancer comprises PEG200. In some embodiments, the organic solvent and/or penetration enhancer comprises PEG400. In some embodiments, the organic solvent and/or penetration enhancer comprises a mixture of PEG200 and PEG400. In some embodiments, the composition comprises PEG200. In some embodiments, the composition comprises PEG400. In some embodiments, the composition comprises a mixture of PEG200 and PEG400. In some embodiments the polyethylene glycol is Super Refined or "SR" polyethylene glycol.

In some embodiments, the organic solvent and/or penetration enhancer comprises a fatty alcohol. As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12-20, 14-20, 12-18, 14-18, or 16-18 carbons on average. Suitable fatty alcohols include, but are not limited to, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, lignoceryl alcohol, octyldodecanol, and mixtures thereof. In some embodiments, the organic solvent and/or penetration enhancer comprises one or more fatty alcohols selected from capric alcohol, lauryl alcohol, myristyl alcohol, cetyl alcohol, palmitoleyl alcohol, stearyl alcohol, oleyl alcohol, arachidyl alcohol, heneicosyl alcohol, behenyl alcohol, erucyl alcohol, and lignoceryl alcohol. In some embodiments, the organic solvent and/or penetration enhancer comprises octyldodecanol. In some embodiments, the composition comprises octyldodecanol.

In some embodiments, the organic solvent and/or penetration enhancer comprise a fatty ester. In some embodiments, the fatty ester is a glyceryl fatty ester, ethylene glycol monoester and diester of a fatty acid, propylene glycol monoester and diester of a fatty acid, a sorbitan ester, a $C_{1-6}$ alkyl ester of a fatty acid, or di-($C_{1-6}$ alkyl) ester of adipic acid, or a combination of two or more thereof.

In some embodiments, the fatty ester is a glyceride. In some embodiments, the glyceride is monoglyceride, diglyceride, or triglyceride. The glyceride may be optionally substituted with sulfonic acid groups, or pharmaceutically acceptable salts thereof. Suitable fatty acids for deriving glycerides of fatty acids include, but are not limited to, those described herein. In some embodiments, the glyceride is a mono-glyceride of a fatty acid having 12 to 18 carbon atoms. In some embodiments, the glyceride is a diglyceride of a fatty acid having 12 to 18 carbon atoms. In some embodiments, the glyceride is a triglyceride of a fatty acid having 12 to 18 carbon atoms (e.g., also referred herein as a medium-chain triglyceride). In some embodiments, the organic solvent and/or penetration enhancer includes a triglyceride of a fatty acid having 12 to 18 carbon atoms (e.g., also referred herein as a medium-chain triglyceride). In some embodiments, the composition includes a triglyceride of a fatty acid having 12 to 18 carbon atoms (e.g., also referred herein as a medium-chain triglyceride).

In some embodiments, the fatty ester is an ethylene glycol monoester of a fatty acid, a propylene glycol monoester of a fatty acid, or a $C_{1-6}$ alkyl ester of a fatty acid. In some embodiments, the fatty ester is an ethylene glycol monoester, a propylene glycol monoester, or a $C_{1-4}$ alkyl ester of a fatty acid. Suitable fatty acids for deriving any one of the ethylene glycol monoester, propylene glycol monoester, and the $C_{1-4}$ alkyl ester of fatty acids include, but are not limited to, those described herein. In some embodiments, the fatty ester is an ethylene glycol monoester, a propylene glycol monoester, or a $C_{1-4}$ alkyl ester of a fatty acid having 12 to 18 carbon atoms. Non-limiting examples of esters of a fatty acid include a laurate, a myristate, a palmitate, a stearate, and an oleate. In some embodiments, the fatty ester is isopropyl myristate. In some embodiments, the organic solvent and/or penetration enhancer comprises isopropyl myristate. In some embodiments, the composition comprises isopropyl myristate.

In some embodiments, the fatty ester is a sorbitan ester. Suitable fatty acids for deriving the sorbitan esters include, but are not limited to, those described herein. Suitable sorbitan esters include, but are not limited to, the Span™ series (available from Uniqema), which includes Span 20 (Sorbitan monolaurate), 40 (Sorbitan monopalmitate), 60 (sorbitan monostearate), 65 (sorbitan tristearate), 80 (sorbitan monooleate), and 85 (sorbitan trioleate). In some embodiments, the fatty ester is sorbitan monooleate. In some embodiments, the organic solvent and/or penetration enhancer comprises sorbitan monooleate. In some embodiments, the composition comprises sorbitan monooleate.

In some embodiments, the fatty ester is a di-($C_{1-4}$ alkyl) ester of adipic acid (i.e., an adipate) or di-($C_{1-4}$ alkyl) ester of sebacic acid (i.e., a sebacate). In some embodiments, the fatty ester is diisopropyl adipate. In some embodiments, the organic solvent and/or penetration enhancer comprises diisopropyl adipate. In some embodiments, the composition comprises diisopropyl adipate.

In some embodiments, the organic solvent and/or penetration enhancer comprises a fatty ether. In some embodiments, the organic solvent and/or penetration enhancer comprises a polyoxyethylene fatty ether. In some embodiments, the organic solvent and/or penetration enhancer comprises Laureth-4. In some embodiments, the composition comprises Laureth-4.

In some embodiments, the total amount of organic solvent and/or penetration enhancer present in the composition in an amount of from about 60% to about 99%, from about 80% to about 99%, from about 90-99%, or from about 95% to about 99% by weight. In some embodiments the total amount of organic solvent and/or penetration enhancer present in the composition in an amount of about 85% by weight. In some embodiments, the total amount of organic solvent and/or penetration enhancer present in the composition in an amount of about 90% by weight. In some embodiments, the total amount of organic solvent and/or penetration enhancer present in the composition in an amount of about 96% by weight.

In some embodiments, the organic solvent and/or penetration enhancer comprises 2-(2-ethoxyethoxy)ethanol. In some embodiments, the composition comprises 2-(2-ethoxyethoxy)ethanol. In some embodiments, 2-(2-ethoxyethoxy)ethanol is present in the composition in an amount of from about 40% to about 50%, from about 43% to about 49%, about 47-49%, or about 47-48% by weight. In some embodiments, 2-(2-ethoxyethoxy)ethanol is present in the composition in an amount of from about 40% to about 50%, from about 43% to about 49%, about 47-49%, or about 47-48% by weight. In some embodiments, 2-(2-ethoxyethoxy)ethanol is present in the composition in an amount of from about 40% to about 50% by weight. In some embodiments, 2-(2-ethoxyethoxy)ethanol is present in the composition in an amount of about 47-48% by weight.

In some embodiments, the organic solvent and/or penetration enhancer comprises propylene glycol. In some embodiments, the composition comprises propylene glycol. In some embodiments, propylene glycol is present in the composition in an amount of from about 8-30%, 9-22%, 18-22%, 19-21% or 19-20% by weight. In some embodiments, propylene glycol is present in the composition in an amount of from about 8-30%, 9-22%, 18-22%, 19-21% or 19-20% by weight. In some embodiments, propylene glycol is present in the composition in an amount of about 19-20% by weight.

In some embodiments, the organic solvent and/or penetration enhancer comprises polyethylene glycol. In some embodiments, the composition comprises polyethylene glycol. In some embodiments, polyethylene glycol is present in the composition in an amount of from about 2-45%, 3-24%, 3-14%, 13-15%, or about 13-14% by weight. In some embodiments, polyethylene glycol is present in the composition in an amount of from about 2-45%, 3-24%, 3-14%, 13-15%, or about 13-14% by weight. In some embodiments, polyethylene glycol is present in the composition in an amount of from about 10% to about 20% by weight. In some embodiments, polyethylene glycol is present in the composition in an amount of about 13-14% by weight.

In some embodiments, the organic solvent and/or penetration enhancer comprises propylene glycol and/or 2-(2-ethoxyethoxy)ethanol; wherein the total amount of the propylene glycol and/or 2-(2-ethoxyethoxy)ethanol present in the composition is an amount of from about 50% to about 80%, from about 50% to about 70%, or about 67% by weight. In some embodiments, the organic solvent and/or penetration enhancer is propylene glycol and/or 2-(2-ethoxyethoxy)ethanol; wherein the total amount of the propylene glycol and/or 2-(2-ethoxyethoxy)ethanol present in the composition is an amount of from 50% to 80%, from 50% to 70%, or about 67% by weight. In some embodiments, the organic solvent and/or penetration enhancer comprises propylene glycol and/or 2-(2-ethoxyethoxy)ethanol; wherein the total amount of the propylene glycol and/or 2-(2-ethoxyethoxy)ethanol present in the composition in an amount of from about 50% to about 70% by weight. In some embodiments, the organic solvent and/or penetration enhancer comprises propylene glycol and/or 2-(2-ethoxyethoxy)ethanol; wherein the total amount of the propylene glycol and/or 2-(2-ethoxyethoxy)ethanol present in the composition in an amount of about 67% by weight.

In some embodiments, the composition comprises propylene glycol and/or 2-(2-ethoxyethoxy)ethanol; wherein the total amount of the propylene glycol and/or 2-(2-ethoxyethoxy)ethanol present in the composition in an amount of from about 50% to about 80%, from about 50% to about 70%, or about 67% by weight. In some embodiments, the composition comprises propylene glycol and/or 2-(2-ethoxyethoxy)ethanol; wherein the total amount of the propylene glycol and/or 2-(2-ethoxyethoxy)ethanol present in the composition in an amount of from about 50% to about 70% by weight. In some embodiments, the composition comprises propylene glycol and/or 2-(2-ethoxyethoxy)ethanol; wherein the total amount of the propylene glycol and/or 2-(2-ethoxyethoxy)ethanol present in the composition in an amount of about 67% by weight.

In some embodiments, the organic solvent and/or penetration enhancer comprises a mixture of polyethylene glycol and 2-(2-ethoxyethoxy)ethanol; wherein the total amount of the mixture is present in the composition in an amount of from about 50% to about 80%, from about 50% to about 70%, or about 61% by weight. In some embodiments, the organic solvent and/or penetration enhancer comprises a mixture of polyethylene glycol and 2-(2-ethoxyethoxy)ethanol; wherein the total amount of the mixture is present in the composition in an amount of from about 50% to about 80%, from about 50% to about 70%, or about 61% by weight. In some embodiments, the organic solvent and/or penetration enhancer comprises a mixture of polyethylene glycol and 2-(2-ethoxyethoxy)ethanol; wherein the total amount of the mixture is present in the composition in an amount of from about 50% to about 70% by weight. In some embodiments, the organic solvent and/or penetration enhancer comprises a mixture of polyethylene glycol and 2-(2-ethoxyethoxy)ethanol; wherein the total amount of the mixture is present in the composition in an amount of about 61% by weight.

In some embodiments, the composition comprises a mixture of polyethylene glycol and 2-(2-ethoxyethoxy)ethanol; wherein the total amount of the mixture is present in the composition in an amount of from about 50% to about 80%, from about 50% to about 70%, or about 61% by weight. In some embodiments, the composition comprises a mixture of polyethylene glycol and 2-(2-ethoxyethoxy)ethanol; wherein the total amount of the mixture is present in the composition in an amount of from about 50% to about 80%, from about 50% to about 70%, or about 61% by weight. In some embodiments, the composition comprises a mixture of polyethylene glycol and 2-(2-ethoxyethoxy)ethanol; wherein the total amount of the mixture is present in the composition in an amount of from about 50% to about 70% or about 61% by weight. In some embodiments, the composition comprises a mixture of polyethylene glycol and 2-(2-ethoxyethoxy)ethanol; wherein the total amount of the mixture is present in the composition in an amount of from about 50% to about 70% by weight. In some embodiments, the composition comprises a mixture of polyethylene glycol and 2-(2-ethoxyethoxy)ethanol; wherein the total amount of the mixture is present in the composition in an amount of about 61% by weight.

In some embodiments, the organic solvent and/or penetration enhancer comprises a mixture of propylene glycol, polyethylene glycol and 2-(2-ethoxyethoxy)ethanol; wherein the total amount of the mixture is present in the composition in an amount of from about 50% to about 100%, from about 70% to about 90%, or about 81% by weight. In some embodiments, the organic solvent and/or penetration enhancer comprises a mixture of propylene glycol, polyethylene glycol and 2-(2-ethoxyethoxy)ethanol; and the total amount of the mixture is present in the composition in an amount of from about 50% to about 100%, from about 70% to about 90%, or about 81% by weight. In some embodiments, the organic solvent and/or penetration enhancer comprises a mixture of propylene glycol, polyethylene glycol and 2-(2-ethoxyethoxy)ethanol; and the total amount of the mixture is present in the composition in an amount of from about 60% to about 90% or about 81% by weight. In some embodiments, the organic solvent and/or penetration enhancer comprises a mixture of propylene glycol, polyethylene glycol and 2-(2-ethoxyethoxy)ethanol; and the total amount of the mixture is present in the composition in an amount of from about 60% to about 90% by weight. In some embodiments, the organic solvent and/or penetration enhancer comprises a mixture of propylene glycol, polyethylene glycol and 2-(2-ethoxyethoxy)ethanol; and the total amount of the mixture is present in the composition in an amount of about 81% by weight.

In some embodiments, the composition comprises a mixture of propylene glycol, polyethylene glycol and 2-(2-ethoxyethoxy)ethanol; wherein the total amount of the mixture is present in the composition in an amount of from about 50% to about 100%, from about 70% to about 90%, or about 81% by weight. In some embodiments, the composition comprises a mixture of propylene glycol, polyethylene glycol and 2-(2-ethoxyethoxy)ethanol; and the total amount of the mixture is present in the composition in an amount of from about 50% to about 100%, from about 70% to about 90%, or about 81% by weight. In some embodiments, the composition comprises a mixture of propylene glycol, polyethylene glycol and 2-(2-ethoxyethoxy)ethanol; and the total amount of the mixture is present in the composition in an amount of from about 60% to about 90% or about 81% by weight. In some embodiments, the composition comprises a mixture of propylene glycol, polyethylene glycol and 2-(2-ethoxyethoxy)ethanol; and the total amount of the mixture is present in the composition in an amount of from about 60% to about 90% by weight. In some embodiments, the composition comprises a mixture of propylene glycol, polyethylene glycol and 2-(2-ethoxyethoxy)ethanol; and the total amount of the mixture is present in the composition in an amount of about 81% by weight.

In some embodiments, the organic solvent and/or penetration enhancer comprises propylene glycol and 2-(2-ethoxyethoxy)ethanol. In some embodiments, the composition comprises propylene glycol and 2-(2-ethoxyethoxy) ethanol. In some embodiments, propylene glycol is present in an amount of from about 10% to about 30% by weight of the composition; and 2-(2-ethoxyethoxy)ethanol is present in an amount of from about 40% to about 50% by weight or the composition. In some embodiments, propylene glycol is present in an amount of about 20% by weight of the composition; and 2-(2-ethoxyethoxy)ethanol is present in an amount of about 47% by weight of the composition.

In some embodiments, the organic solvent and/or penetration enhancer comprises polyethylene glycol and 2-(2-ethoxyethoxy)ethanol. In some embodiments, the composition comprises polyethylene glycol and 2-(2-ethoxyethoxy) ethanol. In some embodiments, polyethylene glycol is present in an amount of from about 10% to about 20% by weight of the composition; and 2-(2-ethoxyethoxy)ethanol is present in an amount of from about 40% to about 50% by weight of the composition. In some embodiments, polyethylene glycol is present in an amount of about 14% by weight of the composition; and 2-(2-ethoxyethoxy)ethanol is present in an amount of about 47% by weight of the composition.

In some embodiments, the organic solvent and/or penetration enhancer comprises propylene glycol, polyethylene glycol, and 2-(2-ethoxyethoxy)ethanol. In some embodiments, the composition comprises propylene glycol, polyethylene glycol, and 2-(2-ethoxyethoxy)ethanol. In some embodiments, propylene glycol is present at about 10% to about 30% by weight of the composition; polyethylene glycol is present in an amount of from about 10% to about 20% by weight of the composition; and 2-(2-ethoxyethoxy) ethanol is present in an amount of from about 40% to about 50% by weight of the composition. In some embodiments, propylene glycol is present in an amount of about 20% per weight of the composition; polyethylene glycol is present in an amount of about 14% by weight of the composition; and 2-(2-ethoxyethoxy)ethanol is present in an amount of about 47% by weight of the composition.

In some embodiments, propylene glycol is a super refined propylene glycol.

In some embodiments, polyethylene glycol is a super refined polyethylene glycol.

In some embodiments, 2-(2-ethoxyethoxy)ethanol has a purity of at least about 95%, 96%, 97%, 98%, or 99%. In some embodiments, 2-(2-ethoxyethoxy)ethanol is Transcutol HP. In some embodiments, 2-(2-ethoxyethoxy)ethanol is Transcutol HP having a purity of at least about 98% or 99%, e.g., about >99.90%.

In some embodiments, the organic solvent and/or penetration enhancer comprises a $C_{2-6}$ alcohol. In some embodiments, the composition comprises a $C_{2-6}$ alcohol. In some embodiments, the $C_{2-6}$ alcohol is selected from the group consisting of ethanol, propanol, isopropanol, n-butanol, isobutanol, 2-butanol, tert-butanol, and glycerol, and combinations of two or more thereof. In some embodiments, the $C_{2-6}$ alcohol is glycerol. In some embodiments the composition comprises a $C_{2-6}$ alcohol in an amount of from about 5% to about 30%, from about 5% to about 20%, or about 15% by weight. In some embodiments, $C_{2-6}$ alcohol is present in the composition in an amount of from about 5% to about 20% by weight. In some embodiments, $C_{2-6}$ alcohol is present in the composition in an amount of about 15% by weight.

In some embodiments, the composition comprises glycerol in an amount of about 12-24%, 14-20%, 13-17%, 14-16%, or 14-15% by weight. In some embodiments, glycerol is present in an amount of from about 10% to about 20% by weight. In some embodiments, glycerol is present in an amount of about 14-15% by weight.

In some embodiments, the composition comprises ethanol in the composition in an amount of about 3-12%, 4-6%, or 9-11% by weight. In some embodiments, ethanol is present in an amount of from about 5% by weight. In some embodiments, ethanol is present in an amount of about 10% by weight.

In some embodiments, the composition does not include $C_{2-6}$ alcohol. In some embodiments, the composition does not include ethanol. In some embodiments that composition does not include glycerol.

B. Antioxidant

In some embodiments, the composition comprises an antioxidant. In some embodiments, the composition does not include an antioxidant. In some embodiments, compositions as described herein comprise two or more antioxidants. For instance, in some embodiments, the composition comprises a first antioxidant, and a second antioxidant. In some embodiments, a composition as described herein comprises 2, 3, 4, or 5 antioxidants.

Non-limiting example antioxidants include butylated hydroxytoluene (BHT), butylated hydroxyanisole (BHA), propyl gallate, ascorbic acid, alphatocopheryl acetate, and ascorbyl palmitate. In some embodiments, the antioxidant comprises butylated hydroxytoluene. In some embodiments, the antioxidant comprises butylated hydroxyanisole. In some embodiments, the antioxidant comprises propyl gallate. In some embodiments, the antioxidant comprises a mixture of butylated hydroxytoluene and butylated hydroxyanisole.

In some embodiments, the total amount of antioxidant is present in the composition in an amount of from about 0.01% to about 1% by weight of the composition. In some embodiments, the total amount of antioxidant is present in an amount of from about 0.01% to about 1%, from about 0.01% to about 0.5%, or about 0.2% by weight. In some embodiments, the any one antioxidant is present in the composition in an amount of from about 0.01% to about 1% by weight. In some embodiments, any one antioxidant is present in the composition in an amount of from about 0.1% to about 1% by weight. In some embodiments, any one antioxidant is present in the composition in an amount of about 0.1% by weight. In some embodiments, the antioxidant is butylated hydroxytoluene in an amount of from about 0.01% to about 1%, or about 0.1% by weight of the composition. In some embodiments, the antioxidant comprises butylated hydroxytoluene in an amount of from about 0.01% to about 1% by weight of the composition. In some embodiments, the antioxidant comprises butylated hydroxytoluene in an amount of about 0.1% by weight of the composition. In some embodiments, the antioxidant comprises butylated hydroxyanisole in an amount of from about 0.01% to about 1% or about 0.1% by weight of the composition. In some embodiments, the antioxidant comprises butylated hydroxyanisole in an amount of about 0.1% by weight of the composition. In some embodiments, the antioxidant comprises propyl gallate in an amount of from about 0.01% to about 0.5% or about 0.1% by weight of the composition. In some embodiments, the antioxidant comprises propyl gallate in an amount of from about 0.01% to about 0.5% by weight of the composition. In some embodiments, the antioxidant comprises propyl gallate in an amount of about 0.10% by weight of the composition. In some embodiments, the antioxidant comprises a mixture of butylated hydroxytoluene and butylated hydroxyanisole, each of which is present in an amount of from about 0.01% to about 1% or about 0.1% by weight of the composition. In some embodiments, the antioxidant comprises a mixture of butylated hydroxytoluene and butylated hydroxyanisole, each of which is present in an amount of from about 0.01% to about 1% by weight of the composition. In some embodiments, the antioxidant comprises a mixture of butylated hydroxytoluene and butylated hydroxyanisole, each of which is present in an amount of about 0.1% by weight of the composition.

C. Alcohol and Humectants

In some embodiments, the composition comprises an additional agent such as an alcohol or humectant. Suitable agents include, but are not limited to a $C_{2-6}$ alcohol, a $C_{2-6}$ alkylene glycol (e.g., propylene glycol), a di-($C_{2-6}$ alkylene) glycol (e.g., dipropylene glycol), $C_{1-3}$ alkyl-$(OCH_2CH_2)_{1-5}$—OH (e.g., 2-(2-ethoxyethoxy)ethanol or Transcutol P), a polyethylene glycol (e.g., PEG200 and/or PEG400), glycerol, a fatty alcohol (e.g., octyldodecanol), a fatty ester (e.g., diisopropyl adipate, isopropyl myristate, medium-chain triglycerides, sorbitan monooleate, or the like), a fatty ether (e.g., Laureth-4), and combinations thereof. In some embodiments, the agent comprises a $C_{2-6}$ alkylene glycol, $C_{1-3}$ alkyl-$(OCH_2CH_2)_{1-5}$—OH, a polyethylene glycol, a $C_{2-6}$ alcohol, a glycerol, a fatty alcohol, a fatty ester, a fatty ether, and combinations thereof.

In some embodiments, the agent comprises a $C_{2-6}$ alcohol, a $C_{2-6}$ alkylene glycol, or $C_{1-3}$ alkyl-$(OCH_2CH_2)_{1-5}$—OH, or a combination thereof. In some embodiments, the agent comprises a $C_{2-6}$ alcohol. In some embodiments, the agent comprises a $C_{2-6}$ alkylene glycol. In some embodiments, the agent comprises $C_{1-3}$ alkyl-$(OCH_2CH_2)_{1-5}$—OH. In some embodiments, the agent comprises an $C_{2-6}$ alcohol and $C_{1-3}$ alkyl-$(OCH_2CH_2)_{1-5}$—OH. In some embodiments, the agent comprises a mixture of a $C_{2-6}$ alcohol and a $C_{2-6}$ alkylene glycol. In some embodiments, the composition comprises a mixture of $C_{2-6}$ alcohol, a $C_{2-6}$ alkylene glycol and a $C_{1-3}$ alkyl-$(OCH_2CH_2)_{1-5}$—OH.

In some embodiments, the additional agent is a $C_{2-6}$ alcohol. In some embodiments, the $C_{2-6}$ alcohol is selected from the group consisting of ethanol, propanol, isopropanol, n-butanol, isobutanol, 2-butanol, tert-butanol, glycerol, and combinations thereof. In some embodiments, the $C_{2-6}$ alcohol is glycerol.

In some embodiments, the composition does not include $C_{2-6}$ alcohol. In some embodiments, the composition does not include ethanol. In some embodiments that composition does not include glycerol.

In some embodiments, the composition includes one or more agents, alcohols or humectants. In some embodiments the agent is a $C_{2-6}$ alcohol in an amount of from about 5% to 20%, or about 15% by weight of the composition. In some embodiments, $C_{2-6}$ alcohol is present in the composition in an amount of from 5% to 20% by weight of the composition. In some embodiments, $C_{2-6}$ alcohol is present in an amount of about 15% by weight of the composition.

In some embodiments, the composition comprises glycerol in an amount of about 12-24%, 14-20%, 13-17%, 14-16%, or 14-15% by weight. In some embodiments, glycerol is present in an amount of from about 10% to about 20% by weight. In some embodiments, glycerol is present in an amount of about 14-15% by weight.

In some embodiments, the composition comprises ethanol in the composition in an amount of about 3-12%, 4-6%, or 9-11% by weight. In some embodiments, ethanol is present in an amount of from about 5% by weight. In some embodiments, ethanol is present in an amount of about 10% by weight.

In some embodiments, the composition does not include $C_{2-6}$ alcohol. In some embodiments, the composition does not include ethanol. In some embodiments that composition does not include glycerol.

D. Gelling Agent

In some embodiments, the composition comprises a gelling agent. In some cases, the gelling agent is a polymer thickener). In some embodiments, the gelling agent increases the viscosity of the composition. In some embodiments, compositions herein comprise two or more gelling agents. For instance, in some embodiments, the composition comprises a first gelling agent, and a second gelling agent. In some embodiments, a composition herein comprises 2, 3, 4, or 5 gelling agents.

Gelling agents include, for example, hydrophilic and hydroalcoholic gelling agents frequently used in the cosmetic and pharmaceutical industries. Further non-limiting examples include a Carbopol (also referred to as a carbomer), carboxymethyl cellulose, ethylcellulose, gelatin, hydroxyethyl cellulose, hydroxypropyl cellulose, magnesium aluminum silicate (Veegum), methylcellulose, a poloxamer (Pluronics), polyvinyl alcohol, sodium alginate, tragacanth, xanthan gum, Sepineo P600, a polyethylene glycol having an average molecular weight of at least about 2500 Da, and a combination of two or more thereof. In some embodiments, the gelling agent comprises Sepineo P600. In some embodiments, the gelling agent is Sepineo P600. In some embodiments, the gelling agent comprises a polyethylene glycol having an average molecular weight of from about 2500 to 3500 Da (e.g., PEG3350). In some embodiments, the gelling agent is a polyethylene glycol having an average molecular weight of from about 2500 to 3500 Da (e.g., PEG3350). In some embodiments, the gelling agent comprises hydroxypropyl cellulose. In some embodiments, the gelling agent is hydroxypropyl cellulose.

In some embodiments, the gelling agent comprises hydroxypropyl cellulose. In some embodiments, the composition comprises hydroxypropyl cellulose. In some cases, hydroxypropyl cellulose has an average molecular weight of about 40,000 Dalton (Da), about 80,000 Da, about 100,000 Da, about 140,000 Da, about 180,000 Da, about 280,000 Da, about 370,000 Da, about 700,000 Da, about 850,000 Da, about 1,000,000 Da, about 1,150,000 Da, or about 2,500,000 Da. In some embodiments, the hydroxypropyl cellulose has an average molecular weight of about 140,000 Da, about 180,000 Da, about 280,000 Da, about 370,000 Da, about 700,000 Da, about 850,000 Da, about 1,000,000 Da, or about 1,150,000 Da. In some embodiments, the hydroxypropyl cellulose has an average molecular weight of about 700,000 Da, about 850,000 Da, about 1,000,000 Da, or about 1,150,000 Da. In some embodiments, the hydroxypropyl cellulose has an average molecular weight of from about 700,000 Da to about 1,150,000 Da.

Hydroxypropyl cellulose (HPC) includes, for example Nisso SSL, Nisso SL, Nisso L, Nisso LM, Nisso LMM, Nisso M, Nisso H, Nisso VH, Klucel ELF, Klucel EF, Klucel LF, Klucel JF, Klucel GF, Klucel MF, and Klucel HF.

Nisso SSL has an average molecular weight of about 40,000 Da; Nisso SL has an average molecular weight of about 100,000 Da; Nisso L has an average molecular weight of about 140,000 Da; Nisso LM has an average molecular weight of about 180,000 Da; Nisso LMM has an average molecular weight of about 280,000 Da; Nisso M has an average molecular weight of about 700,000 Da; Nisso H has an average molecular weight of about 1,000,000 Da; and Nisso VH has an average molecular weight of about 2,500,000 Da. Suitable particle sizes of Nisso HPC (i.e., Nisso SSL, Nisso SL, Nisso L, Nisso LM, Nisso LMM, Nisso M, Nisso H, and Nisso VH) in the composition include regular powder (e.g., 40 mesh), fine powder (e.g., 100 mesh), and super fine powder (e.g., 300 mesh). See Technical date sheets of Nisso HPCs, the entirety of which is incorporated herein by reference.

In some embodiments, the hydroxypropyl cellulose is Nisso L, Nisso LM, Nisso LMM, Nisso M, or Nisso H. In some embodiments, the hydroxypropyl cellulose is Nisso LM, Nisso LMM, Nisso M, or Nisso H. In some embodiments, the hydroxypropyl cellulose is Nisso LMM, Nisso M, or Nisso H. In some embodiments, the hydroxypropyl cellulose is Nisso M or Nisso H. In some embodiments, the hydroxypropyl cellulose is Nisso M. In some embodiments, the hydroxypropyl cellulose is Nisso H.

Klucel ELF has an average molecular weight of about 40,000 Da; Klucel EF has an average molecular weight of about 80,000 Da; Klucel LF has an average molecular weight of about 95,000 Da; Klucel JF has an average molecular weight of about 140,000 Da; Klucel GF has an average molecular weight of about 370,000 Da; Klucel MF has an average molecular weight of about 850,000 Da; and Klucel HF has an average molecular weight of about 1,150,000 Da. Suitable particle sizes of Klucel HPC in the composition include regular grade and fine grade. See Technical date sheets of Klucel HPC products, the entirety of which is incorporated herein by reference.

In some embodiments, the hydroxypropyl cellulose is Klucel JF, Klucel GF, Klucel MF, or Klucel HF. In some embodiments, the hydroxypropyl cellulose is Klucel GF, Klucel MF, or Klucel HF. In some embodiments, the hydroxypropyl cellulose is Klucel GF. In some embodiments, the hydroxypropyl cellulose is Klucel MF. In some embodiments, the hydroxypropyl cellulose is Klucel HF.

When the gelling agent is present in the composition, in some embodiments, the composition has a viscosity of from about 5,000 cP to about 100,000 cP. When the gelling agent is present, in some embodiments, the composition has a viscosity of from about 5,000 cP to about 50,000 cP. When the gelling agent is present, in some embodiments, the composition has a viscosity of from about 5,000 cP to about 40,000 cP. When the gelling agent is present, in some embodiments, the composition has a viscosity of from about 5,000 cP to about 30,000 cP. When the gelling agent is present, in some embodiments, the composition has a viscosity of from about 10,000 cP to about 30,000 cP. When the gelling agent is present, in some embodiments, the composition has a viscosity of from about 15,000 cP to about 30,000 cP. When the gelling agent is present, in some embodiments, the composition has a viscosity of from about 20,000 cP to about 30,000 cP.

When the hydroxypropyl cellulose is present, in some embodiments, the composition has a viscosity of from about 5,000 cP to about 100,000 cP. When the hydroxypropyl cellulose is present, in some embodiments, the composition has a viscosity of from about 5,000 cP to about 50,000 cP. When the hydroxypropyl cellulose is present, in some embodiments, the composition has a viscosity of from about 5,000 cP to about 40,000 cP. When the hydroxypropyl cellulose is present, in some embodiments, the composition has a viscosity of from about 5,000 cP to about 30,000 cP. When the hydroxypropyl cellulose is present, in some embodiments, the composition has a viscosity of from about 10,000 cP to about 30,000 cP. When the hydroxypropyl cellulose is present, in some embodiments, the composition has a viscosity of from about 15,000 cP to about 30,000 cP. When the hydroxypropyl cellulose is present, in some embodiments, the composition has a viscosity of from about 20,000 cP to about 30,000 cP.

In some embodiments, the gelling agent is present in the composition in an amount of from about 0.5% to about 30% by weight, while the composition has a viscosity of from about 5,000 cP to about 100,000 cP. In some embodiments, the gelling agent is present in an amount of from about 0.5% to about 30% by weight, while the composition has a viscosity of from about 5,000 cP to about 50,000 cP. In some embodiments, the gelling agent is present in an amount of from about 0.5% to about 30% by weight, while the composition has a viscosity of from about 5,000 cP to about 40,000 cP. In some embodiments, the gelling agents are present in an amount of from about 0.5% to about 30% by weight, while the composition has a viscosity of from about 5,000 cP to about 30,000 cP. In some embodiments, the gelling agents are present in an amount of from about 0.5% to about 30% by weight, while the composition has a viscosity of from about 10,000 cP to about 30,000 cP. In some embodiments, the gelling agents are present in an amount of from about 0.5% to about 30% by weight, while the composition has a viscosity of from about 15,000 cP to about 30,000 cP. In some embodiments, the gelling agents are present in an amount of from about 0.5% to 30% by weight, while the composition has a viscosity of from about 20,000 cP to about 30,000 cP.

In some embodiments, the gelling agent comprises hydroxypropyl cellulose (HPC). In some embodiments, the composition comprises hydroxypropyl cellulose. In some embodiments, the hydroxypropyl cellulose is present in an amount of from about 0.5% to about 5% to about 30% by weight, and the composition has a viscosity of from about 5,000 cP to about 100,000 cP. When a hydroxypropyl cellulose having an average molecular weight of less than about 700,000 Da is used, in some embodiments, the hydroxypropyl cellulose is present in an amount of about 5% to about 30% by weight, and the composition has a viscosity of from about 5,000 cP to about 100,000 cP. In some embodiments, the hydroxypropyl cellulose is present in an amount of from about 0.5% to about 5%, and the composition has a viscosity of from about 5,000 cP to about 50,000 cP. In some embodiments, the hydroxypropyl cellulose is present in an amount of from about 0.5% to about 5%, and the composition has a viscosity of from about 5,000 cP to about 40,000 cP. In some embodiments, the hydroxypropyl cellulose is present in an amount of from about 0.5% to about 5%, and the composition has a viscosity of from about 5,000 cP to about 30,000 cP. In some embodiments, the hydroxypropyl cellulose is present in an amount of from about 0.5% to about 4%, and the composition has a viscosity of from about 10,000 cP to about 30,000 cP. In some embodiments, the hydroxypropyl cellulose is present in an amount of from about 0.5% to about 4%, and the composition has a viscosity of from about 15,000 cP to about 30,000 cP. In some embodiments, the hydroxypropyl cellulose is present in an amount of from about 0.5% to about 4%, and the composition has a viscosity of from about 20,000 cP to about 30,000 cP.

In some embodiments, the hydroxypropyl cellulose having an average molecular weight of from about 700,000 Da to about 1,150,000 Da is present in the composition in an amount of from about 0.5% to about 2% by weight. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 5,000 cP to about 50,000 cP. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 5,000 cP to about 40,000 cP. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 5,000 cP to about 30,000 cP. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 10,000 cP to about 30,000 cP. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 15,000 cP to about 30,000 cP. In some embodiments, the hydroxypropyl cellulose having an average molecular weight of from about 700,000 Da to about 1,150,000 Da is present in the composition in an amount of from about 0.5% to about 2% by weight, and the composition has a viscosity of from about 20,000 cP to about 30,000 cP.

In some embodiments, the hydroxypropyl cellulose having an average molecular weight of from about 700,000 Da to about 1,150,000 Da is present in the composition in an amount of about 3% by weight.

III-2. Apparent pH Value

When the composition is a non-aqueous formulation, the pH value of the composition is an apparent pH value. When the composition includes water, the composition includes substantial amounts of other excipients (e.g., $C_{2-6}$ alcohol, organic solvents and/or penetration enhancers, a gelling agent). Therefore, the pH value of a partially aqueous solutions can be regarded only as an apparent pH value. According to US Pharmacopeia (USP) chapter <791>, the apparent pH value of an non-aqueous or a partially aqueous solution is anticipated for variability, which may be up to approximately 1 pH unit. See USP chapter <791>, the entirety of which is incorporated herein.

In some embodiments, when a pH adjuster is absent from a composition, the composition has an apparent pH value of from about 7.5 to about 9.5. In some embodiments, when a pH adjuster is absent from a composition, the composition has an apparent pH value of from about 7.5 to about 8.5. In some embodiments, when a pH adjuster is absent from a composition, the composition has an apparent pH value of from about 8.5 to about 9.5. In some embodiments, when a pH adjuster is absent from a composition, the composition has an apparent pH value of about 8. In some embodiments, when a pH adjuster is absent from a composition, the composition has an apparent pH value of about 9.

In some embodiments, when a pH adjuster is present in a composition, the composition has an apparent pH value of no more than about 7. In some embodiments, when a pH adjuster is present in a composition, the composition has an apparent pH value of from about 5 to about 7 or from about 6 to about 7. In some embodiments, when a pH adjuster is present in a composition, the composition has an apparent pH value of from about 6 to about 7.

III-3. Compound

In any one of the compositions as described herein, the compound is a PK inhibitor, without limitation, such as ruboxistaurin free base or a ruboxistaurin salt (e.g., ruboxistaurin mesylate monohydrate), in some instances represented by either of the formulas:

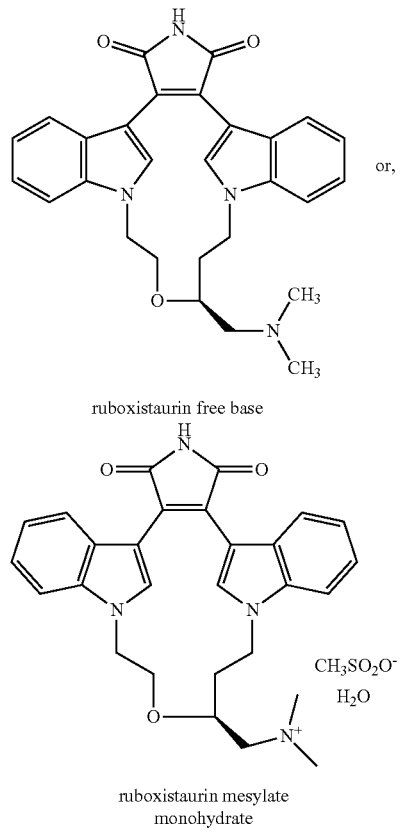

ruboxistaurin free base ruboxistaurin mesylate monohydrate

In any one of the compositions as described herein, the compound can be an acceptable salt of ruboxistaurin free base, ruboxistaurin mesylate monohydrate, or a mixture thereof. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

In any one of the compositions as described herein, a PK inhibitor, without limitation, such as ruboxistaurin free base or a ruboxistaurin salt (e.g., ruboxistaurin mesylate monohydrate) can be in a solvate or hydrate form, or a mixture thereof.

In any one of the compositions described herein, the ruboxistaurin can be a free base (FB) or a salt such as ruboxistaurin mesylate monohydrate (MM) or a mixture thereof.

In some embodiments, the PK inhibitor, without limitation, such as ruboxistaurin free base or a ruboxistaurin salt (e.g., ruboxistaurin mesylate monohydrate) is present in the composition in an amount of from about 0.08% to 10.0%, from 0.5% to 5.0%, from 0.5% to 2.0%, or about 1.0% by weight. In some embodiments, the PK inhibitor, without limitation, such as ruboxistaurin free base or a ruboxistaurin salt (e.g., ruboxistaurin mesylate monohydrate) is present in an amount of from about 0.5% to 5.0%, from 0.5% to 2.0%, or about 1.0% by weight. In some embodiments, the PK inhibitor, without limitation, such as ruboxistaurin free base or a ruboxistaurin salt (e.g., ruboxistaurin mesylate monohydrate) is present in an amount of about 0.5%, 0.6%, 0.7%, 0.8%, 0.9% or 1.0% of the composition. In some embodiments, the PK inhibitor, without limitation, such as ruboxistaurin free base or a ruboxistaurin salt (e.g., ruboxistaurin mesylate monohydrate) is present in an amount of from about 0.5% to 2.0%, or about 0.8% by weight. In some embodiments, the compound is present in an amount of about 0.8% by weight. The composition may be formulated at 0.1% w/w, 0.12% w/w, or 0.8% w/w ruboxistaurin mesylate monohydrate, formulated 0.08% w/w, 0.1% w/w, or 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% ruboxistaurin free base or a salt thereof, for administration twice daily, for about 12 weeks. In a non-limiting embodiment, the composition is formulated at 0.64% ruboxistaurin free base or a salt thereof, for administration twice daily, for about 4 to about 8 weeks. In a non-limiting embodiment, the composition is formulated at 0.8% ruboxistaurin mesylate monohydrate or a salt thereof, for administration twice daily, for about 12 weeks. In a non-limiting embodiment, the composition is formulated at 0.8% ruboxistaurin mesylate monohydrate or a salt thereof, for administration twice daily, for about 4 to about 8 weeks.

I-4. Embodiments

In some embodiments the composition comprises a PK inhibitor, without limitation, such as ruboxistaurin free base or a ruboxistaurin salt (e.g., ruboxistaurin mesylate monohydrate) and one or more excipients selected from: a) an organic solvent and/or penetration enhancer (e.g., a $C_{2-6}$ alkylene glycol, $C_{1-3}$ alkyl-$(OCH_2CH_2)_{1-5}$—OH; b) an antioxidant; c) an alcohol; and d) a gelling agent. In some embodiments the composition comprises the PK inhibitor, without limitation, such as ruboxistaurin free base or a ruboxistaurin salt (e.g., ruboxistaurin mesylate monohydrate), and two or more excipients selected from: a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; c) an alcohol; and d) a gelling agent. In some embodiments the composition comprises the PK inhibitor, without limitation, such as ruboxistaurin free base or a ruboxistaurin salt (e.g., ruboxistaurin mesylate monohydrate), and three or more excipients selected from: a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; c) an alcohol; and d) a gelling agent. In some embodiments the composition comprises the PK inhibitor, without limitation, such as ruboxistaurin free base or a ruboxistaurin salt (e.g., ruboxistaurin mesylate monohydrate), or an acceptable salt thereof, and four or more excipients selected from: an organic solvent and/or penetration enhancer (e.g., a) a $C_{2-6}$ alkylene glycol, $C_{1-3}$ alkyl-$(OCH_2CH_2)_{1-5}$—OH, and/or PEG); b) an antioxidant; c) an alcohol; and f) a gelling agent. In some embodiments the composition comprises the PK inhibitor, without limitation, such as ruboxistaurin free base or a ruboxistaurin salt (e.g., ruboxistaurin mesylate monohydrate), or an acceptable salt thereof and five or more excipients selected from: a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; c) an alcohol; and d) a gelling agent. In some embodiments the composition comprises the PK inhibitor, without limitation, such as ruboxistaurin free base or a ruboxistaurin salt (e.g., ruboxistaurin mesylate monohydrate), or an acceptable salt thereof and a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; c) an alcohol; and d) a gelling agent. In some cases, the organic solvent and/or penetration enhancer comprises $C_{2-6}$ alkylene glycol. In some cases, the organic solvent and/or penetration enhancer comprises $C_{1-3}$ alkyl-$(OCH_2CH_2)_{1-5}$—OH. In some cases, the organic solvent and/or penetration enhancer comprises PEG. In some cases, the organic solvent and/or penetration enhancer comprises $C_{2-6}$ alkylene glycol, $C_{1-3}$ alkyl-$(OCH_2CH_2)_{1-5}$—OH, and PEG. In some cases the antioxidant comprises BHT. In some cases, the antioxidant comprises BHA. In some cases, the antioxidant comprise BHT and/or BHA. In some cases, the alcohol comprises glycerol. In some cases, the gelling agent comprises HPC. In some cases, the gelling agent comprises PEG. In some cases, the gelling agent comprises HPC and PEG. The composition may be formulated at 0.1% w/w or 0.12% w/w or 0.8% w/w ruboxistaurin mesylate monohydrate, 0.08% w/w or 0.1% w/w or 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% ruboxistaurin free base or a salt thereof, for administration twice daily, for about 12 weeks. In a non-limiting embodiment, the composition is formulated at 0.64% ruboxistaurin free base or a salt thereof, for administration twice daily, for about 4 to about 8 weeks. In a non-limiting embodiment, the composition is formulated at 0.64% ruboxistaurin free base or a salt thereof, for administration twice daily, for about 8 to about 12 weeks. In a non-limiting embodiment, the composition is formulated at 0.64% ruboxistaurin free base or a salt thereof, for administration twice daily, for about 12 weeks to about 6 months. In a non-limiting embodiment, the composition is formulated at 0.1% or 0.08% ruboxistaurin free base or a salt thereof, for administration twice daily, for about 12 weeks. In a non-limiting embodiment, the composition is formulated at 0.1% or 0.08% ruboxistaurin free base or a salt thereof, for administration twice daily, for about 4 to about 8 weeks. In a non-limiting embodiment, the composition is formulated at 0.1% or 0.08% ruboxistaurin free base or a salt thereof, for administration twice daily, for about 8 to about 12 weeks. In a non-limiting embodiment, the composition is formulated at 0.1% or 0.08% ruboxistaurin free base or a salt thereof, for administration twice daily, for about 12 weeks to about 6 months. In a non-limiting embodiment, the composition is formulated at 0.8% ruboxistaurin mesylate monohydrate, for administration twice daily, for about 12 weeks. In a non-limiting embodiment, the composition is formulated at 0.8% ruboxistaurin free base or a salt thereof, for administration twice daily, for about 4 to about 8 weeks. In a non-limiting embodiment, the composition is formulated at 0.8% ruboxistaurin free base or a salt thereof, for administration twice daily, for about 8 to about 12 weeks. In a non-limiting embodiment, the composition is formulated at 0.8% ruboxistaurin free base or a salt thereof, for administration twice daily, for about 12 weeks to about 6 months. In a non-limiting embodiment, the composition is formulated at 0.1% or 0.12% ruboxistaurin mesylate monohydrate, for administration twice daily, for about 12 weeks. In a non-limiting embodiment, the composition is formulated at 0.1% or 0.12% ruboxistaurin free base or a salt thereof, for administration twice daily, for about 4 to about 8 weeks. In a non-limiting embodiment, the composition is formulated at 0.1% or 0.12% ruboxistaurin free base or a salt thereof, for administration twice daily, for about 8 to about 12 weeks. In a non-limiting embodiment, the composition is formulated at 0.1% or 0.12% ruboxistaurin free base or a salt thereof, for administration twice daily, for about 12 weeks to about 6 months In some embodiments the composition comprises the PK inhibitor, without limitation, such as ruboxistaurin free base or a ruboxistaurin salt (e.g., ruboxistaurin mesylate monohydrate), and an organic solvent and/or penetration enhancer (e.g., a $C_{2-6}$ alkylene glycol, $C_{1-3}$ alkyl-$(OCH_2CH_2)_{1-5}$—OH, and/or PEG). In some embodiments, the composition comprises the PK inhibitor, without limitation, such as ruboxistaurin free base or a ruboxistaurin salt (e.g., ruboxistaurin mesylate monohydrate), and a) an organic solvent and/or penetration enhancer (e.g., a $C_{2-6}$ alkylene glycol, $C_{1-3}$ alkyl-$(OCH_2CH_2)_{1-5}$—OH, and/or PEG); and b) an antioxidant. In some embodiments, the composition comprises the PK inhibitor, without limitation, such as ruboxistaurin free base or a ruboxistaurin salt (e.g., ruboxistaurin mesylate monohydrate), or an acceptable salt thereof, and a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; and c) a gelling agent. In some embodiments, the composition comprises the PK inhibitor, without limitation, such as ruboxistaurin free base or a ruboxistaurin salt (e.g., ruboxistaurin mesylate monohydrate), and a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an antioxidant; c) an alcohol and d) a gelling agent. In some embodiments the composition comprises ruboxistaurin the PK inhibitor, without limitation, such as ruboxistaurin free base or a ruboxistaurin salt (e.g., ruboxistaurin mesylate monohydrate), and a) an organic solvent and/or penetration enhancer (e.g., a $C_{2-6}$ alkylene glycol, $C_{1-3}$ alkyl-$(OCH_2CH_2)_{1-5}$—OH, and/or PEG); b) an alcohol and c) a gelling agent. In some embodiments the composition comprises the PK inhibitor, without limitation, such as ruboxistaurin free base or a ruboxistaurin salt (e.g., ruboxistaurin mesylate monohydrate), and a) an organic solvent and/or penetration enhancer (e.g., a $C_{2-6}$ alkylene glycol, $C_{1-3}$ alkyl-$(OCH_2CH_2)_{1-5}$—OH, and/or PEG); and b) an alcohol. In some embodiments the composition comprises the PK inhibitor, without limitation, such as ruboxistaurin free base or a ruboxistaurin salt (e.g., ruboxistaurin mesylate monohydrate), and a) an organic solvent and/or penetration enhancer (e.g., a $C_{2-6}$ alkylene glycol, $C_{1-3}$ alkyl-$(OCH_2CH_2)_{1-5}$—OH, and/or PEG); and b) a gelling agent. In some embodiments the composition comprises the PK inhibitor, without limitation, such as ruboxistaurin free base or a ruboxistaurin salt (e.g., ruboxistaurin mesylate monohydrate), and a) an antioxidant; b) an alcohol; and c) a gelling agent. In some embodiments the composition comprises the PK inhibitor, without limitation, such as ruboxistaurin free base or a ruboxistaurin salt (e.g., ruboxistaurin mesylate monohydrate), and a) an antioxidant; and b) an alcohol. In some embodiments the composition comprises the PK inhibitor, without limitation, such as ruboxistaurin free base or a ruboxistaurin salt (e.g., ruboxistaurin mesylate monohydrate), and a) an antioxidant; and b) a gelling agent. In some embodiments the composition comprises the PK inhibitor, without limitation, such as ruboxistaurin free base or a ruboxistaurin salt (e.g., ruboxistaurin mesylate monohydrate), and a) an alcohol; and b) a gelling agent. In some embodiments the composition comprises the PK inhibitor, without limitation, such as ruboxistaurin free base or a ruboxistaurin salt (e.g., ruboxistaurin mesylate monohydrate), and an alcohol. In some embodiments the composition includes an antioxidant. In some embodiments the composition comprises the PK inhibitor, without limitation, such as ruboxistaurin free base or a ruboxistaurin salt (e.g., ruboxistaurin mesylate monohydrate), and a gelling agent. In some cases, the organic solvent and/or penetration enhancer comprises $C_{2-6}$ alkylene glycol. In some cases, the organic solvent and/or penetration enhancer comprises $C_{1-3}$ alkyl-$(OCH_2CH_2)_{1-5}$—OH. In some cases, the organic solvent and/or penetration enhancer comprises PEG. In some cases, the organic solvent and/or penetration enhancer comprises $C_{2-6}$ alkylene glycol, $C_{1-3}$ alkyl-$(OCH_2CH_2)_{1-5}$—OH, and PEG. In some cases the antioxidant comprises BHT. In some cases, the antioxidant comprises BHA. In some cases, the antioxidant comprise BHT and/or BHA. In some cases, the alcohol comprises glycerol. In some cases, the gelling agent comprises HPC. In some cases, the gelling agent comprises PEG. In some cases, the gelling agent comprises HPC and PEG. The composition may be formulated at 0.1% w/w to 0.8% w/w ruboxistaurin mesylate monohydrate, 0.08% w/w to 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% ruboxistaurin free base or a salt thereof, for administration twice daily, for about 12 weeks. In a non-limiting embodiment, the composition is formulated at 0.64% ruboxistaurin free base or a salt thereof, for administration twice daily, for about 4 to about 8 weeks. In a non-limiting embodiment, the composition is formulated at 0.08% to 0.1% ruboxistaurin free base or a salt thereof, for administration twice daily, for about 12 weeks. In a non-limiting embodiment, the composition is formulated at 0.08% to 0.1% ruboxistaurin free base or a salt thereof, for administration twice daily, for about 4 to about 8 weeks. In a non-limiting embodiment, the composition is formulated at 0.8% ruboxistaurin monohydrate mesylate or a salt thereof, for administration twice daily, for about 12 weeks. In a non-limiting embodiment, the composition is formulated at 0.8% ruboxistaurin mesylate monohydrate or a salt thereof, for administration twice daily, for about 4 to about 8 weeks. In a non-limiting embodiment, the composition is formulated at 0.1% or 0.12% ruboxistaurin monohydrate mesylate or a salt thereof, for administration twice daily, for about 12 weeks. In a non-limiting embodiment, the composition is formulated at 0.1% or 0.12% ruboxistaurin mesylate monohydrate or a salt thereof, for administration twice daily, for about 4 to about 8 weeks.

In some embodiments, the present disclosure provides a composition (A) comprising the PK inhibitor, without limitation, such as ruboxistaurin free base or a ruboxistaurin salt (e.g., ruboxistaurin mesylate monohydrate), and one or more of the following excipients:
  a) an organic solvent and/or penetration enhancer (e.g., a $C_{2-6}$ alkylene glycol, $C_{1-3}$ alkyl-$(OCH_2CH_2)_{1-5}$—OH, and/or PEG);
  b) an antioxidant;
  c) an alcohol; and
  d) a gelling agent.

In some cases, the compound, the organic solvent and/or penetration enhancer, the antioxidant, the alcohol and/or the gelling agent are as described herein. In some cases, the organic solvent and/or penetration enhancer comprises $C_{2-6}$ alkylene glycol. In some cases, the organic solvent and/or penetration enhancer comprises $C_{1-3}$ alkyl-$(OCH_2CH_2)_{1-5}$—OH. In some cases, the organic solvent and/or penetration enhancer comprises PEG. In some cases, the organic solvent and/or penetration enhancer comprises $C_{2-6}$ alkylene glycol, $C_{1-3}$ alkyl-$(OCH_2CH_2)_{1-5}$—OH, and PEG. In some cases the antioxidant comprises BHT. In some cases, the antioxidant comprises BHA. In some cases, the antioxidant comprise BHT and/or BHA. In some cases, the alcohol comprises glycerol. In some cases, the gelling agent comprises HPC. In some cases, the gelling agent comprises PEG. In some cases, the gelling agent comprises HPC and PEG. The composition may be formulated at 0.1% w/w to 0.8% w/w for ruboxistaurin mesylate monohydrate 0.08% w/w to 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.08% w/w or 0.1% w/w or 0.64% PK inhibitor, without limitation, such as ruboxistaurin free base or a ruboxistaurin salt (e.g., ruboxistaurin mesylate monohydrate), for administration twice daily, for about 12 weeks. In a non-limiting embodiment, the composition is formulated at 0.08% w/w or 0.1% w/w or 0.64% PK inhibitor, without limitation, such as ruboxistaurin free base or a ruboxistaurin salt (e.g., ruboxistaurin mesylate monohydrate), for administration twice daily, for about 4 to about 8 weeks. In a non-limiting embodiment, the composition is formulated at 0.1% w/w or 0.12% w/w or 0.8% w/w PK inhibitor, without limitation, such as ruboxistaurin free base or a ruboxistaurin salt (e.g., ruboxistaurin mesylate monohydrate), for administration twice daily, for about 12 weeks. In a non-limiting embodiment, the composition is formulated at 0.1% w/w or 0.12% w/w or 0.8% w/w PK inhibitor, without limitation, such as ruboxistaurin free base or a ruboxistaurin salt (e.g., ruboxistaurin mesylate monohydrate), for administration twice daily, for about 4 to about 8 weeks.

In some embodiments of composition (A), the antioxidant is absent in the composition.

In some embodiments of composition (A), one or more of the antioxidants are present in the composition. In some embodiments of composition (A) the antioxidant is present in the composition. In some cases the antioxidant comprises BHT. In some cases, the antioxidant comprises BHA. In some cases, the antioxidant is comprised of BHT and/or BHA.

In some embodiments, the present disclosure provides a composition (B) comprising a PK inhibitor, without limitation, such as ruboxistaurin free base or a ruboxistaurin salt (e.g., ruboxistaurin mesylate monohydrate) and excipients a), b), c), and d):
  a) an organic solvent and/or penetration enhancer (e.g., a $C_{2-6}$ alkylene glycol, $C_{1-3}$ alkyl-$(OCH_2CH_2)_{1-5}$—OH, and/or PEG);
  b) an antioxidant;
  c) an alcohol; and
  d) a gelling agent.

In some cases, the compound, the organic solvent and/or penetration enhancer, the antioxidant, the solvent, and/or the gelling agent are as described herein. In some cases, the organic solvent and/or penetration enhancer comprises $C_{2-6}$ alkylene glycol. In some cases, the organic solvent and/or penetration enhancer comprises $C_{1-3}$ alkyl-$(OCH_2CH_2)_{1-5}$—OH. In some cases, the organic solvent and/or penetration enhancer comprises PEG. In some cases, the organic solvent and/or penetration enhancer comprises $C_{2-6}$ alkylene glycol, $C_{1-3}$ alkyl-$(OCH_2CH_2)_{1-5}$—OH, and PEG. In some cases the antioxidant comprises BHT. In some cases, the antioxidant comprises BHA. In some cases, the antioxidant comprises BHT and/or BHA. In some cases, the alcohol comprises glycerol. In some cases, the gelling agent comprises HPC. In some cases, the gelling agent comprises PEG. In some cases, the gelling agent comprises HPC and PEG. The composition may be formulated at 0.1% w/w to 0.8% w/w ruboxistaurin mesylate monohydrate, 0.08% w/w to 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% ruboxistaurin free base or a salt thereof, for administration twice daily, for about 12 weeks. In a non-limiting embodiment, the composition is formulated at 0.64% ruboxistaurin free base or a salt thereof, for administration twice daily, for about 4 to about 8 weeks. In a non-limiting embodiment, the composition is formulated at 0.08% to 0.1% ruboxistaurin free base or a salt thereof, for administration twice daily, for about 12 weeks. In a non-limiting embodiment, the composition is formulated at 0.08% to 0.1% ruboxistaurin free base or a salt thereof, for administration twice daily, for about 4 to about 8 weeks. In a non-limiting embodiment, the composition is formulated at 0.8% ruboxistaurin monohydrate mesylate or a salt thereof, for administration twice daily, for about 12 weeks. In a non-limiting embodiment, the composition is formulated at 0.8% ruboxistaurin mesylate monohydrate or a salt thereof, for administration twice daily, for about 4 to about 8 weeks. In a non-limiting embodiment, the composition is formulated at 0.1% or 0.12% ruboxistaurin monohydrate mesylate or a salt thereof, for administration twice daily, for about 12 weeks. In a non-limiting embodiment, the composition is formulated at 0.1% or 0.12% ruboxistaurin mesylate monohydrate or a salt thereof, for administration twice daily, for about 4 to about 8 weeks.

In some embodiments, the present disclosure provides a composition (C) comprising a PK inhibitor, without limitation, such as ruboxistaurin free base or a ruboxistaurin salt (e.g., ruboxistaurin mesylate monohydrate), and excipients a), b) and d):

a) an organic solvent and/or penetration enhancer (e.g., a $C_{2-6}$ alkylene glycol, $C_{1-3}$ alkyl-$(OCH_2CH_2)_{1-5}$—OH, and/or PEG);
b) an antioxidant; and
d) a gelling agent.

In some cases, the compound, the organic solvent and/or penetration enhancer, the antioxidant, and/or the gelling agent are as described herein. The composition may be formulated at 0.1% w/w to 0.8% w/w ruboxistaurin mesylate monohydrate, 0.08% w/w to 0.64% w/w ruboxistaurin free base, or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% PK inhibitor, without limitation, such as ruboxistaurin free base or a ruboxistaurin salt (e.g., ruboxistaurin mesylate monohydrate), for administration twice daily, for about 12 weeks. In a non-limiting embodiment, the composition is formulated at 0.64% PK inhibitor, without limitation, such as ruboxistaurin free base or a ruboxistaurin salt (e.g., ruboxistaurin mesylate monohydrate), for administration twice daily, for about 4 to about 8 weeks. In a non-limiting embodiment, the composition is formulated at 0.08% to 0.1% ruboxistaurin free base or a salt thereof, for administration twice daily, for about 12 weeks. In a non-limiting embodiment, the composition is formulated at 0.08% to 0.1% ruboxistaurin free base or a salt thereof, for administration twice daily, for about 4 to about 8 weeks. In a non-limiting embodiment, the composition is formulated at 0.8% ruboxistaurin monohydrate mesylate or a salt thereof, for administration twice daily, for about 12 weeks. In a non-limiting embodiment, the composition is formulated at 0.8% ruboxistaurin mesylate monohydrate or a salt thereof, for administration twice daily, for about 4 to about 8 weeks. In a non-limiting embodiment, the composition is formulated at 0.1% or 0.12% ruboxistaurin monohydrate mesylate or a salt thereof, for administration twice daily, for about 12 weeks. In a non-limiting embodiment, the composition is formulated at 0.1% or 0.12% ruboxistaurin mesylate monohydrate or a salt thereof, for administration twice daily, for about 4 to about 8 weeks.

In some embodiments, the present disclosure provides a composition (D) comprising PK inhibitor, without limitation, such as ruboxistaurin free base or a ruboxistaurin salt (e.g., ruboxistaurin mesylate monohydrate), and excipients a), b) and c):

a) an organic solvent and/or penetration enhancer (e.g., a $C_{2-6}$ alkylene glycol, $C_{1-3}$ alkyl-$(OCH_2CH_2)_{1-5}$—OH, and/or PEG);
b) an antioxidant; and
c) an alcohol.

In some cases, the compound, the organic solvent and/or penetration enhancer, the antioxidant, and/or the alcohol are as described herein. The composition may be formulated at 0.1% w/w to 0.8% w/w ruboxistaurin mesylate monohydrate, 0.08% w/w to 0.64% w/w ruboxistaurin free base or other salt thereof. In some cases the composition is administered once or twice daily. In some cases, the composition is administered for about 12 weeks to about 6 months. In some cases, the composition is administered for about 4 weeks to about 8 weeks. In some cases, the composition is administered for about 8 weeks to about 12 weeks. In a non-limiting embodiment, the composition is formulated at 0.64% PK inhibitor, without limitation, such as ruboxistaurin free base or a ruboxistaurin salt (e.g., ruboxistaurin mesylate monohydrate), for administration twice daily, for about 12 weeks. In a non-limiting embodiment, the composition is formulated at 0.64% ruboxistaurin free base or a salt thereof, for administration twice daily, for about 4 to about 8 weeks. In a non-limiting embodiment, the composition is formulated at 0.08% to 0.1% ruboxistaurin free base or a salt thereof, for administration twice daily, for about 12 weeks. In a non-limiting embodiment, the composition is formulated at 0.08% to 0.1% ruboxistaurin free base or a salt thereof, for administration twice daily, for about 4 to about 8 weeks. In a non-limiting embodiment, the composition is formulated at 0.8% ruboxistaurin monohydrate mesylate or a salt thereof, for administration twice daily, for about 12 weeks. In a non-limiting embodiment, the composition is formulated at 0.8% ruboxistaurin mesylate monohydrate or a salt thereof, for administration twice daily, for about 4 to about 8 weeks. In a non-limiting embodiment, the composition is formulated at 0.1% or 0.12% ruboxistaurin monohydrate mesylate or a salt thereof, for administration twice daily, for about 12 weeks. In a non-limiting embodiment, the composition is formulated at 0.1% or 0.12% ruboxistaurin mesylate monohydrate or a salt thereof, for administration twice daily, for about 4 to about 8 weeks.

In some embodiments, the organic solvent and/or penetration enhancer of any one of compositions (A), (B), (C), and/or (D) comprises $C_{2-6}$ alkylene glycol present in the composition in an amount of from about 10% to about 40%, from about 10% to about 30%, or about 20% by weight. In some embodiments, the $C_{2-6}$ alkylene glycol is present in an amount of from about 10% to about 30%. In some embodiments, the $C_{2-6}$ alkylene glycol is present in an amount of from about 15% to about 25%. In some embodiments, the $C_{2-6}$ alkylene glycol is present in an amount of about 20% by weight.

In some embodiments, the $C_{2-6}$ alkylene glycol of any one of compositions (A), (B), (C), and/or (D) is a combination of $C_{2-6}$ alkylene glycols. In some embodiments the $C_{2-6}$ alkylene glycols are present in the composition in a total amount of from about 10% to about 60%, from about 20% to about 40%, or about 34% by weight. In some embodiments, the $C_{2-6}$ alkylene glycols are present in a total amount of from about 20% to about 40%. In some embodiments, the $C_{2-6}$ alkylene glycols are present in an amount of from about 25% to about 35%. In some embodiments, the $C_{2-6}$ alkylene glycols are present in an amount of about 34% by weight.

In some embodiments, the organic solvent and/or penetration enhancer of any one of compositions (A), (B), (C), and/or (D) comprises $C_{1-3}$ alkyl-$(OCH_2CH_2)_{1-5}$—OH present in an amount of from about 30% to about 70%, from about 40% to about 60%, or about 47% by weight. In some embodiments, $C_{1-3}$ alkyl-$(OCH_2CH_2)_{1-5}$—OH is present in an amount of from about 30% to about 70% by weight. In some embodiments, $C_{1-3}$ alkyl-$(OCH_2CH_2)_{1-5}$—OH is present in an amount of from about 40% to about 60% by weight. In some embodiments, $C_{1-3}$ alkyl-$(OCH_2CH_2)_{1-5}$—OH is present in an amount of about 47% by weight.

In some embodiments, an alcohol is present in an amount of from about 10% to about 30%, from about 10% to about 20%, or about 15% by weight of any one of compositions (A), (B), (C), and/or (D). In some embodiments, the alcohol is present in an amount of from about 10% to about 30%. In some embodiments, the alcohol is present in an amount of from about 10% to about 20%. In some embodiments, the alcohol is present in an amount of about 15% by weight. In some cases, the alcohol comprises glycerol.

In some embodiments, the gelling agent of any one of compositions (A), (B), and/or (C) is present in an amount of from about 1% to about 4% or about 3% by weight, and the composition has a viscosity of from about 5,000 cP to about 30,000 cP. In some embodiments, the gelling agent is present in an amount of from about 1% to about 4% or about 3% by weight, and the composition has a viscosity of from about 10,000 cP to about 30,000 cP. In some embodiments, the gelling agent is present in an amount of from about 1% to about 3% or about 2% by weight, and the composition has a viscosity of from about 15,000 cP to about 30,000 cP. In some embodiments, the gelling agent is present in an amount of from about 1% to about 4% or about 5% by weight, and the composition has a viscosity of from about 20,000 cP to about 30,000 cP. In some cases, the gelling agent comprises PEG. In some cases, the gelling agent comprises HPC and PEG.

In some embodiments, the organic solvent and/or penetration enhancer of any one of compositions (A), (B), (C), and/or (D) comprises $C_{2-6}$ alkylene glycol, and the $C_{2-6}$ alkylene glycol is propylene glycol; the organic solvent and/or penetration enhancer comprises $C_{1-3}$ alkyl-$(OCH_2CH_2)_{1-5}$—OH, and the $C_{1-3}$ alkyl-$(OCH_2CH_2)_{1-5}$—OH is 2-(2-ethoxyethoxy)ethanol; and the gelling agent is hydroxypropyl cellulose. In some embodiments of any one of compositions (A), (B), (C), and (D), the organic solvent and/or penetration enhancer comprises $C_{2-6}$ alkylene glycol, and the $C_{2-6}$ alkylene glycol is polyethylene glycol; the organic solvent and/or penetration enhancer comprises $C_{1-3}$ alkyl-$(OCH_2CH_2)_{1-5}$—OH, and the $C_{1-3}$ alkyl-$(OCH_2CH_2)_{1-5}$—OH is 2-(2-ethoxyethoxy)ethanol; and the gelling agent is hydroxypropyl cellulose.

In some embodiments, the composition (A1) comprises a PK inhibitor, without limitation, such as ruboxistaurin free base or a ruboxistaurin salt (e.g., ruboxistaurin mesylate monohydrate), and one or more of the following excipients:
 a) propylene glycol, polyethylene glycol, and/or 2-(2-ethoxyethoxy)ethanol;
 b) butylated hydroxytoluene and/or butylated hydroxyanisole;
 c) glycerol and/or an alcohol; and
 d) hydroxypropyl cellulose.

In some cases, the compound, propylene glycol, polyethylene glycol, and/or 2-(2-ethoxyethoxy)ethanol, butylated hydroxytoluene and/or butylated hydroxyanisole, glycerol and/or an alcohol solvent, and/or hydroxypropyl cellulose are as described herein.

In some embodiments, the composition (B1) comprises a PK inhibitor, without limitation, such as ruboxistaurin free base or a ruboxistaurin salt (e.g., ruboxistaurin mesylate monohydrate) and excipients a), b), c), and d):
 a) propylene glycol, polyethylene glycol, and/or 2-(2-ethoxyethoxy)ethanol;
 b) butylated hydroxytoluene and/or butylated hydroxyanisole;
 c) glycerol and/or an alcohol; and
 d) hydroxypropyl cellulose.

In some cases, the compound, propylene glycol, polyethylene glycol, and/or 2-(2-ethoxyethoxy)ethanol, butylated hydroxytoluene and/or butylated hydroxyanisole, glycerol and/or an alcohol, and/or hydroxypropyl cellulose are as described herein.

In some embodiments, the composition (C1) comprises a PK inhibitor, without limitation, such as ruboxistaurin free base or a ruboxistaurin salt (e.g., ruboxistaurin mesylate monohydrate) and excipients a), b) and c):
 a) propylene glycol, polyethylene glycol, and/or 2-(2-ethoxyethoxy)ethanol;
 b) butylated hydroxytoluene and/or butylated hydroxyanisole; and
 c) hydroxypropyl cellulose.

In some cases, the compound, propylene glycol, polyethylene glycol, and/or 2-(2-ethoxyethoxy)ethanol, butylated hydroxytoluene and/or butylated hydroxyanisole, and/or hydroxypropyl cellulose are as described herein.

In some embodiments, the composition (D1) comprises a PK inhibitor, without limitation, such as ruboxistaurin free base or a ruboxistaurin salt (e.g., ruboxistaurin mesylate monohydrate) and excipients a), b) and c):
 a) propylene glycol, polyethylene glycol, and/or 2-(2-ethoxyethoxy)ethanol;
 b) butylated hydroxytoluene and/or butylated hydroxyanisole; and
 c) glycerol and/or an alcohol.

In some cases, the compound, propylene glycol, polyethylene glycol, and/or 2-(2-ethoxyethoxy)ethanol, butylated hydroxytoluene and/or butylated hydroxyanisole, and/or glycerol and/or an alcohol are as described herein.

In some embodiments of any one of compositions (A), (B), (C), (D), the antioxidant, if present, is butylated hydroxytoluene, butylated hydroxyanisole, propyl gallate, or combinations of two or more thereof. In some embodiments, the antioxidant, when present, is butylated hydroxytoluene and/or butylated hydroxyanisole.

In some embodiments, the antioxidant of any one of compositions (A), (B), (C), (D), (A1), (B1), (C1), and/or (D1), when present, is present in an amount of from about 0.01% to about 0.5% or about 0.1% by weight. In some embodiments, the antioxidant, when present, is present in an amount of from about 0.01% to about 0.5% by weight. In some embodiments, the antioxidant, when present, is present in an amount of about 0.2% by weight.

In some embodiments, the composition (C1a) comprises a PK inhibitor, without limitation, such as ruboxistaurin free base or a ruboxistaurin salt (e.g., ruboxistaurin mesylate monohydrate), and excipients a), b), c) and d):
 a) propylene glycol and 2-(2-ethoxyethoxy)ethanol;
 b) butylated hydroxytoluene and/or butylated hydroxyanisole;
 c) glycerol and/or polyethylene glycol; and
 d) hydroxypropyl cellulose.

In some cases, the compound, propylene glycol and 2-(2-ethoxyethoxy)ethanol, butylated hydroxytoluene and/or butylated hydroxyanisole, glycerol and/or polyethylene glycol, and/or hydroxypropyl cellulose are as described herein.

In some embodiments, ethanol is present in any one of compositions (A1), (B1), (C1), and/or (C1a) in an amount of from about 10% to about 30%, from about 10% to about 20%, or about 15% by weight. In some embodiments, ethanol is present in an amount of from about 10% to about 30% by weight. In some embodiments, ethanol is present in an amount of from about 10% to about 20% by weight. In some embodiments, ethanol is present in an amount of about 15% by weight.

In some embodiments, polyethylene glycol is present in any one of compositions (A1), (B1), (C1), and/or (C1a) in an amount of from about 10% to about 30%, from about 10% to about 20%, or about 15% by weight. In some embodiments, polyethylene glycol is present in an amount of from about 10% to about 30% by weight. In some embodiments, polyethylene glycol is present in an amount of from about 10% to about 20% by weight. In some embodiments, polyethylene glycol is present in an amount of about 14% by weight.

In some embodiments, glycerol is present in any one of compositions (A1), (B1), (C1), and/or (C1a) in an amount of from about 10% to about 30%, from about 10% to about 20%, or about 15% by weight. In some embodiments, glycerol is present in an amount of from about 10% to about 30% by weight. In some embodiments, propylene glycol is present in an amount of from about 10% to about 20% by weight. In some embodiments, glycerol is present in an amount of about 15% by weight.

In some embodiments, 2-(2-ethoxyethoxy)ethanol is present in any one of compositions (A1), (B1), (C1), and/or (C1a) in an amount of from about 30% to about 50%, from about 40% to about 60%, or about 47% by weight. In some embodiments, 2-(2-ethoxyethoxy)ethanol is present in an amount of from about 30% to about 50% by weight. In some embodiments, 2-(2-ethoxyethoxy)ethanol is present in an amount of from about 40% to about 50% by weight. In some embodiments, 2-(2-ethoxyethoxy)ethanol is present in an amount of about 47% by weight.

In some embodiments, propylene glycol is present in any one of compositions (A1), (B1), (C1), and/or (C1a) in an amount of from about 10% to about 30%, or about 20% by weight. In some embodiments, propylene glycol is present in an amount of from about 10% to about 30% by weight. In some embodiments, propylene glycol is present in an amount of about 20% by weight.

In some embodiments, hydroxypropyl cellulose having an average molecular weight of from about 700,000 Da to about 1,150,000 Da is present in any one of compositions (A1), (B1), (C1), and/or (C1a) in an amount of from about 1% to about 3% or about 2% by weight. In some embodiments, hydroxypropyl cellulose having an average molecular weight of from about 700,000 Da to about 1,150,000 Da is present in an amount of from about 1% to about 3% by weight. In some embodiments, hydroxypropyl cellulose having an average molecular weight of from about 700,000 Da to about 1,150,000 Da is present in an amount of about 1% by weight. In some embodiments, hydroxypropyl cellulose having an average molecular weight of from about 700,000 Da to about 1,150,000 Dais present in an amount of about 2% by weight. In some embodiments, hydroxypropyl cellulose is Klucel MF in an amount of about 2% by weight.

In some embodiments, butylated hydroxytoluene and/or butylated hydroxyanisole is present in the composition (C1a) in an amount of from about 0.01% to about 0.5% or about 0.1% by weight. In some embodiments, butylated hydroxytoluene and/or butylated hydroxyanisole is present in an amount of from about 0.01% to about 0.2% by weight. In some embodiments, butylated hydroxytoluene is present in an amount of about 0.1% by weight. In some embodiments butylated hydroxyanisole is present in an amount of about 0.1% by weight.

In some embodiments, butylated hydroxytoluene is present in the composition (C1a) in an amount of about 0.2% by weight. In some embodiments of composition (C1a), butylated hydroxyanisole is present in an amount of about 0.2% by weight In some embodiments of compositions (A), (B), (C), (A1), (B1), (C1), and (C1a), propylene glycol is a super refined propylene glycol.

In some embodiments of compositions (A), (B), (C), (A1), (B1), (C1), and (C1a), polyethylene glycol is a super refined polyethylene glycol.

In some embodiments of compositions (A), (B), (C), (A1), (B1), (C1), and (C1a), 2-(2-ethoxyethoxy)ethanol is Transcutol HP having a purity of >99.90%.

In some embodiments of compositions (A), (B), (C), (A1), (B1), (C1), and (C1a), or any PK inhibitor (e.g., ruboxistaurin free base or a salt thereof (e.g., ruboxistaurin mesylate monohydrate) composition described herein is 50-99% by weight glycol, 55%-99% by weight glycol, 60%-99% by weight glycol, 65%-99% by weight glycol, 70%-99% by weight glycol, 75%-99% by weight glycol, 80-99% by weight glycol, 85-99% by weight glycol, 90-99% by weight glycol, or 95-99% by weight glycol. In some embodiments of compositions (A), (B), (C), (A1), (B1), (C1), and (C1a), or any PK inhibitor (e.g., ruboxistaurin free base or a salt thereof (e.g., ruboxistaurin mesylate monohydrate) composition herein is 80%-95% by weight glycol, 80%-96% glycol, or 80%-97% glycol.

In some embodiments, the PK inhibitor, without limitation, such as ruboxistaurin free base or a ruboxistaurin salt (e.g., ruboxistaurin mesylate monohydrate) is present in one or more of compositions (A), (B), (C), (A1), (B1), (C1), and/or (C1a) in an amount of from about 0.5% to about 2% or about 1% by weight. In some embodiments, the PK inhibitor, without limitation, such as ruboxistaurin free base or a ruboxistaurin salt (e.g., ruboxistaurin mesylate monohydrate) is present in an amount of from about 0.10% to about 2% by weight. In some embodiments, the PK inhibitor, without limitation, such as ruboxistaurin free base or a ruboxistaurin salt (e.g., ruboxistaurin mesylate monohydrate) is present in an amount of about 0.1%, 0.2%, 0.3%, 0.4%, 0.5%, 0.6%, 0.7%, 0.8%, 0.9% or 1% of the composition. In some embodiments, the PK inhibitor, without limitation, such as ruboxistaurin free base or a ruboxistaurin salt (e.g., ruboxistaurin mesylate monohydrate) is present in an amount of about 0.8% by weight.

In non-limiting example embodiments herein, the PK inhibitor comprises or is ruboxistaurin free base, ruboxistaurin mesylate, or ruboxistaurin mesylate monohydrate.

In non-limiting example embodiments herein, the PK inhibitor comprises or is ruboxistaurin mesylate monohydrate.

I-5. Forms of Compositions

Topical compositions useful for delivering the compound to a subject (e.g., to the skin of a subject) include, but are not limited to, foams, sprays, aerosols, creams, lotions, ointments, gels, solutions, emulsions, and suspensions. See, e.g., REMINGTON: THE SCIENCE AND PRACTICE OF PHARMACY; (Alfonso R. Gennaro ed. 19th ed. 1995); and Introduction to Pharmaceutical Dosage Forms, 4th ed., Lea & Febiger, Philadelphia (1985), herein incorporated by reference in its entirety. In some embodiments, the topical composition used to deliver the compound is a gel, ointment, lotion, foam or emollient.

In some embodiments, the topical composition used to deliver the compound is a lotion or a cream. Creams and lotions that can be used as topical compositions and their preparation are disclosed in REMINGTON: THE SCIENCE AND PRACTICE OF PHARMACY 282-291 (Alfonso R. Gennaro ed. 19th ed. 1995), the relevant portions of which are hereby incorporated herein by reference.

In some embodiments, the topical composition is a gel, for example, a two-phase gel or a single-phase gel. Gels are semisolid systems consisting of suspensions of small inorganic particles or large organic molecules interpenetrated by a liquid. When the gel mass comprises a network of small discrete inorganic particles, it is classified as a two-phase gel. Single-phase gels consist of organic macromolecules distributed uniformly throughout a liquid such that no apparent boundaries exist between the dispersed macromolecules and the liquid. Suitable gels for use in the disclosure are disclosed in REMINGTON: THE SCIENCE AND PRACTICE OF PHARMACY 1517-1518 (Alfonso R. Gennaro ed. 19th ed. 1995), which is hereby incorporated herein by reference. Other suitable gels for use with the disclosure are disclosed in U.S. Pat. No. 6,387,383 (issued May 14, 2002), 6,517,847 (issued Feb. 11, 2003), and 6,468,989 (issued Oct. 22, 2002).

In some embodiments, the topical composition is an ointment. Ointments are oleaginous semisolids that contain little if any water. In some instances, the ointment is hydrocarbon based, such as a wax, petrolatum, or gelled mineral oil. Suitable ointments for use according to the present disclosure include those disclosed in REMINGTON: THE SCIENCE AND PRACTICE OF PHARMACY 1585-1591 (Alfonso R. Gennaro ed. 19th ed. 1995).

In some embodiments, the topical composition may be in the form of a patch, tape, film, wafer, wipe, paper, clothe, towel, towelette, sponge, foam, mask, or bandage including the topical composition as described herein. In some embodiments, the patch, tape, film, wafer, wipe, paper, clothe, towel, towelette, sponge, foam, mask, or bandage is in contact with the affected area on the skin. In some embodiments, the patch, tape, film, wafer, wipe, paper, clothe, towel, towelette, sponge, foam, mask, face mask, brush, pad, gauze, applicator, cotton ball, roll, swab, or bandage, when applied to a subject, is in contact with areas of the skin of the subject that are adjacent to the affected or target area.

In some embodiments, the topical administration may be in the form of a patch, tape, film, wafer, wipe, paper, clothe, towel, towelette, sponge, foam, mask, face mask, brush, pad, gauze, applicator, cotton ball, roll, swab, or bandage including the topical composition as described herein. In some embodiments, the patch, tape, film, wafer, wipe, paper, clothe, towel, towelette, sponge, foam, mask, or bandage is in contact with the affected area on the skin. In some embodiments, the patch, tape, film, wafer, wipe, paper, clothe, towel, towelette, sponge, foam, mask, face mask, brush, pad, gauze, applicator, cotton ball, roll, swab, or bandage, when applied to a subject, is in contact with areas of the skin of the subject that are adjacent to the affected or target area.

In some embodiments, the patch, tape, film, wafer, paper, clothe, towel, towelette, sponge, foam, mask, face mask, brush, pad, gauze, applicator, cotton ball, roll, swab, or bandage includes an adhesive.

In some embodiments, the topical composition may be applied to the skin or scalp using a tape or film which provides an occluding environment. The tape or film may be adhesive tape, waterproof adhesive tape, or a plastic film (with or without an adhesive layer).

In some embodiments, the composition is impregnated in the tape paper, clothe, towel, towelette, sponge, mask, foam, or film. In some embodiments, the tape or film is a foam-containing tape or film. Pores or interstitial spaces in the foam, paper, clothe, towel, towelette, mask, or sponge can be loaded with the composition as described herein. The foam, paper, clothe, towel, towelette, mask, or sponge can have an adhesive layer for adhering to skin. If the foam, paper, clothe, towel, towelette, mask, or sponge, is porous, an outer non-porous layer can be provided on the back of the foam, wipe, paper, clothe, towel, towelette, pad, gauze, cotton ball, swab, or sponge, to enhance tape occlusion.

In some embodiments, the composition may be a form of a slow-release paper, clothe, towel, towelette, sponge, mask, wafer or dot, may also be made by using a porous foam, may have a quantity of the composition placed behind the porous foam, and may have a non-porous backing layer placed behind the composition. The non-porous backing layer can have a portion extending beyond the composition containing the PK inhibitor, without limitation, such as ruboxistaurin free base or a ruboxistaurin salt (e.g., ruboxistaurin mesylate monohydrate) and the porous layer. This portion can include a quantity of adhesive for facilitating adhesion of the paper, clothe, towel, towelette, sponge, mask, wafer or dot to the skin of a user peripheral to the area being treated.

Methods

In another aspect, the present disclosure provides a method of treating a skin disease, condition or disorder in a subject in need thereof, the method including administering to the subject a composition, as described herein.

In some embodiments, the disease, condition or disorder is a hyperpigmentation disease condition or disorder.

In some embodiments, the compositions described herein are useful for treating hyperpigmentation disorders. In some embodiments, the hyperpigmentation disorder includes, but is not limited to: dyschromia, melasma, post inflammatory hyperpigmentation, discoid lupus erythematous, phytophotodermatitis, lentigines (e.g., age spots), birth marks, café au lait macules, acanthosis nigricans, burn associated hyperpigmentation, drug-induced hyperpigmentation (e.g., sulfonamide, tetracycline, NSAID, barbiturate, and carbamazepine induced hyperpigmentation), injury induced hyperpigmentation, primary biliary cirrhosis associated hyperpigmentation, Addison's disease associated hyperpigmentation, hemochromatosis associated hyperpigmentation, hyperthyroidism associated hyperpigmentation, melanocytic naevi, ephelides (freckles), seborrheic keratosis, skin cancer-associated hyperpigmentation, infection associated hyperpigmentation (e.g., *Pityriasis versicolor*, erythrasma), eczema, photocontact, photoallergic, or phototoxicdermatitis, ichthyosis, axillary freckling or café au lait macules associated with neurofibromatosis, or hyperpigmentation associated with ultra-violet (UV) radiation exposure, e.g., sun exposure or a tanning response, or a combination of two or more thereof. The condition may also be a condition, disease, or disorder of the hair or hair follicles and may be hirsutism/hypertrichosis and hair pigmentation. The condition may also be unwanted pigmentation of the hair or hair follicles and may be hirsutism/hypertrichosis and hair pigmentation. In particular, the compositions are useful for treating hyperpigmentation disorders and dyschromia.

In some embodiments the disorder or condition is a hair or follicle overgrowth or a hair or follicle pigmentation condition or disorder. In some embodiments hirsutsinisiypertrichosis or a hair pigmentation is the target disorder or condition. In some embodiments the disorder or condition is unwanted hair or follicle overgrowth or unwanted hair pigmentation or follicle pigmentation. In some embodiments the condition or disorder is temporary. In some embodiments the treatment for the condition or the disorder is temporary. In some embodiments the effect of the treatment is temporary.

In some embodiments, the compositions described herein are useful for treating malignant tumors. In some embodiments, the malignant tumors are malignant melanocytic tumors, malignant epidermal tumors, malignant vascular tumors, malignant metastatic tumors, malignant adipocyte tumors, malignant sebaceous tumors, or malignant fibrotic tumors. Malignant tumors include, but are not limited to, melanomas, squamous cell carcinoma, keratoacanthoma, actinic keratoses, basal cell carcinomas, angiosarcoma, Kaposi sarcoma, cutaneious breast cancer, Merkel cell cancer, liposarcoma, sebaceoma, sebaceous carcinoma, dermatofibroma sarcoma protuberens, and fibrosarcoma. In some embodiments, malignant tumors are melanomas, squamous cell carcinoma, keratoacanthoma, actinic keratoses, basal cell carcinomas, angiosarcoma, Kaposi sarcoma, cutaneious breast cancer, Merkel cell cancer, liposarcoma, sebaceoma, sebaceous carcinoma, dermatofibroma sarcoma protuberens, or fibrosarcoma.

In some embodiments, the compositions described herein are useful for treating benign tumors or skin conditions. In some embodiments, the benign tumors are benign vascular tumors, benign fibrotic tumors, benign adipocyte tumors, benign sebaceous tumors, benign epidermal tumors, benign melanocytic lesions, or benign neural tumors. Benign tumors or skin conditions include, but are not limited to, nodules, benign skin tumors, angiomas, hemangiomas, pyogenic granuloma, angiofibroma, tuberous sclerosis complex, angiomyofibroma, angiolipoma, dermatofibroma, fibroma, neurofibromas, scars, scar tissue, keloids, lipomas, acrochordons, melanoacanthoma, acanthoma, clear cell acanthoma, acanthosis nigricans, epidermoid cysts, pilar cysts, dermoid cyst, melanocytic nevi, epidermal nevi, verrucous epidermal nevi, lentigos, café au lait macules, neuroma, schwannoma, and neurolemmoma. In some embodiments, benign tumors are nodules, benign skin tumors, angiomas, hemangiomas, pyogenic granuloma, angiofibroma, tuberous sclerosis complex, angiomyofibroma, angiolipoma, dermatofibroma, fibroma, neurofibromas, scars, scar tissue, keloids, lipomas, acrochordons, melanoacanthoma, acanthoma, clear cell acanthoma, acanthosis nigricans, epidermoid cysts, pilar cysts, dermoid cyst, melanocytic nevi, epidermal nevi, verrucous epidermal nevi, lentigos, café au lait macules, neuroma, schwannoma, or neurolemmoma.

In some embodiments the compositions described herein regulate one or more of the aryl hydrocarbon receptor (AHR), aryl hydrocarbon receptor (AHR) transcription factor, CYP1A1, CYP1B1. Filaggrin, involucrin, and TGaseI, PXR, IPA, GLP-1, IL-22, 5-HT, CYP2E1, IS, cytochrome P450 enzymes, KLF6, Erα, IA, CD40, CD80, CD86, GSK-3, hedgehog, hedgehog pathway, sulfotransferases, genes involved in immune cell function and differentiation, and/or proteins involved in epidermal differentiation.

In some embodiments the composition described here may modulate epithelial function, Epithelial permeability, mucosal homeostasis, anti-oxidation, anti-inflammation, appetite, insulin secretion, gastric emptying, renal function, uremic toxins, gut immune response, skin immune response, mucosal immune response, mucosal reactivity, gastrointestinal motility, immune responses in autoimmune diseases, cancers, metabolic syndromes, mast cells, B cells, macrophages, antigen-presenting cells (APCs), Th1/Th2 cell balance, Th17, and regulatory T cells, allergens-induced diseases, and infectious diseases.

In some embodiments, the composition described herein is administered to a face of the subject. In some embodiments, the composition described herein is administered to the body of the subject. In some embodiments, the composition described herein is administered topically to the head, scalp, face, ears, neck, chest, back, inframammary regions, arms, legs, hands, fingers, feet, toes, or groin.

In some embodiments, the composition described herein is administered to a face of the subject, thereby treating hyperpigmentation of the skin or hair on the face. In some embodiments, the composition described herein is administered to the body of the subject, thereby treating hyperpigmentation of the skin or hair. In some embodiments, the composition described herein is administered topically to one or more areas selected from head, scalp, face, ears, neck, chest, back, inframammary regions, arms, legs, hands, feet, and groin, thereby treating hyperpigmentation of the skin or hair in any one of these areas.

In some embodiments the composition is applied to 0.010% to 100.00% of the body surface area. 1.0% to 90.0% of the body surface area. In some embodiments the composition is applied to 2.0% to 80.0% of the body surface area. In some embodiments the composition is applied to 3.0% to 70.0% of the body surface area. In some embodiments the composition is applied to 5.0% to 60.0% of the body surface area. In some embodiments the composition is applied to 5.0% to 50.0% of the body surface area. In some embodiments the composition is applied to 6.0% to 40.0% of the body surface area. In some embodiments the composition is applied to 7.0% to 30.0% of the body surface area. In some embodiments the composition is applied to 8.0% to 20.0% of the body surface area. In some embodiments the composition is applied to 9.0% to 15.0% of the body surface area. In some embodiments the composition is applied to approximately 10.0% of the body surface area. In some embodiments the composition is applied to approximately 15.0% of the body surface area. In some embodiments the composition is applied to approximately 20.0% of the body surface area.

In some embodiments, the skin disease, condition or disorder to be reduced, ameliorated, treated, or prevented is hyperpigmentation of the skin or hair. In some embodiments, the composition described herein is administered in an effective amount to achieve a reduction in the melanin of the skin in a treated area. In some embodiments, the composition described herein is administered in an effective amount to achieve an evenness in color of the skin in a subject. In some embodiments, the composition described herein is administered in an effective amount to lighten unwanted pigmentation, even the skin tone, make the skin monochromatic, or eliminate blemishes or irregular pigmentation of the skin of a subject measured by colorimetry, digital imaging, other objective measures, or other subjective measures in the area of treatment in a subject. In some embodiments, the composition described herein is administered in an effective amount to achieve a reduction of pigmentation or melanin in the hair produced by treated follicles.

Compositions disclosed herein may be administered as at least a single dose, multiple times a day, daily, multiple times a week, weekly, multiple times a month or monthly. In some embodiments, the composition is administered twice daily. In some embodiments, the composition is administered at least twice weekly. In some embodiments, the composition is administered at least twice monthly. In some embodiments, the composition including the compound (i.e., ruboxistaurin free base, ruboxistaurin mesylate monohydrate, or an acceptable salt thereof) in an amount of from 0.05% to 10% by weight is administered as a single dose, multiple times a day, daily, multiple times a week, weekly, twice weekly, multiple times a month, monthly, or twice monthly.

In some embodiments, the compound is administered in combination with an additional agent, e.g., a therapeutic or cosmetic agent. In some embodiments, the one or more additional agents, e.g., therapeutic agents, is chosen from: hydroquinone, indoles, indole based compounds, indole derived compounds, BIM-1, BIM-2, BIM-3, and BIM-8, bisindolylmaleimide of a derivative there of, protein kinase C inhibitors, protein kinase inhibitors, tretinoin, a corticosteroid, azaleic acid, kojic acid, a retinoid, glycolic acid, L-ascorbic acid, p-aminobenzoic acid, padimate O, phenylbenzimidazole sulfonic acid, cinoxate, menthyl anthranilate, dioxybenzone, oxybenzone, avobenzone, octisalate, octocrylene, octyl methoxycinnamate, homosalate, octinoxate, sulisobenzone, trolamine salicylate, ecamsule, zinc oxide, titanium dioxide, cosmetic agent, pigment, fragrance, sunscreen, a lathering surfactant, a vitamin, a hydroxy acid, an antioxidant, a retinoid, Arbutin 1% (a glycosylated hydroquinone), Paper mulberry 1%, Glabridin 0.5% (licorice extract), *Arctostaphylos patula* and *Arctostaphylos viscida*, Aloesin, Gentisic acid, Flavonoids, Hesperidin, Ascorbic acid or its derivative, magnesium ascorbyl phosphate 10%, Niacinamide, Yeast derivatives, Polyphenols, Soy proteins, Kojic acid 1-4% (5-hydroxy-4-pyran-4-one-2-methyl), Mequinol 5-20% (4-hydroxyanisole), Isopropylcatechol, N-acetyl-4-cysteaminylphenol, N-acetyl glucosamine, Piceatannol, a moisturizing agent, Trichloracetic acid, mercury, 1,4-Benzenediol, Quinol Benzene-1,4-diol, p-Diphenol p-Dihydroxyl benzene, Hydrochinone, p-Hydroxylphenol, Hydrochinonium, Hydroquinol, Tequinol, Monobenzyl ether of hydroquinone, and/or Cysteamine cream.

In some embodiments the additional agent is a sunscreen, sun blocker, or sun filter. The sunscreen, sun blocker, or sun filter may be but is not limited to one or more of UVA filters, Benzophenones, oxybenzone, sulisobenzone, dioxybenzone, Avobenzone, Meradimate, Bisdisulizole disodium, Diethylaminohydroxy-benzoyl hexylbenzoate, Ecamsule, Methyl anthranilate, UVB filters, PABA derivatives, padimate O, Cinnamates, Octinoxate, Cinoxate, Salicylates, octisalate, homosalate, trolamine salicylate, Octocrylene, ensulizole, ethylhexyl triazone, Broad spectrum Filters, Ecamsule, Mexoryl SX, Silatriazole, Mexoryl XL, Bemotrizinol, Tinosorb S, Bisoctrizole (Tinosorb M), Octisalate, Inorganic sunscreening agents, Zinc oxide, Titanium dioxide, Iron oxide, Red Veterinary petrolatum, Kaolin, Calamine, Ichthammol, Talc, Systemic sunscreening agents, Beta-carotene, Antimalarials, Ascorbic acid, alpha-tocopherols, Retinol, Selenium, Green tea Polyphenols, PABA, Antihistamines, Aspirin, Indomethacin, Corticosteroids, Polyhydroxystearic Acid, Organic sunscreen agents 2-ethylhexyl p-methoxycinnamate, 4,4'-t-butyl methoxydibenzoylmethane, octylsalicylate, tetraphthalylidene dicamphor sulfonic acid, benzophenone-3. In some embodiments the sunscreen, blocker, or filter is chosen from one or more of Elta MD (UV sport and UV clear), ISDIN Eryfotona, cetaphil sheer, La-Roche Posay Anthelios, and/or supergoop unseen.

In some embodiments one or more of the additional agents is a depilatory agent, a bleaching agent, or an antiaging treatment.

In some embodiments the additional agent may include but is not limited to depilatory agents, potassium or calcium thioglycolate, thioglycerol, 2-mercaptopropionic acid, monoethanolamine thioglycolic acid, homocysteine, cysteine and glutathione, inhibitors of certain enzymes such as 5-alpha reductase, ornithine decarboxylase, S-adenosylmethionine decarboxylase, gamma-glutamyl transpeptidase and transglutaminase, endothelin or its agonist, thiols, thioglycolic acid and salts thereof, thiolactic acids and salts thereof, sulfides, strontium sulfide, calcium thioglycolate, calcium hydroxide, strontium hydroxide, keratolytic agents, lactic acid, salicylic acid, glycolic acid, citric acid and malic acid.

In some embodiments the additional agent may include but is not limited hair lightening agents, alkaline agents, oxidizing agents, ethanolamine, ammonia, hydrogen peroxide ($H_2O_2$), p-phenylenediamine, p-phenylenediamine, diaminobenzene, toluene-2,5-diamine, resorcinol, persulfate salts, monoethanolamine, sodium hydrosulphite, lime juice, lemon juice, and/or citric acid.

In some embodiments the one or more additional agents can include one or more of the following but is not limited to: anti-inflammatory drugs, NSAIDs, antimicrobials, antibiotics, steroids, anti-viral agents, chemotherapy agents, alkylating agents, antimetabolites, or antimicrotubular agents, Vitamin D Derivatives, Oxidative compounds, Acids, Retinoid derivatives, Keratolytics, Corticosteroids, immunoregulators, immune modulators, sunscreens, UV blockers, zinc compounds, retinoids, dyschromia treatments, hyperpigmentation treatments, moisturizers, anti-aging treatments.

In some embodiments, the one or more additional agent is administered topically. In some embodiments, the additional agent is co-applied with the compound. In some embodiments, the additional agent and the compound are applied to a common area but at different times. In some embodiments, the additional agent and the compound are comprised in the same unit dosage form. In some embodiments, the additional agent and the compound are disposed in different unit dosage forms. In some embodiments, a second or a plurality of additional agents are administered. In some embodiments, a second administration of the compound is administered. In some embodiments, a third administration of the compound is administered.

In some embodiments, a plurality of, e.g., 2 or more, 3 or more, 4 or more, 5 or more, 6 or more, 7 or more, 8 or more, 9 or more, 10 or more, 11 or more, 12 or more, 13 or more, 14 or more, or 15 or more administrations occur in a seven day period. In some embodiments, a plurality of, e.g., 2 or more, 3 or more, 4 or more, 5 or more, 6 or more, 7 or more, 8 or more, 9 or more, 10 or more, 11 or more, 12 or more, 13 or more, 14 or more, or 15 or more administrations occur in a fourteen day period. In some embodiments, a plurality of, e.g., 2 or more, 3 or more, 4 or more, 5 or more, 6 or more, 7 or more, 8 or more, 9 or more, 10 or more, 11 or more, 12 or more, 13 or more, 14 or more, or 15 or more administrations occur in a twenty-one day period. In some embodiments, a plurality of, e.g., 2 or more, 3 or more, 4 or more, 5 or more, 6 or more, 7 or more, 8 or more, 9 or more, 10 or more, 11 or more, 12 or more, 13 or more, 14 or more, or 15 or more administrations occur in a thirty day period.

In some embodiments, the compound is administered, twice daily, daily, every other day, weekly, or monthly. In some embodiments, the compound is administered twice daily, daily, every other day, weekly, or monthly for at least 1 month, 2 months, 3 months, 4 months, 5 months, 6 months, 7 months, 8 months, 9 months, 10 months, 1 1 months, 12 months, 13 months, 14 months, 15 months, 16 months, 17 months, 18 months, 19 months, 20 months, 2 1 months, 22 months, 23 months or longer. In some embodiments, the compound is administered daily, twice daily, every other day, weekly, or monthly for at least 1, 2, 3, 4, 5, 6, 7, 8, 9, or 10 years. In some embodiments the compound is administered daily, twice daily, every other day, weekly, or monthly for at least 10 years, 20 years, 30 years, 40 years, 50 years, 60 years, 70 years, 80 years, 90 years, or the lifetime of the subject.

In some embodiments, the subject has previously been treated with the compound, e.g., had been treated for at least 1, 6, 12, 24, 36, or 48 months. In some embodiments, the subject has received one or more previous administrations of the compound, e.g., at least 2, 10, 20, 30, 40, 50, 100, 200, 300, or 500 previous administrations of the compound.

In some embodiments, the composition is administered twice daily for 4 weeks. In some embodiments, the composition is administered twice daily for 5 weeks. In some embodiments, the composition is administered twice daily for 6 weeks. In some embodiments, the composition is administered twice daily for 7 weeks. In some embodiments, the composition is administered twice daily for 8 weeks. In some embodiments, the composition is administered twice daily for 9 weeks. In some embodiments, the composition is administered twice daily for 10 weeks. In some embodiments, the composition is administered twice daily for 11 weeks. In some embodiments, the composition is administered twice daily for 12 weeks. In some embodiments, the composition is administered twice daily for 13 weeks. In some embodiments, the composition is administered twice daily for 14 weeks. In some embodiments, the composition is administered twice daily for 15 weeks. In some embodiments, the composition is administered twice daily for 16 weeks. In some embodiments, the composition is administered twice daily for 17 weeks. In some embodiments, the composition is administered twice daily for 18 weeks. In some embodiments, the composition is administered twice daily for 19 weeks. In some embodiments, the composition is administered twice daily for 20 weeks. In some embodiments, the composition is administered twice daily for 21 weeks. In some embodiments, the composition is administered twice daily for 22 weeks. In some embodiments, the composition is administered twice daily for 23 weeks. In some embodiments, the composition is administered twice daily for 24 weeks. In some embodiments, the composition is 0.8% ruboxistaurin or a salt thereof.

In some embodiments 0.01 g to 100.0 g of the composition is applied daily. In some embodiments 0.2 g to 50.0 g of the composition is applied daily. In some embodiments 0.3 g to 20.0 g of the composition is applied daily. In some embodiments 0.4 g to 15.0 g of the composition is applied daily. In some embodiments 0.5 g to 10.0 g of the composition is applied daily. In some embodiments 0.7 g to 7.0 g of the composition is applied daily. In some embodiments 0.35 g is applied twice daily. In some embodiments 0.7 g is applied daily. In some embodiments 0.7 g is applied twice daily. In some embodiments 1.0 g, 2.0 g, 3.0 g, 4.0 g, 5.0 g, 6.0 g, 7.0 g, 8.0 g, 9.0 g, or 10.0 g is applied once or twice daily. In some embodiments approximately 36.0 g is applied twice daily.

In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g of the composition is applied to 0.1% to 100.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 2.0% to 80.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 3.0% to 70.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 5.0% to 60.0% of the body surface area. In some embodiments the 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 5.0% to 50.0% of the body surface area. In some embodiments the 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 6.0% to 40.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, or 10.0 g is applied to 7.0% to 30.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 8.0% to 20.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to 9.0% to 15.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to approximately 10.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to approximately 15.0% of the body surface area. In some embodiments 0.01 g to 100.0 g, 0.2 g to 50.0 g, 0.3 g to 20.0 g, 0.4 g to 15.0 g, 0.5 g to 10.0 g, 0.7 g to 7.0 g, 0.35 g, 0.7 g, 1.0 g, 2.0 g, 3.0 g, 4.0 g, 5.0 g, 6.0 g, 7.0 g, 8.0 g, 9.0 g, 10.0 g, 20.0 g, 30.0 g, or approximately 36.0 g is applied to approximately 20.0% of the body surface area.

In some embodiments, the composition comprises 0.001 mg to 10.0 g of ruboxistaurin mesylate monohydrate, ruboxistaurin freebase, or a salt thereof. In some embodiments 0.01 mg to 5.0 g of the composition is applied daily. In some embodiments, the composition comprises 0.1 mg to 2.0 g of ruboxistaurin mesylate monohydrate, ruboxistaurin freebase, or a salt there. In some embodiments, the composition comprises 0.2 mg to 1.5 g of the ruboxistaurin mesylate monohydrate, ruboxistaurin freebase, or a salt thereof. In some embodiments, the composition comprises 0.5 mg to 1.0 g of ruboxistaurin mesylate monohydrate, ruboxistaurin freebase, or a salt thereof. In some embodiments, the composition comprises 0.7 mg to 0.7 g of ruboxistaurin mesylate monohydrate, ruboxistaurin freebase, or a salt thereof. In some embodiments, the composition comprises 0.35 g. In some embodiments, the composition comprises 0.7 g. In some embodiments, the composition comprises 0.7 g. In some embodiments, the composition comprises 1.0 mg, 2.0 mg, 3.0 mg, 4.0 mg, 5.0 mg, 6.0 mg, 7.0 mg, 8.0 mg, 9.0 mg, or 10.0 mg of ruboxistaurin mesylate monohydrate, ruboxistaurin freebase, or a salt thereof.

In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 0.1% to 100.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 2.0% to 80.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt thereof is applied to 3.0% to 70.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 5.0% to 60.0% of the body surface area. In some embodiments the 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 5.0% to 50.0% of the body surface area. In some embodiments the 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of, is applied to 6.0% to 40.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt thereof is applied to 7.0% to 30.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 8.0% to 20.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to 9.0% to 15.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to approximately 10.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to approximately 15.0% of the body surface area. In some embodiments 0.001 mg to 10.0 g, 0.01 mg to 5.0 g, 0.1 mg to 2.0 g, 0.1 mg to 2.0 g, 0.2 mg to 1.5 g, 0.5 mg to 1.0 g, 0.7 mg to 0.7 g, 0.35 mg, 0.7 mg, 1.0 mg, 2.0 mg, 3.0 mg, 4.0 mg, 5.0 mg, 5.6 mg, 6.0 mg, 7.0 mg, 8.0 mg, 9.0 mg, or 10.0 mg, of the ruboxistaurin mesylate monohydrate, ruboxistaurin freebase, or a salt there of is applied to approximately 20.0% of the body surface area.

In some embodiments, the composition is applied at an amount of about 0.00001 g per cm2 to about 0.00021 g per cm2. In some embodiments, the composition is applied at an amount of about 0.00001 g per cm2 to about 0.00003 g per cm2, about 0.00001 g per cm2 to about 0.00005 g per cm2, about 0.00001 g per cm2 to about 0.00007 g per cm2, about 0.00001 g per cm2 to about 0.00009 g per cm2, about 0.00001 g per cm2 to about 0.00011 g per cm2, about 0.00001 g per cm2 to about 0.00013 g per cm2, about 0.00001 g per cm2 to about 0.00015 g per cm2, about 0.00001 g per cm2 to about 0.00017 g per cm2, about 0.00001 g per cm2 to about 0.00019 g per cm2, about 0.00001 g per cm2 to about 0.00021 g per cm2, about 0.00003 g per cm2 to about 0.00005 g per cm2, about 0.00003 g per cm2 to about 0.00007 g per cm2, about 0.00003 g per cm2 to about 0.00009 g per cm2, about 0.00003 g per cm2 to about 0.00011 g per cm2, about 0.00003 g per cm2 to about 0.00013 g per cm2, about 0.00003 g per cm2 to about 0.00015 g per cm2, about 0.00003 g per cm2 to about 0.00017 g per cm2, about 0.00003 g per cm2 to about 0.00019 g per cm2, about 0.00003 g per cm2 to about 0.00021 g per cm2, about 0.00005 g per cm2 to about 0.00007 g per cm2, about 0.00005 g per cm2 to about 0.00009 g per cm2, about 0.00005 g per cm2 to about 0.00011 g per cm2, about 0.00005 g per cm2 to about 0.00013 g per cm2, about 0.00005 g per cm2 to about 0.00015 g per cm2, about 0.00005 g per cm2 to about 0.00017 g per cm2, about 0.00005 g per cm2 to about 0.00019 g per cm2, about 0.00005 g per cm2 to about 0.00021 g per cm2, about 0.00007 g per cm2 to about 0.00009 g per cm2, about 0.00007 g per cm2 to about 0.00011 g per cm2, about 0.00007 g per cm2 to about 0.00013 g per cm2, about 0.00007 g per cm2 to about 0.00015 g per cm2, about 0.00007 g per cm2 to about 0.00017 g per cm2, about 0.00007 g per cm2 to about 0.00019 g per cm2, about 0.00007 g per cm2 to about 0.00021 g per cm2, about 0.00009 g per cm2 to about 0.00011 g per cm2, about 0.00009 g per cm2 to about 0.00013 g per cm2, about 0.00009 g per cm2 to about 0.00015 g per cm2, about 0.00009 g per cm2 to about 0.00017 g per cm2, about 0.00009 g per cm2 to about 0.00019 g per cm2, about 0.00009 g per cm2 to about 0.00021 g per cm2, about 0.00011 g per cm2 to about 0.00013 g per cm2, about 0.00011 g per cm2 to about 0.00015 g per cm2, about 0.00011 g per cm2 to about 0.00017 g per cm2, about 0.00011 g per cm2 to about 0.00019 g per cm2, about 0.00011 g per cm2 to about 0.00021 g per cm2, about 0.00013 g per cm2 to about 0.00015 g per cm2, about 0.00013 g per cm2 to about 0.00017 g per cm2, about 0.00013 g per cm2 to about 0.00019 g per cm2, about 0.00013 g per cm2 to about 0.00021 g per cm2, about 0.00015 g per cm2 to about 0.00017 g per cm2, about 0.00015 g per cm2 to about 0.00019 g per cm2, about 0.00015 g per cm2 to about 0.00021 g per cm2, about 0.00017 g per cm2 to about 0.00019 g per cm2, about 0.00017 g per cm2 to about 0.00021 g per cm2, or about 0.00019 g per cm2 to about 0.00021 g per cm2. In some embodiments, the composition is applied at an amount of about 0.00001 g per cm2, about 0.00003 g per cm2, about 0.00005 g per cm2, about 0.00007 g per cm2, about 0.00009 g per cm2, about 0.00011 g per cm2, about 0.00013 g per cm2, about 0.00015 g per cm2, about 0.00017 g per cm2, about 0.00019 g per cm2, or about 0.00021 g per cm2. In some embodiments, the composition is applied at an amount of at least about 0.00001 g per cm2, about 0.00003 g per cm2, about 0.00005 g per cm2, about 0.00007 g per cm2, about 0.00009 g per cm2, about 0.00011 g per cm2, about 0.00013 g per cm2, about 0.00015 g per cm2, about 0.00017 g per cm2, or about 0.00019 g per cm2. In some embodiments, the composition is applied at an amount of at most about 0.00003 g per cm2, about 0.00005 g per cm2, about 0.00007 g per cm2, about 0.00009 g per cm2, about 0.00011 g per cm2, about 0.00013 g per cm2, about 0.00015 g per cm2, about 0.00017 g per cm2, about 0.00019 g per cm2, or about 0.00021 g per cm2. In some embodiments, the composition is applied at an amount of about 0.0001 g per cm2 to about 0.001 g per cm2. In some embodiments, the composition is applied at an amount of about 0.0001 g per cm2 to about 0.0002 g per cm2, about 0.0001 g per cm2 to about 0.0003 g per cm2, about 0.0001 g per cm2 to about 0.0004 g per cm2, about 0.0001 g per cm2 to about 0.0005 g per cm2, about 0.0001 g per cm2 to about 0.0006 g per cm2, about 0.0001 g per cm2 to about 0.0007 g per cm2, about 0.0001 g per cm2 to about 0.0008 g per cm2, about 0.0001 g per cm2 to about 0.0009 g per cm2, about 0.0001 g per cm2 to about 0.001 g per cm2, about 0.0002 g per cm2 to about 0.0003 g per cm2, about 0.0002 g per cm2 to about 0.0004 g per cm2, about 0.0002 g per cm2 to about 0.0005 g per cm2, about 0.0002 g per cm2 to about 0.0006 g per cm2, about 0.0002 g per cm2 to about 0.0007 g per cm2, about 0.0002 g per cm2 to about 0.0008 g per cm2, about 0.0002 g per cm2 to about 0.0009 g per cm2, about 0.0002 g per cm2 to about 0.001 g per cm2, about 0.0003 g per cm2 to about 0.0004 g per cm2, about 0.0003 g per cm2 to about 0.0005 g per cm2, about 0.0003 g per cm2 to about 0.0006 g per cm2, about 0.0003 g per cm2 to about 0.0007 g per cm2, about 0.0003 g per cm2 to about 0.0008 g per cm2, about 0.0003 g per cm2 to about 0.0009 g per cm2, about 0.0003 g per cm2 to about 0.001 g per cm2, about 0.0004 g per cm2 to about 0.0005 g per cm2, about 0.0004 g per cm2 to about 0.0006 g per cm2, about 0.0004 g per cm2 to about 0.0007 g per cm2, about 0.0004 g per cm2 to about 0.0008 g per cm2, about 0.0004 g per cm2 to about 0.0009 g per cm2, about 0.0004 g per cm2 to about 0.001 g per cm2, about 0.0005 g per cm2 to about 0.0006 g per cm2, about 0.0005 g per cm2 to about 0.0007 g per cm2, about 0.0005 g per cm2 to about 0.0008 g per cm2, about 0.0005 g per cm2 to about 0.0009 g per cm2, about 0.0005 g per cm2 to about 0.001 g per cm2, about 0.0006 g per cm2 to about 0.0007 g per cm2, about 0.0006 g per cm2 to about 0.0008 g per cm2, about 0.0006 g per cm2 to about 0.0009 g per cm2, about 0.0006 g per cm2 to about 0.001 g per cm2, about 0.0007 g per cm2 to about 0.0008 g per cm2, about 0.0007 g per cm2 to about 0.0009 g per cm2, about 0.0007 g per cm2 to about 0.001 g per cm2, about 0.0008 g per cm2 to about 0.0009 g per cm2, about 0.0008 g per cm2 to about 0.001 g per cm2, or about 0.0009 g per cm2 to about 0.001 g per cm2. In some embodiments, the composition is applied at an amount of about 0.0001 g per cm2, about 0.0002 g per cm2, about 0.0003 g per cm2, about 0.0004 g per cm2, about 0.0005 g per cm2, about 0.0006 g per cm2, about 0.0007 g per cm2, about 0.0008 g per cm2, about 0.0009 g per cm2, or about 0.001 g per cm2. In some embodiments, the composition is applied at an amount of at least about 0.0001 g per cm2, about 0.0002 g per cm2, about 0.0003 g per cm2, about 0.0004 g per cm2, about 0.0005 g per cm2, about 0.0006 g per cm2, about 0.0007 g per cm2, about 0.0008 g per cm2, or about 0.0009 g per cm2. In some embodiments, the composition is applied at an amount of at most about 0.0002 g per cm2, about 0.0003 g per cm2, about 0.0004 g per cm2, about 0.0005 g per cm2, about 0.0006 g per cm2, about 0.0007 g per cm2, about 0.0008 g per cm2, about 0.0009 g per cm2, or about 0.001 g per cm2. In some embodiments, the composition is applied at an amount of about 0.001 g per cm2 to about 0.01 g per cm2. In some embodiments, the composition is applied at an amount of about 0.001 g per cm2 to about 0.002 g per cm2, about 0.001 g per cm2 to about 0.003 g per cm2, about 0.001 g per cm2 to about 0.004 g per cm2, about 0.001 g per cm2 to about 0.005 g per cm2, about 0.001 g per cm2 to about 0.006 g per cm2, about 0.001 g per cm2 to about 0.007 g per cm2, about 0.001 g per cm2 to about 0.008 g per cm2, about 0.001 g per cm2 to about 0.009 g per cm2, about 0.001 g per cm2 to about 0.01 g per cm2, about 0.002 g per cm2 to about 0.003 g per cm2, about 0.002 g per cm2 to about 0.004 g per cm2, about 0.002 g per cm2 to about 0.005 g per cm2, about 0.002 g per cm2 to about 0.006 g per cm2, about 0.002 g per cm2 to about 0.007 g per cm2, about 0.002 g per cm2 to about 0.008 g per cm2, about 0.002 g per cm2 to about 0.009 g per cm2, about 0.002 g per cm2 to about 0.01 g per cm2, about 0.003 g per cm2 to about 0.004 g per cm2, about 0.003 g per cm2 to about 0.005 g per cm2, about 0.003 g per cm2 to about 0.006 g per cm2, about 0.003 g per cm2 to about 0.007 g per cm2, about 0.003 g per cm2 to about 0.008 g per cm2, about 0.003 g per cm2 to about 0.009 g per cm2, about 0.003 g per cm2 to about 0.01 g per cm2, about 0.004 g per cm2 to about 0.005 g per cm2, about 0.004 g per cm2 to about 0.006 g per cm2, about 0.004 g per cm2 to about 0.007 g per cm2, about 0.004 g per cm2 to about 0.008 g per cm2, about 0.004 g per cm2 to about 0.009 g per cm2, about 0.004 g per cm2 to about 0.01 g per cm2, about 0.005 g per cm2 to about 0.006 g per cm2, about 0.005 g per cm2 to about 0.007 g per cm2, about 0.005 g per cm2 to about 0.008 g per cm2, about 0.005 g per cm2 to about 0.009 g per cm2, about 0.005 g per cm2 to about 0.01 g per cm2, about 0.006 g per cm2 to about 0.007 g per cm2, about 0.006 g per cm2 to about 0.008 g per cm2, about 0.006 g per cm2 to about 0.009 g per cm2, about 0.006 g per cm2 to about 0.01 g per cm2, about 0.007 g per cm2 to about 0.008 g per cm2, about 0.007 g per cm2 to about 0.009 g per cm2, about 0.007 g per cm2 to about 0.01 g per cm2, about 0.008 g per cm2 to about 0.009 g per cm2, about 0.008 g per cm2 to about 0.01 g per cm2, or about 0.009 g per cm2 to about 0.01 g per cm2. In some embodiments, the composition is applied at an amount of about 0.001 g per cm2, about 0.002 g per cm2, about 0.003 g per cm2, about 0.004 g per cm2, about 0.005 g per cm2, about 0.006 g per cm2, about 0.007 g per cm2, about 0.008 g per cm2, about 0.009 g per cm2, or about 0.01 g per cm2. In some embodiments, the composition is applied at an amount of at least about 0.001 g per cm2, about 0.002 g per cm2, about 0.003 g per cm2, about 0.004 g per cm2, about 0.005 g per cm2, about 0.006 g per cm2, about 0.007 g per cm2, about 0.008 g per cm2, or about 0.009 g per cm2. In some embodiments, the composition is applied at an amount of at most about 0.002 g per cm2, about 0.003 g per cm2, about 0.004 g per cm2, about 0.005 g per cm2, about 0.006 g per cm2, about 0.007 g per cm2, about 0.008 g per cm2, about 0.009 g per cm2, or about 0.01 g per cm2. In some embodiments, the composition is applied at an amount of about 0.01 g per cm2 to about 0.1 g per cm2. In some embodiments, the composition is applied at an amount of about 0.01 g per cm2 to about 0.02 g per cm2, about 0.01 g per cm2 to about 0.03 g per cm2, about 0.01 g per cm2 to about 0.04 g per cm2, about 0.01 g per cm2 to about 0.05 g per cm2, about 0.01 g per cm2 to about 0.06 g per cm2, about 0.01 g per cm2 to about 0.07 g per cm2, about 0.01 g per cm2 to about 0.08 g per cm2, about 0.01 g per cm2 to about 0.09 g per cm2, about 0.01 g per cm2 to about 0.1 g per cm2, about 0.02 g per cm2 to about 0.03 g per cm2, about 0.02 g per cm2 to about 0.04 g per cm2, about 0.02 g per cm2 to about 0.05 g per cm2, about 0.02 g per cm2 to about 0.06 g per cm2, about 0.02 g per cm2 to about 0.07 g per cm2, about 0.02 g per cm2 to about 0.08 g per cm2, about 0.02 g per cm2 to about 0.09 g per cm2, about 0.02 g per cm2 to about 0.1 g per cm2, about 0.03 g per cm2 to about 0.04 g per cm2, about 0.03 g per cm2 to about 0.05 g per cm2, about 0.03 g per cm2 to about 0.06 g per cm2, about 0.03 g per cm2 to about 0.07 g per cm2, about 0.03 g per cm2 to about 0.08 g per cm2, about 0.03 g per cm2 to about 0.09 g per cm2, about 0.03 g per cm2 to about 0.1 g per cm2, about 0.04 g per cm2 to about 0.05 g per cm2, about 0.04 g per cm2 to about 0.06 g per cm2, about 0.04 g per cm2 to about 0.07 g per cm2, about 0.04 g per cm2 to about 0.08 g per cm2, about 0.04 g per cm2 to about 0.09 g per cm2, about 0.04 g per cm2 to about 0.1 g per cm2, about 0.05 g per cm2 to about 0.06 g per cm2, about 0.05 g per cm2 to about 0.07 g per cm2, about 0.05 g per cm2 to about 0.08 g per cm2, about 0.05 g per cm2 to about 0.09 g per cm2, about 0.05 g per cm2 to about 0.1 g per cm2, about 0.06 g per cm2 to about 0.07 g per cm2, about 0.06 g per cm2 to about 0.08 g per cm2, about 0.06 g per cm2 to about 0.09 g per cm2, about 0.06 g per cm2 to about 0.1 g per cm2, about 0.07 g per cm2 to about 0.08 g per cm2, about 0.07 g per cm2 to about 0.09 g per cm2, about 0.07 g per cm2 to about 0.1 g per cm2, about 0.08 g per cm2 to about 0.09 g per cm2, about 0.08 g per cm2 to about 0.1 g per cm2, or about 0.09 g per cm2 to about 0.1 g per cm2. In some embodiments, the composition is applied at an amount of about 0.01 g per cm2, about 0.02 g per cm2, about 0.03 g per cm2, about 0.04 g per cm2, about 0.05 g per cm2, about 0.06 g per cm2, about 0.07 g per cm2, about 0.08 g per cm2, about 0.09 g per cm2, or about 0.1 g per cm2. In some embodiments, the composition is applied at an amount of at least about 0.01 g per cm2, about 0.02 g per cm2, about 0.03 g per cm2, about 0.04 g per cm2, about 0.05 g per cm2, about 0.06 g per cm2, about 0.07 g per cm2, about 0.08 g per cm2, or about 0.09 g per cm2. In some embodiments, the composition is applied at an amount of at most about 0.02 g per cm2, about 0.03 g per cm2, about 0.04 g per cm2, about 0.05 g per cm2, about 0.06 g per cm2, about 0.07 g per cm2, about 0.08 g per cm2, about 0.09 g per cm2, or about 0.1 g per cm2. In some embodiments, the composition is applied at an amount of about 0.1 g per cm2 to about 1 g per cm2. In some embodiments, the composition is applied at an amount of about 0.1 g per cm2 to about 0.2 g per cm2, about 0.1 g per cm2 to about 0.3 g per cm2, about 0.1 g per cm2 to about 0.4 g per cm2, about 0.1 g per cm2 to about 0.5 g per cm2, about 0.1 g per cm2 to about 0.6 g per cm2, about 0.1 g per cm2 to about 0.7 g per cm2, about 0.1 g per cm2 to about 0.8 g per cm2, about 0.1 g per cm2 to about 0.9 g per cm2, about 0.1 g per cm2 to about 1 g per cm2, about 0.2 g per cm2 to about 0.3 g per cm2, about 0.2 g per cm2 to about 0.4 g per cm2, about 0.2 g per cm2 to about 0.5 g per cm2, about 0.2 g per cm2 to about 0.6 g per cm2, about 0.2 g per cm2 to about 0.7 g per cm2, about 0.2 g per cm2 to about 0.8 g per cm2, about 0.2 g per cm2 to about 0.9 g per cm2, about 0.2 g per cm2 to about 1 g per cm2, about 0.3 g per cm2 to about 0.4 g per cm2, about 0.3 g per cm2 to about 0.5 g per cm2, about 0.3 g per cm2 to about 0.6 g per cm2, about 0.3 g per cm2 to about 0.7 g per cm2, about 0.3 g per cm2 to about 0.8 g per cm2, about 0.3 g per cm2 to about 0.9 g per cm2, about 0.3 g per cm2 to about 1 g per cm2, about 0.4 g per cm2 to about 0.5 g per cm2, about 0.4 g per cm2 to about 0.6 g per cm2, about 0.4 g per cm2 to about 0.7 g per cm2, about 0.4 g per cm2 to about 0.8 g per cm2, about 0.4 g per cm2 to about 0.9 g per cm2, about 0.4 g per cm2 to about 1 g per cm2, about 0.5 g per cm2 to about 0.6 g per cm2, about 0.5 g per cm2 to about 0.7 g per cm2, about 0.5 g per cm2 to about 0.8 g per cm2, about 0.5 g per cm2 to about 0.9 g per cm2, about 0.5 g per cm2 to about 1 g per cm2, about 0.6 g per cm2 to about 0.7 g per cm2, about 0.6 g per cm2 to about 0.8 g per cm2, about 0.6 g per cm2 to about 0.9 g per cm2, about 0.6 g per cm2 to about 1 g per cm2, about 0.7 g per cm2 to about 0.8 g per cm2, about 0.7 g per cm2 to about 0.9 g per cm2, about 0.7 g per cm2 to about 1 g per cm2, about 0.8 g per cm2 to about 0.9 g per cm2, about 0.8 g per cm2 to about 1 g per cm2, or about 0.9 g per cm2 to about 1 g per cm2. In some embodiments, the composition is applied at an amount of about 0.1 g per cm2, about 0.2 g per cm2, about 0.3 g per cm2, about 0.4 g per cm2, about 0.5 g per cm2, about 0.6 g per cm2, about 0.7 g per cm2, about 0.8 g per cm2, about 0.9 g per cm2, or about 1 g per cm2. In some embodiments, the composition is applied at an amount of at least about 0.1 g per cm2, about 0.2 g per cm2, about 0.3 g per cm2, about 0.4 g per cm2, about 0.5 g per cm2, about 0.6 g per cm2, about 0.7 g per cm2, about 0.8 g per cm2, or about 0.9 g per cm2. In some embodiments, the composition is applied at an amount of at most about 0.2 g per cm2, about 0.3 g per cm2, about 0.4 g per cm2, about 0.5 g per cm2, about 0.6 g per cm2, about 0.7 g per cm2, about 0.8 g per cm2, about 0.9 g per cm2, or about 1 g per cm2.

In a non-limiting example, the composition is 0.8% ruboxistaurin mesylate monohydrate, 0.64% ruboxistaurin free base, 0.8% ruboxistaurin mesylate monohydrate, or a salt thereof, administered twice daily for at least 12 weeks, e.g., about 12 weeks. The ruboxistaurin may be free base. The ruboxistaurin may be ruboxistaurin mesylate monohydrate.

In another non-limiting example, the composition is 0.8% ruboxistaurin mesylate monohydrate, 0.64% ruboxistaurin free base, or a salt thereof, administered twice daily for about 4 weeks to about 8 weeks, e.g., about 4 weeks, about 5 weeks, about 6 weeks, about 7 weeks, or about 8 weeks. The ruboxistaurin free base may be ruboxistaurin mesylate monohydrate.

In another non-limiting example, the composition is 0.8% ruboxistaurin mesylate monohydrate, 0.64% ruboxistaurin free base, or a salt thereof, administered twice daily for about 8 weeks to about 12 weeks, e.g., about 8 weeks, about 9 weeks, about 10 weeks, about 11 weeks, or about 12 weeks. The ruboxistaurin free base may be ruboxistaurin mesylate monohydrate.

In some embodiments, the composition administered is in the form of a gel, cream, ointment, lotion, foam or emollient.

In some embodiments, the composition administered is a component of a patch, tape, film, wafer, wipe, paper, clothe, towel, towelette, sponge, mask, wipe, brush, pad, gauze, applicator, cotton ball, roll, swab, or bandage.

In some embodiments, the subject in need thereof is a human.

Kits

Also provided are kits for use in methods of treatment of a skin disease, condition or disorder where the subject is in need thereof with the composition as described herein in a tube, flexible aluminum tube or laminated plastic tube. The kits can include a topical composition including the compound (i.e., ruboxistaurin free base, ruboxistaurin mesylate monohydrate, or an acceptable salt thereof), a second agent or composition, and instructions providing information to a health care provider regarding usage for treating a skin disease, condition or disorder. Instructions may be provided in printed form or in the form of an electronic or digital medium such as a floppy disc, CD, or DVD, data storage device, flash drive, or in the form of a website address where such instructions may be obtained. A unit dose of a compound or a topical composition provided herein, or a second agent or composition, can include a dosage such that when administered to a subject, a therapeutically or prophylactically effective level of the compound or the topical composition can be maintained at the site of treatment in the subject for at least 1 day.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

In some embodiments the packaging is a tube or container that blocks UV light. In some embodiments the tube or container is opaque. In some embodiments the tube or container is made of a material that filters UV light and UV light is prevented from reaching the product.

In some embodiments the packaging minimizes oxygen contacting the product. In some embodiments the tube or container is vacuum sealed and any remaining air is removed from the tube or container after the filling of the tube or container with product. In some instances, the air in the head space of the tube or container is replaced with an inert gas. In some instances, the gas is nitrogen.

Exemplary Embodiments

Described below are exemplary embodiments of compositions, kits, and methods described herein:

1. A composition comprising ruboxistaurin free base or ruboxistaurin mesylate monohydrate, or a salt thereof, and a penetration enhancer and/or organic solvent.

2. The composition of embodiment 1, wherein in the total amount of penetration enhancer and/or organic solvent is about 62% to about 99% by weight of the composition.

3. The composition of embodiment 1 or embodiment 2, comprising the penetration enhancer.

4. The composition of embodiment 3, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

5. The composition of any one of embodiments 1-4, comprising the organic solvent.

6. The composition of embodiment 5, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

7. The composition of embodiment 6, wherein the organic solvent comprises propylene glycol, 2-(2-ethoxyethoxy)ethanol, glycerol, or polyethylene glycol, or a combination of two or more thereof.

8. The composition of embodiment 1 or embodiment 2, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

9. The composition of any one of embodiments 1-8, comprising the penetration enhancer.

10. The composition of embodiment 9, wherein the penetration enhancer comprises the organic solvent.

11. The composition of embodiment 1, wherein the penetration enhancer and/or organic solvent comprises propylene glycol, 2-(2-ethoxyethoxy)ethanol, glycerol, or polyethylene glycol, or a combination of two or more thereof.

12. The composition of any one of embodiments 1-11, comprising an emulsifier.

13 The composition of embodiment 12, wherein the penetration enhancer and/or organic solvent comprises the emulsifier.

14. The composition of embodiment 12 or embodiment 13, wherein the emulsifier comprises Cocoylcaprylocaprate, Decyl oleate, Diethylene glycol monoethyl ether, Dimethyl isosorbide, Glyceryl monooleate, Isopropyl myristate, medium chain triglyceride (MCT), Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

15. The composition of embodiment 1 or embodiment 2, wherein the penetration enhancer and/or organic solvent comprises diethylene glycol monoethyl ether (DGME), propylene glycol, glycerol, or polyethylene glycol, or a combination of two or more thereof.

16. The composition of embodiment 15, comprising the DGME.

17. The composition of embodiment 16, wherein the DGME is Transcutol™, transcutol HP™, or transcutol P™.

18. The composition of embodiment 17, comprising the transcutol HP™ (2-(2-ethoxyethoxy)ethanol).

19. The composition of any one of embodiments 16-18, wherein the DGME has a purity of >99.90%.

20. The composition of any one of embodiments 1-19, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

21. The composition of any one of embodiments 1-19, wherein the total amount of penetration enhancer and/or organic solvent is present at about 85% to 99% by weight of the composition.

22. The composition of any one of embodiments 1-21, further comprising an antioxidant.

23. The composition of embodiment 22, wherein the total amount of antioxidant is present in the composition at about 0.010%-1% by weight of the composition.

24. A composition comprising ruboxistaurin free base or ruboxistaurin mesylate monohydrate, or a salt thereof, and an antioxidant.

25. The composition of any one of embodiments 22-24, wherein the antioxidant comprises butylated hydroxytoluene, butylated hydroxyanisole, propyl gallate, ascorbic acid, alphatocopheryl acetate, or ascorbyl palmitate, or a combination or two or more thereof.

26. The composition of embodiment 24 or 25, wherein the total amount of antioxidant is present in the composition at about 0.2%-0.3% by weight of the composition.

27. The composition of embodiment 24 or 25, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

28. The composition of any of embodiments 1-27, further comprising an alcohol.

29. The composition of embodiment 28, wherein the total amount of alcohol is present in the composition at about 62%-99% by weight of the composition.

30. A composition comprising ruboxistaurin free base or ruboxistaurin mesylate monohydrate, or a salt thereof, and an alcohol.

31. The composition of any one of embodiments 28-30, wherein the alcohol comprises a $C_{2-6}$ alcohol.

32. The composition of any one of embodiments 28-31 wherein the alcohol comprises glycerol, ethanol, propanol, isopropanol, n-butanol, isobutanol, 2-butanol, or tert-butanol, or a combination of two or more thereof.

33. The composition of any one of embodiments 30-32, wherein the total amount of alcohol is present in the composition at about 85%-99% by weight of the composition.

34. The composition of any one of embodiments 30-32, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

35. The composition of any of embodiments 1-34 further comprising a gelling agent.

36. The composition of embodiment 35, wherein the gelling agent is about 16%-75% or about 18%-56% by weight of the composition.

37. A composition comprising ruboxistaurin free base, ruboxistaurin mesylate monohydrate, or a salt thereof, and a gelling agent.

38. The composition of any one of embodiments 35-37, wherein the gelling agent comprises hydroxypropyl cellulose, hydroxyethyl cellulose, carbopol, carbomer, or carboxymethyl cellulose, or a combination of two or more thereof.

39. The composition of embodiment 38, wherein the hydroxypropyl cellulose (HPC) is HPC GF, HPC CF, or HPC HF, or a combination of two or more thereof.

40. The composition of any one of embodiments 37 to 39, wherein the gelling agent comprises (i) glycerol present at about 12-24%, about 14-20%, about 13-17%, about 14-16%, or about 14-15% by weight of the composition, (ii) PEG present at about 2-45%, about 3-24%, about 3-14%, about 13-15%, or about 13-14% by weight of the composition, (iii) HPC present at about 0.5%-4%, or about 1-3% by weight of the composition, (iv) a combination of (i) and (ii), (v) a combination of (i) and (iii), (vi) a combination of (ii) and (iii), or (vii) a combination of (i), (ii), and (iii).

41. The composition of any one of embodiments 37-39, wherein the gelling agent has an average molecular weight of from about 700,000 Da to 1,150,000 Da.

42. A composition comprising ruboxistaurin free base or ruboxistaurin mesylate monohydrate, or a salt thereof, a penetration enhancer and/or organic solvent, and an antioxidant.

43. The composition of embodiment 42, wherein in the total amount of penetration enhancer and/or organic solvent is about 62% to about 99% by weight of the composition.

44. The composition of embodiment 42 or embodiment 43 comprising the penetration enhancer.

45. The composition of embodiment 44, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

46. The composition of any one of embodiments 42-45, comprising the organic solvent.

47. The composition of embodiment 46, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

48. The composition of embodiment 47, wherein the organic solvent comprises propylene glycol, 2-(2-ethoxyethoxy)ethanol, glycerol, or polyethylene glycol, or a combination of two or more thereof.

49. The composition of embodiment 42 or embodiment 43, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

50. The composition of any one of embodiments 42-49, comprising the penetration enhancer.

51. The composition of embodiment 50, wherein the penetration enhancer comprises the organic solvent.

52. The composition of embodiment 42, wherein the penetration enhancer and/or organic solvent comprises propylene glycol, 2-(2-ethoxyethoxy)ethanol, glycerol, or polyethylene glycol, or a combination of two or more thereof.

53. The composition of any one of embodiments 42-52, comprising an emulsifier.

54. The composition of embodiment 53, wherein the penetration enhancer and/or organic solvent comprises the emulsifier.

55. The composition of embodiment 53 or embodiment 54, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

56. The composition of embodiment 42 or embodiment 43, wherein the penetration enhancer and/or organic solvent comprises diethylene glycol monoethyl ether (DGME), propylene glycol, glycerol, or polyethylene glycol, or a combination of two or more thereof.

57. The composition of embodiment 56, comprising the DGME.

58. The composition of embodiment 57, wherein the DGME is Transcutol™, transcutol HP™, or transcutol P™.

59. The composition of embodiment 58, comprising the transcutol HP™ (2-(2-ethoxyethoxy)ethanol).

60. The composition of any one of embodiments 57-59, wherein the DGME has a purity of >99.90%.

61. The composition of any one of embodiments 42-60, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

62. The composition of any one of embodiments 42-60, wherein the total amount of penetration enhancer and/or organic solvent is present at about 85% to 99% by weight of the composition.

63. The composition of any one of embodiments 42-62, wherein the antioxidant comprises butylated hydroxytoluene, butylated hydroxyanisole, propyl gallate, ascorbic acid, alphatocopheryl acetate, or ascorbyl palmitate, or a combination of two or more thereof.

64. The composition of any one of embodiments 42-63, wherein the total amount of antioxidant is present at about 0.01% to 15%, or about 0.2% to 0.3% by weight of the composition.

65. The composition of any one of embodiments 42-63, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

66. A composition, comprising ruboxistaurin or ruboxistaurin mesylate, or a salt thereof, a penetration enhancer and/or organic solvent, one or more antioxidants, and an alcohol.

67. The composition of embodiment 66, wherein in the penetration enhancer and/or organic solvent is about 62% to about 99% by weight of the composition.

68. The composition of embodiment 66 or embodiment 67 comprising the penetration enhancer.

69. The composition of embodiment 68, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

70. The composition of any one of embodiments 66-69, comprising the organic solvent.

71. The composition of embodiment 70, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

72. The composition of embodiment 71, wherein the organic solvent comprises propylene glycol, 2-(2-ethoxyethoxy)ethanol, glycerol, or polyethylene glycol, or a combination of two or more thereof.

73. The composition of embodiment 66 or embodiment 67, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

74. The composition of any one of embodiments 66-73, comprising the penetration enhancer.

75. The composition of embodiment 74, wherein the penetration enhancer comprises the organic solvent.

76. The composition of embodiment 66 or embodiment 67, wherein the penetration enhancer and/or organic solvent comprises propylene glycol, 2-(2-ethoxyethoxy)ethanol, glycerol, or polyethylene glycol, or a combination of two or more thereof.

77. The composition of any one of embodiments 66-76, comprising an emulsifier.

78. The composition of embodiment 77, wherein the penetration enhancer and/or organic solvent comprises the emulsifier.

79. The composition of embodiment 77 or embodiment 78, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

80. The composition of embodiment 66 or embodiment 67, wherein the penetration enhancer and/or organic solvent comprises diethylene glycol monoethyl ether (DGME), propylene glycol, glycerol, or polyethylene glycol, or a combination of two or more thereof.

81. The composition of embodiment 80, comprising the DGME.

82. The composition of embodiment 81, wherein the DGME is Transcutol™, transcutol HP™, or transcutol P™.

83. The composition of embodiment 82, comprising the transcutol HP™ (2-(2-ethoxyethoxy)ethanol).

84. The composition of any one of embodiments 81-83, wherein the DGME has a purity of >99.90%.

85. The composition of any one of embodiments 66-84, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

86. The composition of any one of embodiments 66-84, wherein the total amount of penetration enhancer and/or organic solvent is present at 85% to 99% by weight of the composition.

87. The composition of any one of embodiments 66-86, wherein the antioxidant comprises butylated hydroxytoluene, butylated hydroxyanisole, propyl gallate, ascorbic acid, alphatocopheryl acetate, or ascorbyl palmitate, or a combination or two or more thereof.

88. The composition of any one of embodiments 66-87, wherein the total amount of antioxidant is present in the composition at about 0.01% to 1%, or about 0.2% to 0.3% by weight of the composition.

89. The composition of any one of embodiments 66-87, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

90. The composition of any one of embodiments 66-89, wherein the alcohol comprises a $C_{2-6}$ alcohol.

91. The composition of any one of embodiments 66-89, wherein the alcohol comprises glycerol, ethanol, propanol, isopropanol, n-butanol, isobutanol, 2-butanol, or tert-butanol.

92. The composition of any one of embodiments 66-91, wherein the alcohol is present in the composition at about 62%-99% or about 85%-99% by weight of the composition.

93. The composition of any one of embodiments 66-91, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

94. A composition, comprising ruboxistaurin free base or ruboxistaurin mesylate monohydrate, or a salt thereof, a penetration enhancer and/or organic solvent, and an alcohol.

95. The composition of embodiment 94, wherein in the total amount of penetration enhancer and/or organic solvent is about 62% to about 99% by weight of the composition.

96. The composition of embodiment 94 or embodiment 95 comprising the penetration enhancer.

97. The composition of embodiment 96, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or two or more thereof.

98. The composition of any one of embodiments 94-97, comprising the organic solvent.

99. The composition of embodiment 98, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or two or more thereof.

100. The composition of embodiment 99, wherein the organic solvent comprises propylene glycol, 2-(2-ethoxyethoxy)ethanol, glycerol, or polyethylene glycol, or a combination of two or more thereof.

1O1. The composition of embodiment 94 or embodiment 95, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

102. The composition of any one of embodiments 94-101, comprising the penetration enhancer.

103. The composition of embodiment 102, wherein the penetration enhancer comprises the organic solvent.

104. The composition of embodiment 94, wherein the penetration enhancer and/or organic solvent comprises propylene glycol, 2-(2-ethoxyethoxy)ethanol, glycerol, or polyethylene glycol, or a combination of two or more thereof.

105. The composition of any one of embodiments 94-104, comprising an emulsifier.

106. The composition of embodiment 105, wherein the penetration enhancer and/or organic solvent comprises the emulsifier.

107. The composition of embodiment 105 or embodiment 106, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

108. The composition of embodiment 94 or embodiment 95, wherein the penetration enhancer and/or organic solvent comprises diethylene glycol monoethyl ether (DGME), propylene glycol, glycerol, or polyethylene glycol, or a combination of two or more thereof.

109. The composition of embodiment 108, comprising the DGME.

110. The composition of embodiment 109, wherein the DGME is Transcutol™ Transcutol HP™, or Transcutol P™.

111. The composition of embodiment 110, comprising the Transcutol HP™ (2-(2-ethoxyethoxy)ethanol).

112. The composition of any one of embodiments 109-111, wherein the DGME has a purity of >99.90%.

113. The composition of any one of embodiments 94-112, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

114. The composition of any one of embodiments 94-112, wherein the total amount of penetration enhancer and/or organic solvent is present at about 85% to 99%, from 50% to 80%, from 50% to 70%, or about 60% by weight of the composition.

115. The composition of any one of embodiments 94-114, wherein the alcohol comprises a $C_{2-6}$ alcohol.

116. The composition of any one of embodiments 94-115, wherein the alcohol comprises glycerol, ethanol, propanol, isopropanol, n-butanol, isobutanol, 2-butanol, or tert-butanol.

117. The composition of any one of embodiments 94-116, wherein the alcohol is present in the composition at about 62%-99% or about 85-99% by weight of the composition.

118. The composition of any one of embodiments 94-117, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

119. A composition, comprising ruboxistaurin free base or ruboxistaurin mesylate monohydrate, or a salt thereof, an antioxidant, and an alcohol.

120. The composition of embodiment 119, wherein the antioxidant comprises butylated hydroxytoluene, butylated hydroxyanisole, propyl gallate, ascorbic acid, alphatocopheryl acetate, or ascorbyl palmitate, or a combination or two or more thereof.

121. The composition of embodiment 119 or 120, wherein the total amount of antioxidant is present in the composition at about 0.01% to 1%, or about 0.2% to 0.3% by weight of the composition.

122. The composition of embodiment 119 or 120, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

123. The composition of any one of embodiments 119-122, wherein the alcohol comprises a $C_{2-6}$ alcohol.

124. The composition of any one of embodiments 119-123, wherein the alcohol comprises glycerol, ethanol, propanol, isopropanol, n-butanol, isobutanol, 2-butanol, or tert-butanol.

125. The composition of any one of embodiments 119-124, wherein the alcohol is present in the composition at about 62%-99% or about 85-99% by weight of the composition.

126. The composition of any one of embodiments 119-124, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv)

127. A composition, comprising ruboxistaurin free base or ruboxistaurin mesylate monohydrate, or a salt thereof, a penetration enhancer and/or organic solvent, an antioxidant, an alcohol, and a gelling agent.

128. The composition of embodiment 127, wherein in the total amount of penetration enhancer and/or organic solvent is about 85% to about 99% by weight of the composition.

129. The composition of embodiment 127 or embodiment 128 comprising the penetration enhancer.

130. The composition of embodiment 129, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

131. The composition of any one of embodiments 127-130, comprising the organic solvent.

132. The composition of embodiment 131, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

133. The composition of embodiment 132, wherein the organic solvent comprises propylene glycol, 2-(2-ethoxyethoxy)ethanol, glycerol, or polyethylene glycol, or a combination of two or more thereof.

134. The composition of embodiment 127 or embodiment 128, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

135. The composition of any one of embodiments 127-134, comprising the penetration enhancer.

136. The composition of embodiment 135, wherein penetration enhancer comprises the organic solvent.

137. The composition of embodiment 127, wherein the penetration enhancer and/or organic solvent comprises propylene glycol, 2-(2-ethoxyethoxy)ethanol, glycerol, or polyethylene glycol, or a combination of two or more thereof.

138. The composition of any one of embodiments 127-137, comprising an emulsifier.

139. The composition of embodiment 138, wherein the penetration enhancer and/or organic solvent comprises the emulsifier.

140. The composition of embodiment 138 or embodiment 139, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

141. The composition of embodiment 127 or embodiment 128, wherein the penetration enhancer and/or organic solvent comprises diethylene glycol monoethyl ether (DGME), propylene glycol, glycerol, or polyethylene glycol, or a combination of two or more thereof.

142. The composition of embodiment 141, comprising the DGME.

143. The composition of embodiment 142, wherein the DGME is Transcutol™ Transcutol HP™, or Transcutol P™.

144. The composition of embodiment 143, comprising the Transcutol HP™ (2-(2-ethoxyethoxy)ethanol).

145. The composition of any one of embodiments 142-144, wherein the DGME has a purity of >99.90%.

146. The composition of any one of embodiments 127-145, wherein the penetration enhancer and/or organic comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

147. The composition of any one of embodiments 127-145, wherein the total amount of penetration enhancer and/or organic solvent is present at about 85% to 99% by weight of the composition.

148. The composition of any one of embodiments 127-147, wherein the antioxidant comprises butylated hydroxytoluene, butylated hydroxyanisole, propyl gallate, ascorbic acid, alphatocopheryl acetate, or ascorbyl palmitate, or a combination or two or more thereof.

149. The composition of any one of embodiments 127-148, wherein the total amount of antioxidant is present in the composition at about 0.01% to 1%, or about 0.2% to 0.3% by weight of the composition.

150. The composition of any one of embodiments 127-149, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

151. The composition of any one of embodiments 127-150, wherein the alcohol comprises a $C_{2-6}$ alcohol.

152. The composition of any one of embodiments 127-151, wherein the alcohol comprises glycerol, ethanol, propanol, isopropanol, n-butanol, isobutanol, 2-butanol, or tert-butanol.

153. The composition of any one of embodiments 127-152, wherein the alcohol is present in the composition at about 62%-99% or about 85%-99% by weight of the composition.

154. The composition of any one of embodiments 127-152, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv)

155. The composition of any one of embodiments 127-154, wherein the gelling agent comprises hydroxypropyl cellulose, hydroxyethyl cellulose, carbopol, carbomer, or carboxymethyl cellulose, or a combination of two or more thereof.

156. The composition of embodiment 155, wherein the hydroxypropyl cellulose is HPC GF, HPC CF, or HPC HF, or a combination of two or more thereof.

157. The composition of any one of embodiments 127-156, wherein the gelling agent is present in a total amount of about 16%-75% or about 18%-56% by weight of the composition; and/or the gelling agent comprises (i) glycerol present at about 12-24%, about 14-20%, about 13-17%, about 14-16%, or about 14-15% by weight of the composition, (ii) PEG present at about 2-45%, about 3-24%, about 3-14%, about 13-15%, or about 13-14% by weight of the composition, (iii) HPC present at about 0.5%-4%, or about 1-3% by weight of the composition, (iv) a combination of (i) and (ii), (v) a combination of (i) and (iii), (vi) a combination of (ii) and (iii), or (vii) a combination of (i), (ii), and (iii).

158. The composition of any one of embodiments 127-157, wherein the gelling agent has an average molecular weight of from about 700,000 Da to 1,150,000 Da.

159. A composition comprising ruboxistaurin free base or ruboxistaurin mesylate monohydrate, or a salt thereof, an antioxidant, an alcohol, and a gelling agent.

160. The composition of embodiment 159, wherein the antioxidant comprises butylated hydroxytoluene, butylated hydroxyanisole, propyl gallate, ascorbic acid, alphatocopheryl acetate, or ascorbyl palmitate, or a combination or two or more thereof.

161. The composition of embodiment 159 or 160, wherein the total amount of antioxidant is present in the composition at about 0.01% to 1%, or about 0.2% to 0.3% by weight of the composition.

162. The composition of embodiment 159 or 160, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

163. The composition of any one of embodiments 159-162, wherein the alcohol comprises a C2-6 alcohol.

164. The composition of any one of embodiments 159-163, wherein the alcohol comprises glycerol, ethanol, propanol, isopropanol, n-butanol, isobutanol, 2-butanol, or tert-butanol.

165. The composition of any one of embodiments 159-164, wherein the alcohol is present in the composition at about 62%-99% or about 85%-99% by weight of the composition.

166. The composition of any one of embodiments 159-164, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

167. The composition of any one of embodiments 159-166, wherein the gelling agent comprises hydroxypropyl cellulose, hydroxyethyl cellulose, carbopol, carbomer, or carboxymethyl cellulose, or a combination of two or more thereof.

168. The composition of embodiment 167, wherein the hydroxypropyl cellulose is HPC GF, HPC CF, or HPC HF, or a combination of two or more thereof.

169. The composition of any one of embodiments 159-168, wherein the gelling agent is present in a total amount of about 16%-75% or about 18%-56% by weight of the composition; and/or the gelling agent comprises (i) glycerol present at about 12-24%, about 14-20%, about 13-17%, about 14-16%, or about 14-15% by weight of the composition, (ii) PEG present at about 2-45%, about 3-24%, about 3-14%, about 13-15%, or about 13-14% by weight of the composition, (iii) HPC present at about 0.5%-4%, or about 1-3% by weight of the composition, (iv) a combination of (i) and (ii), (v) a combination of (i) and (iii), (vi) a combination of (ii) and (iii), or (vii) a combination of (i), (ii), and (iii).

170. The composition of any one of embodiments 159-169, wherein the gelling agent has an average molecular weight of from about 700,000 Da to 1,150,000 Da.

171. A composition comprising ruboxistaurin free base or ruboxistaurin mesylate monohydrate, or a salt thereof, a penetration enhancer and/or organic solvent, an alcohol, and a gelling agent.

172. The composition of embodiment 171, wherein in the total amount of penetration enhancer and/or organic solvent is about 62% to about 99% by weight of the composition.

173. The composition of embodiment 171 or embodiment 172, comprising the penetration enhancer.

174. The composition of embodiment 173, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

175. The composition of any one of embodiments 171-174, comprising the organic solvent.

176. The composition of embodiment 175, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

177. The composition of embodiment 176, wherein the organic solvent comprises propylene glycol, 2-(2-ethoxyethoxy)ethanol, glycerol, or polyethylene glycol, or a combination of two or more thereof.

178. The composition of embodiment 171 or embodiment 172, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

179. The composition of any one of embodiments 171-178, comprising the penetration enhancer.

180. The composition of embodiment 179, wherein the penetration enhancer comprises the organic solvent.

181. The composition of embodiment 171, wherein the penetration enhancer and/or organic solvent comprises propylene glycol, 2-(2-ethoxyethoxy)ethanol, glycerol, or polyethylene glycol, or a combination of two or more thereof.

182. The composition of any one of embodiments 171-181, comprising an emulsifier.

183. The composition of embodiment 182, wherein the penetration enhancer and/or organic solvent comprises the emulsifier.

184. The composition of embodiment 182 or embodiment 183, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

185. The composition of embodiment 171 or embodiment 172, wherein the penetration enhancer and/or organic solvent comprises diethylene glycol monoethyl ether (DGME), propylene glycol, glycerol, or polyethylene glycol, or a combination of two or more thereof.

186. The composition of embodiment 185, comprising the DGME.

187. The composition of embodiment 186, wherein the DGME is Transcutol™ Transcutol HP™, or Transcutol P™.

188. The composition of embodiment 187, comprising the Transcutol HP™ (2-(2-ethoxyethoxy)ethanol).

189. The composition of any one of embodiments 186-188, wherein the DGME has a purity of >99.90%.

190. The composition of any one of embodiments 171-189, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

191. The composition of any one of embodiments 171-189, wherein the total amount of penetration enhancer and/or organic solvent is present at about 85% to 99% by weight of the composition.

192. The composition of any one of embodiments 171-191, wherein the alcohol comprises a $C_{2-6}$ alcohol.

193. The composition of any one of embodiments 171-192, wherein the alcohol comprises glycerol, ethanol, propanol, isopropanol, n-butanol, isobutanol, 2-butanol, or tert-butanol.

194. The composition of any one of embodiments 171-193, wherein the alcohol is present in the composition at about 62%-99% or about 85%-99% by weight of the composition.

195. The composition of any one of embodiments 171-193, wherein the alcohol comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

196. The composition of any one of embodiments 171-195, wherein the gelling agent comprises hydroxypropyl cellulose, hydroxyethyl cellulose, carbopol, carbomer, or carboxymethyl cellulose, or a combination of two or more thereof.

197. The composition of embodiment 196, wherein the hydroxypropyl cellulose is HPC GF, HPC CF, or HPC HF, or a combination of two or more thereof.

198. The composition of any one of embodiments 171-197, wherein the gelling agent is present in a total amount of about 16%-75% or about 18%-56% by weight of the composition; and/or the gelling agent comprises (i) glycerol present at about 12-24%, about 14-20%, about 13-17%, about 14-16%, or about 14-15% by weight of the composition, (ii) PEG present at about 2-45%, about 3-24%, about 3-14%, about 13-15%, or about 13-14% by weight of the composition, (iii) HPC present at about 0.5%-4%, or about 1-3% by weight of the composition, (iv) a combination of (i) and (ii), (v) a combination of (i) and (iii), (vi) a combination of (ii) and (iii), or (vii) a combination of (i), (ii), and (iii).

199. The composition of any one of embodiments 171-198, wherein the gelling agent has an average molecular weight of from about 700,000 Da to 1,150,000 Da.

200. A composition comprising ruboxistaurin free base or ruboxistaurin mesylate monohydrate, or a salt thereof, a penetration enhancer and/or organic solvent, an antioxidant, and a gelling agent.

201. The composition of embodiment 200, wherein in the total amount of penetration enhancer and/or organic solvent is about 62% to about 99% by weight of the composition.

202. The composition of embodiment 200 or embodiment 201, comprising the penetration enhancer.

203. The composition of embodiment 202, wherein the penetration enhancer comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

204. The composition of any one of embodiments 200-203, comprising the organic solvent.

205. The composition of embodiment 204, wherein the organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

206. The composition of embodiment 205, wherein the organic solvent comprises propylene glycol, 2-(2-ethoxyethoxy)ethanol, glycerol, or polyethylene glycol, or a combination of two or more thereof.

207. The composition of embodiment 200 or embodiment 201, wherein the penetration enhancer and/or organic solvent comprises C2-6 alkylene glycol, C1-3 alkyl-(OCH2CH2)1-5-OH, a polyethylene glycol, glycerol, a fatty alcohol, a fatty ester, or a fatty ether, or a combination of two or more thereof.

208. The composition of any one of embodiments 200-207, comprising the penetration enhancer.

209. The composition of embodiment 208, wherein the penetration enhancer comprises the organic solvent.

210. The composition of embodiment 200, wherein the penetration enhancer and/or organic solvent comprises propylene glycol, 2-(2-ethoxyethoxy)ethanol, glycerol, or polyethylene glycol, or a combination of two or more thereof.

211. The composition of any one of embodiments 200-210, comprising an emulsifier.

212. The composition of embodiment 211, wherein the penetration enhancer and/or organic solvent comprises the emulsifier.

213. The composition of embodiment 211 or embodiment 212, wherein the emulsifier comprises Cocoylcaprylocaprate, Decyl oleate, Diethylene glycol monoethyl ether, Dimethyl isosorbide, Glyceryl monooleate, Isopropyl myristate, MCT, Octyldodecanol, Oleyl alcohol, Oleyl oleate, Polyoxyethylene alkyl ethers, Polyoxyethylene stearates, Propylene glycol monolaurate, Propylene glycol, Lecithin, cyclodextrins, docusate sodium, glyceryl monostearate, hydrogenated vegetable/cottonseed/palm kernel oil, MCT, N-methyl-2-pyrrolidone, poloxamer, PEG, polysorbates, PEG castor oil derivatives, propylene glycol, polyoxylglycerides, sodium lauryl sulfate, sucrose esters, or glycerol, or a combination of two or more thereof.

214. The composition of embodiment 200 or embodiment 201, wherein the penetration enhancer and/or organic solvent comprises diethylene glycol monoethyl ether (DGME), propylene glycol, glycerol, or polyethylene glycol, or a combination of two or more thereof.

215. The composition of embodiment 214, comprising the DGME.

216. The composition of embodiment 215, wherein the DGME is Transcutol™ Transcutol HP™, or Transcutol P™.

217. The composition of embodiment 216, comprising the Transcutol HP™ (2-(2-ethoxyethoxy)ethanol).

218. The composition of any one of embodiments 215-217, wherein the DGME has a purity of >99.90%.

219. The composition of any one of embodiments 200-218, wherein the penetration enhancer and/or organic solvent comprises (i) DGME present at about 40-50%, about 43-49%, about 47-49%, or about 47-48% by weight of the composition, (ii) PEG present at about 2-45%, about 3-24%, about 3-14%, about 13-15%, or about 13-14% by weight of the composition, (iii) glycerol present at about 12-24%, about 14-20%, about 13-17%, about 14-16%, or about 14-15% by weight of the composition, (iv) propylene glycol at about 8-30%, about 9-22%, about 18-22%, about 19-21% or about 19-20% by weight of the composition, (v) a combination of (i) and (ii), (vi) a combination of (i) and (iii), (vii) a combination of (i) and (iv), (viii) a combination of (ii) and (iii), (ix) a combination of (ii) and (iv), (x) a combination of (iii) and (iv), (xi) a combination of (i), (ii), and (iii), (xii) a combination of (i), (ii), and (iv), (xiii) a combination of (i), (iii), and (iv), (xiv) a combination of (ii), (iii), and (iv), or (vx) a combination of (i), (ii), (iii) and (iv).

220. The composition of any one of embodiments 200-218, wherein the total amount of penetration enhancer and/or organic solvent is present at about 85% to 99% by weight of the composition.

221. The composition of any one of embodiments 200-220, wherein the antioxidant comprises butylated hydroxytoluene, butylated hydroxyanisole, propyl gallate, ascorbic acid, alphatocopheryl acetate, or ascorbyl palmitate, or a combination or two or more thereof.

222. The composition of any one of embodiments 200-221, wherein the total amount of antioxidant is present in the composition at about 0.01% to 1%, or about 0.2% to 0.3% by weight of the composition.

223. The composition of any one of embodiments 200-221, wherein the antioxidant comprises butylated hydroxytoluene (BHT) present about 0.05-0.3%, about 0.1, or about 0.2%, and/or comprises butylated hydroxyanisole (BHA) present at about 0.05-0.2% or about 0.1% by weight of the composition.

224. The composition of any one of embodiments 200-223, wherein the gelling agent comprises hydroxypropyl cellulose, hydroxyethyl cellulose, carbopol, carbomer, or carboxymethyl cellulose, or a combination of two or more thereof.

225. The composition of embodiment 224, wherein the hydroxypropyl cellulose is HPC GF, HPC CF, or HPC HF, or a combination of two or more thereof.

226. The composition of any one of embodiments 200-225, wherein the gelling agent is present in a total amount of about 16%-75% or about 18%-56% by weight of the composition; and/or the gelling agent comprises (i) glycerol present at about 12-24%, about 14-20%, about 13-17%, about 14-16%, or about 14-15% by weight of the composition, (ii) PEG present at about 2-45%, about 3-24%, about 3-14%, about 13-15%, or about 13-14% by weight of the composition, (iii) HPC present at about 0.5%-4%, or about 1-3% by weight of the composition, (iv) a combination of (i) and (ii), (v) a combination of (i) and (iii), (vi) a combination of (ii) and (iii), or (vii) a combination of (i), (ii), and (iii).

227. The composition of any one of embodiments 200-226, wherein the gelling agent has an average molecular weight of from about 700,000 Da to 1,150,000 Da.

228. A composition comprising (i) ruboxistaurin free base or ruboxistaurin mesylate monohydrate, or a salt thereof, and (ii) PEG, propylene glycol, 2-(2-ethoxyethoxy)ethanol, butylated hydroxytoluene, butylated hydroxyanisole, glycerol, or hydroxypropyl cellulose, or two or more thereof.

229. The composition of any one of embodiments 1-228, comprising PEG, propylene glycol, 2-(2-ethoxyethoxy)ethanol, butylated hydroxytoluene, butylated hydroxyanisole, glycerol, or hydroxypropyl cellulose, or two or more thereof.

230. The composition of embodiment 228 or embodiment 229, wherein
(a) the PEG is present in an amount of from 10% to 30%, from 10% to 20%, or about 14% by weight of the composition;
(b) the propylene glycol is present in an amount of from 10% to 40%, from 15% to 30%, or about 20% by weight of the composition;
(c) the 2-(2-ethoxyethoxy)ethanol is present in an amount of from 30% to 70%, from 40% to 60%, or about 47% by weight of the composition;
(d) the butylated hydroxytoluene is present in an amount of from 0.01% to 0.5%, from 0.01% to 0.2%, from 0.01% to 0.1%, or about 0.1% by weight of the composition;
(e) the butylated hydroxyanisole is present in an amount of from 0.01% to 0.5%, from 0.01% to 0.2%, from 0.01% to 0.1%, or about 0.1% by weight of the composition;
(f) the glycerol is present in an amount of from 5% to 25%, from 10% to 20%, or about 15% by weight of the composition; or
(g) the hydroxypropyl cellulose is present in an amount of from 1% to 4% or about 3% by weight of the composition, or
(h) any combination of (a)-(g).

231. The composition of any one of embodiments 228-230, comprising the hydroxypropyl cellulose, wherein the hydroxypropyl cellulose has an average molecular weight of from about 700,000 Da to 1,150,000 Da.

232. The composition of any one of embodiments 228-231, comprising the PEG, wherein PEG is present in an amount of about 14% by weight of the composition.

233. The composition of any one of embodiments 228-232, comprising the propylene glycol, wherein the propylene glycol is present in an amount of about 20% by weight of the composition.

234. The composition of any one of embodiments 228-233, comprising the 2-(2-ethoxyethoxy)ethanol, wherein the 2-(2-ethoxyethoxy)ethanol is present in an amount of about 47% by weight of the composition.

235. The composition of any one of embodiments 228-234, comprising the butylated hydroxytoluene, wherein the butylated hydroxytoluene is present in an amount of about 0.1% by weight of the composition.

236. The composition of any one of embodiments 228-235, comprising the butylated hydroxyanisole, wherein the butylated hydroxyanisole is present in an amount of about 0.1% by weight of the composition.

237. The composition of any one of embodiments 228-236, comprising the glycerol, wherein the glycerol is present in an amount of about 15% by weight of the composition.

238. The composition of any one of embodiments 228-237, comprising the hydroxypropyl cellulose, wherein the hydroxypropyl cellulose is present in an amount of about 3% by weight.

239. The composition of embodiments 1-238, wherein the ruboxistaurin free base, ruboxistaurin mesylate monohydrate, or salt thereof is present in an amount of from 0.10% to 10.0%, from 0.5% to 5%, from 0.5% to 2%, or about 1% by weight of the composition.

240. The composition of embodiment 239, wherein the ruboxistaurin free base, ruboxistaurin mesylate monohydrate, or salt thereof is present in an amount of about 1% by weight of the composition.

241. The composition of embodiment 239, wherein the ruboxistaurin free base, ruboxistaurin mesylate monohydrate, or a salt thereof is present in an amount of about 0.6% by weight of the composition.

242. The composition of embodiment 239, wherein the ruboxistaurin free base, ruboxistaurin mesylate monohydrate, or a salt thereof is present in an amount of about 0.8% by weight of the composition.

243. The composition of any of embodiments 1 to 242, where the composition is formulated as pharmaceutical composition.

244. The composition of any of embodiments 1 to 242 wherein the composition is formulated as a cosmetic composition.

245. The composition of any of embodiments 1 to 242, where the composition is formulated as a topical pharmaceutical composition or a topical cosmetic composition.

246. The composition of any one of embodiments 1 to 245, in the form of a gel, ointment, cream, lotion, foam or emollient.

247. The composition of any one of embodiments 1 to 245, as a component of a patch, tape, film, cloth, towelette, sponge, wafer, face mask, wipe, brush, pad, gauze, applicator, cotton ball, roll, swab, or bandage.

248. A method of treating a disease, condition, or disorder in a subject in need thereof, comprising administering to the subject the composition of any one of embodiments 1 to 247.

249. The method of embodiment 248, wherein the disease, condition or disorder is a skin disease, condition, or disorder comprising hyperpigmentation, dyschromia, melasma, post inflammatory hyperpigmentation, discoid lupus erythematous, phytophotodermatitis, lentigines (e.g., age spots), birth marks, café au lait macules, acanthosis nigricans, burn associated hyperpigmentation, drug-induced hyperpigmentation (e.g., sulfonamide, tetracycline, NSAID, barbiturate, and carbamazepine induced hyperpigmentation), injury induced hyperpigmentation, primary biliary cirrhosis associated hyperpigmentation, Addison's disease associated hyperpigmentation, hemochromatosis associated hyperpigmentation, hyperthyroidism associated hyperpigmentation, melanocytic naevi, ephelides (freckles), seborrheic keratosis, skin cancer-associated hyperpigmentation, infection associated hyperpigmentation (e.g., *Pityriasis versicolor*, erythrasma), eczema, photocontact, photoallergic, or phototoxicdermatitis, ichthyosis, axillary freckleing or café aulait macules associated with neurofibromatosis, or hyperpigmentation associated with ultra-violet (UV) radiation exposure, e.g., sun exposure or a tanning response, or a combination of two or more thereof.

250. The method of embodiment 248, wherein the disease, condition or disorder comprises a hyperpigmentation disorder.

251. The method of embodiment 248, wherein the disease, condition, or disorder comprises hirsutism/hypertrichosis or a hair pigmentation.

252. The method of any one of embodiments 247-250, wherein the composition is in the form of a gel, ointment, cream, lotion, foam or emollient.

253. The method of any one of embodiments 248-251, wherein the composition is a component of a patch, tape, film, cloth, towelette, sponge, wafer, or bandage.

254. The method of any one of embodiments 248-253, wherein the composition is applied topically to the head, scalp, face, ears, neck, chest, back, inframammary regions, arms, legs, or groin.

255. The method of any one of embodiments 248-254, wherein the composition is administered twice daily.

256. The method of any one of embodiments 248-255, wherein the composition is administered for at least 12 weeks.

257. The method of any one of embodiments 248-256, wherein the composition is administered for about 12 weeks to about 24 weeks.

258. The method of any one of embodiments 248-257, wherein the composition is administered for about 12 weeks.

259. The method of any one of embodiments 248-255, wherein the composition is administered for at least 4 weeks.

260. The method of any one of embodiments 248-255, wherein the composition is administered for about 4 weeks to about 8 weeks.

261. The method of any one of embodiments 248-255, wherein the composition is administered for about 4 weeks to about 6 weeks.

262. The method of any one of embodiments 248-255, wherein the composition is administered for about 4 weeks, about 5 weeks, about 6 weeks, about 7 weeks, or about 8 weeks.

263. The method of any one of embodiments 248-255, wherein the composition is administered for about 8 weeks to about 12 weeks.

264. A kit comprising a composition of any one of embodiments 1 to 247, in a tube, flexible aluminum tube or laminated plastic tube, with instructions for use.

265. A kit comprising the composition of any one of embodiments 1 to 247, in a container or tube, flexible aluminum tube, or laminated plastic tube, that blocks Ultraviolet light from the composition.

266. A kit comprising a composition of any one of embodiments 1 to 247, in a container, tube, or pump, wherein oxygen is prevented from contacting the composition.

267. The kit of embodiment 266, wherein the container, tube, or pump, is vacuum sealed.

268. The kit of embodiment 266 or embodiment 267, wherein the container, tube, or pump headspace is filled with an inert gas to prevent oxidation.

269. The kit of embodiment 268, wherein the gas used is nitrogen.

EXAMPLES

Example 1: Preparation of Compositions

The topical compositions of the present disclosure can be prepared according to the procedure provided below. Reaction conditions, steps and reactants not provided in the procedure below would be apparent to, and known by, those skilled in the art.

Excipients (i.e., an organic solvent and/or a penetration enhancer, an antioxidant, alcohol) were aliquoted or weighted into individual vessels to form a mixture. The compound (i.e., ruboxistaurin free base, ruboxistaurin mesylate monohydrate, or an acceptable salt thereof) was added to the mixture to achieve a desired concentration. Then the gelling agent (e.g., HPC) was added accordingly. In some of the compositions, a second addition of water (if present) was finally used to titrate the composition to 100% by weight. The final mixture was then mixed well to form the composition.

Example 2: Various Compositions with/without Ruboxistaurin Free Base, Ruboxistaurin Mesylate Monohydrate, or an Acceptable Salt Thereof The following compositions were prepared according to the general procedure of Example 1 using excipients of Table 1 and 2.

TABLE 1

Various Compositions of solvent systems with and without Ruboxistaurin (PBO = placebo)

| Excipients | NA01 PBO | NA01v1 PBO | NA01v2 PBO | NA01v3 PBO | NA01v4 PBO | NA01 ACT 60% Sat Sol | NA01 ACT 80% Sat Sol | NA01 ACT original API Loading |
|---|---|---|---|---|---|---|---|---|
| SR PEG 400 (pH 5.5) | 13.97 | 14.57 | 14.57 | 13.97 | 14.57 | 13.85 | 13.81 | 13.79 |
| Transcutol P | 47.89 | 47.82 | 47.82 | 47.89 | 47.82 | 47.46 | 47.32 | 47.26 |
| Ethanol | 9.98 | 10.41 | 10.41 | 9.98 | 10.41 | 9.89 | 9.86 | 9.85 |
| Glycerol | 14.97 | 15.60 | 15.60 | 14.97 | 15.60 | 14.83 | 14.79 | 14.77 |
| Propylene Glycol | 9.98 | 10.41 | 10.41 | 9.98 | 10.41 | 9.89 | 9.86 | 9.85 |
| Ascorbic Acid | 0.20 | 0.20 | 0.20 | 0.20 | 0.20 | 0.20 | 0.20 | 0.20 |
| HPC GF | 3.00 | 1.00 | | | | 3.00 | 3.00 | 3.00 |
| HPC HF | | | 1.00 | | | | | |
| Sepineo DERM | | | | 3.00 | | | | |
| Carbopol 974 | | | | | 1.00 | | | |
| Ruboxistaurin MM | | | | | | 0.87 | 1.15 | 1.28 |
| Ruboxistaurin FB (free base) equivalent | | | | | | 0.70 | 0.93 | 1.03 |
| Total | 100.00 | 100.00 | 100.00 | 100.00 | 100.00 | 100.00 | 100.00 | 100.00 |

In accordance with Table 1, the following concentrations of excipients are provided in example formulations herein (for instance, within about +/− of values in Table 1): about 40-50% Transcutol (example solvent and/or penetration enhancer, alcohol), about 8-12% propylene glycol (example solvent and/or penetration enhancer, alcohol), about 8-12% ethanol (example solvent and/or penetration enhancer, alcohol), about 12-18% glycerol (example solvent and/or penetration enhancer, alcohol, gelling agent), about 12-16% PEG (example solvent and/or penetration enhancer, alcohol, gelling agent), about 0.5%-~4% HPC (example gelling agent), about 24% Sepineo (example gelling agent), about 0.5-2% Carbopol (example gelling agent), and about 0.1-0.3% ascorbic acid (example antioxidant); wherein each of the excipients may be optional In some cases, the composition comprises an organic solvent and/or penetration enhancer, and optionally the organic solvent and/or penetration enhancer is an alcohol and/or gelling agent; wherein optionally the total amount of organic solvent and/or penetration enhancer in the composition is about 80-100%, or about 95-99% of the composition. In some cases, the composition comprises an alcohol, and optionally the alcohol is an organic solvent/penetration enhancer and/or gelling agent; wherein optionally the total amount of alcohol in the composition is about 80-100%, or about 95-99% of the composition. In some cases, the composition comprises an antioxidant; wherein optionally the total amount of the antioxidant is about 0.1-0.3%, or about 0.2% of the composition. In some cases, the composition comprises a gelling agent; wherein optionally the total amount of the gelling agent is about 28-48% of the composition, or about 31-32% of the composition. Accordingly, disclosed herein are compositions comprising the above example amounts of solvent and/or penetration enhancer, alcohol, gelling agent, and antioxidant, alone and in combination.

TABLE 2

Various Compositions of Ruboxistaurin mesylate monohydrate in excipients

| | Solvent system composition (% w/w) | | | | | | | | | |
|---|---|---|---|---|---|---|---|---|---|---|
| Component | SSNA01 | SSNA06 | SSNA07 | SSNA08 | SSNA09 | SSNA10 | SSNA11 | SSNA12 | SSNA13 | SSNA14 |
| Ruboxistaurin MM | 0.100 | 0.100 | 0.100 | 0.100 | 0.100 | 0.100 | 0.100 | 0.100 | 0.100 | 0.100 |
| SR PEG 400 (pH adjusted to 5.5 with lactic acid and PEG) | 13.790 | 13.790 | 13.790 | 13.790 | — | — | 13.790 | — | — | 13.790 |

TABLE 2-continued

Various Compositions of Ruboxistaurin mesylate monohydrate in excipients

| | Solvent system composition (% w/w) | | | | | | | | | |
|---|---|---|---|---|---|---|---|---|---|---|
| Component | SSNA01 | SSNA06 | SSNA07 | SSNA08 | SSNA09 | SSNA10 | SSNA11 | SSNA12 | SSNA13 | SSNA14 |
| SR PEG 400 | — | — | — | — | 3.790 | 3.790 | — | — | 13.790 | — |
| Transcutol HP | 47.260 | 47.370 | 47.270 | 47.282 | 47.370 | 47.370 | 47.320 | 47.370 | 47.370 | 47.200 |
| Ethanol | 9.850 | 9.850 | 9.850 | 9.850 | 9.850 | 9.850 | 9.850 | 9.850 | 9.850 | 9.850 |
| Glycerol | 14.770 | 14.770 | 14.770 | 14.770 | 14.770 | 14.770 | 14.770 | 20.000 | 14.770 | 14.770 |
| Propylene glycol | 9.850 | 9.850 | 9.850 | 9.850 | 9.850 | 9.850 | 9.850 | 18.407 | 9.850 | 9.850 |
| EDTA disodium | — | — | — | — | — | — | — | — | — | — |
| Ascorbic acid | 0.200 | — | — | — | — | — | — | — | — | — |
| BHT | — | 0.100 | 0.100 | — | 0.100 | 0.100 | 0.100 | 0.100 | 0.100 | 0.100 |
| BHA | — | — | 0.100 | — | — | — | — | — | — | 0.100 |
| Propyl gallate | — | — | — | — | — | — | 0.050 | — | — | 0.050 |
| Alpha-tocopheryl acetate | — | — | — | 0.002 | — | — | — | — | — | 0.002 |
| Ascorbyl palmitate | — | — | — | 0.020 | — | — | — | — | — | 0.020 |
| pH adjustment | — | — | — | — | pH adjust to 5.5 | pH adjust to 4 | — | — | — | — |
| Q.S. to 95.83% | — | — | — | — | Q.S. with SR PEG400 | Q.S. with SR PEG400 | — | — | — | — |
| Total | 95.82 | 95.83 | 95.83 | 95.66 | 95.83 | 95.83 | 95.83 | 95.83 | 95.83 | 95.83 |

In accordance with Table 2, the following concentrations of excipients are provided in example formulations herein (for instance, in some cases within about +/−10-20% of values in Table 2): about 40-50% Transcutol (example solvent and/or penetration enhancer, alcohol), about 8-12% propylene glycol (example solvent and/or penetration enhancer, alcohol), about 8-12% ethanol (example solvent and/or penetration enhancer, alcohol), about 12-18% glycerol (example solvent and/or penetration enhancer, alcohol, gelling agent), about 12-16% PEG (example solvent and/or penetration enhancer, alcohol, gelling agent), about 0.1-0.3% ascorbic acid (example antioxidant), about 0.05-0.2% BHT (example antioxidant), about 0.05-0.2% BHA (example antioxidant), about 0.025-0.1% Propyl gallate (example antioxidant), about 0.001-0.003% alpha-tocopheryl acetate (example antioxidant), about 0.01-0.03% ascorbyl palmitate (example antioxidant); wherein each of the excipients may be optional. In some cases, the composition comprises an organic solvent and/or penetration enhancer, and optionally the organic solvent and/or penetration enhancer is an alcohol and/or gelling agent; wherein optionally the total amount of organic solvent and/or penetration enhancer in the composition is about 80-100%, or about 85-96% of the composition. In some cases, the composition comprises an alcohol, and optionally the alcohol is an organic solvent/penetration enhancer and/or gelling agent; wherein optionally the total amount of alcohol in the composition is about 80-100%, or about 85-96% of the composition. In some cases, the composition comprises an antioxidant; wherein optionally the total amount of the antioxidant is about 0.3-0.9%, or about 0.1-0.3% of the composition. In some cases, the composition comprises a gelling agent; wherein optionally the total amount of the gelling agent is about 24-34% of the composition, or about 18-29% of the composition. Accordingly, disclosed herein are compositions comprising the above example amounts of solvent and/or penetration enhancer, alcohol, gelling agent, and antioxidant, alone and in combination.

Example 3: A 14-Day Explant Study

Summary

A skin lightening assay was performed to demonstrate the pharmacodynamic activity of the formulations containing ruboxistaurin mesylate monohydrate. To assess the skin lightening potential of these formulations, method development experiments were performed.

The method development experiment consisted of a single formulation, a basolateral treatment, and an untreated control using dark skin. Topical formulation or basolateral treatment were applied daily for 7 days, with each treatment or media change preceded by a detergent/water wash to prevent formulation buildup (untreated control was washed in the same manner).

Materials & Methods

For the method development study, one topical and one basolateral treatment were used for the method development experiment in conjunction with an untreated control. Freshly excised skin from a darkly pigmented donor was obtained and cultured according to developed long term explant conditions at n=3. The explants were cultured for a total of 14 days and the following treatment regiments were utilized: Untreated control, basolateral treatment (API in media every 48 hours at 17.7 nM), and NA18 applied topically. Explants were treated for 7 consecutive days and maintained for an additional 7 days with no treatments. Prior to each treatment, each explant was washed with a water/detergent solution. All explants were washed with water/detergent every 2-3 days during the nontreatment phase as well, per procedure for long term culture. Pictures were taken at days 0, 7, and 14 for visual assessment of the skin lightening effects of formulation. At days 7 and 14, sets of samples (n=3) were collected for analysis of tyrosinase activity and melanin content using the procedure outlined in the study plan.

Results, Interpretations and Conclusions

Methods Development

Compared to untreated control, topical treatment with NA18 significantly reduced melanin content (p=0.023) and resulted in a visible color change after 7 days, while basolateral treatment did not appear to affect melanin content or skin color, possibly due to lack of engagement at the target site (epidermis). There was no significant difference in tyrosinase activity in either of the 2 treatment regimens compared to untreated control.

TABLE 3 mean cumulative melanin concentration (μg/mg tissue) 7 and 14 days after treatment.

| Treatment | ug melanin/mg epidermis | | | | | |
|---|---|---|---|---|---|---|
| | Day 7 | | | Day 14 | | |
| (NA18) | N | Mean | Std Dev | N | Mean | Std Dev |
| Basolateral | 3 | 39.090 | 13.821 | 3 | 20.159 | 5.992 |
| Topical | 3 | 12.255 | 5.240 | 3 | 9.834 | 2.051 |
| Untreated | 3 | 47.442 | 13.557 | 3 | 20.983 | 5.556 |

Example 4: Further Optimization of Compositions Containing High Transcutol

The compositions of % Table 2 that contain about 47-48% Transcutol P ((2-(2-ethoxyethoxy)ethanol) were further studied with additions of antioxidants (e.g., butylated hydroxytoluene (BHT) and/or butylated hydroxyanisole (BHA), or propyl gallate), preservatives (e.g., phenoxyethanol), alcohol, a gelling agent and/or a pH adjuster (e.g., aq. citric acid solution) and/or preservatives (e.g., phenoxyethanol). Accordingly, the compositions are shown in Table 5 and Table 6.

TABLE 5

Compositions including Ruboxistaurin mesylate monohydrate
Active compositions (% w/w)

| Excipients | NA13 | NA16 | NA17 | NA18 | NA19 | NA20 | NA21 | NA22 | NA23 | NA24 |
|---|---|---|---|---|---|---|---|---|---|---|
| Ruboxistaurin MM | 0.797 | NA | 0.797 | 0.797 | 0.797 | 0.797 | 0.797 | 0.100 | 0.100 | NA |
| SR PEG 400 | 3.859 | | 13.859 | 13.859 | 14.147 | 14.147 | 13.859 | 13.960 | 14.248 | 23.732 |
| Transcutol HP | 47.605 | 47.370 | 47.605 | 47.504 | 48.596 | 48.596 | 47.504 | 47.950 | 48.940 | 47.555 |
| Glycerol | 14.843 | 20.000 | 14.843 | 14.843 | 15.151 | 15.151 | 14.843 | 14.951 | 15.260 | 14.828 |
| Propylene Glycol | 19.797 | 28.257 | 19.797 | 19.797 | 20.211 | 20.211 | 19.797 | 19.941 | 20.353 | 9.888 |
| BHT | 0.100 | 0.100 | 0.100 | 0.100 | 0.100 | 0.100 | 0.200 | 0.100 | 0.100 | 0.200 |
| BHA | | | | 0.100 | | | | | | |
| HPC GF | 3.00 | 3.00 | 3.00 | 3.000 | | | 3.00 | 3.00 | | 3.000 |
| HPC HF | | | | | | 1.00 | | | | |
| Carbopol 974 | | | | | 1.00 | | | | 1.00 | |
| pH adjustment | pH adjust to 5.5 | | | | | | | | | |
| Q.S.to 100% | Q.S. with SRPEG400 | | | | | | | | | |
| Total | 100.00 | 100.00 | 100.00 | 100.00 | 100.00 | 100.00 | 100.00 | 100.00 | 100.00 | 100.00 |

TABLE 6

Further Compositions containing Ruboxistaurin mesylate monohydrate

| Excipients | NA1 modified control | NA13 | NA16 | NA17 | NA18 | NA19 | NA20 | NA21 | NA22 | NA25 | NA26 | NA28 |
|---|---|---|---|---|---|---|---|---|---|---|---|---|
| Ruboxistaurin MM | 0.80 | 0.80 | 0.83 | 0.80 | 0.80 | 0.80 | 0.80 | 0.80 | 0.10 | 0.75 | 0.79 | 0.10 |
| SR PEG 400 (pH 5.5) | 13.86 | — | — | — | — | — | — | — | — | — | — | — |
| SR PEG 400 | — | 3.86 | — | 13.86 | 13.86 | 14.15 | 14.15 | 13.86 | 13.96 | 39.55 | 13.91 | — |
| Transcutol HP | 47.50 | 47.60 | 47.59 | 47.60 | 47.50 | 48.60 | 48.60 | 47.50 | 47.95 | 43.07 | 47.78 | 48.32 |
| Ethanol | 9.90 | — | — | — | — | — | — | — | — | — | 5.04 | — |
| Glycerol | 14.84 | 14.84 | 20.09 | 14.84 | 14.84 | 15.15 | 15.15 | 14.84 | 14.95 | 13.43 | 14.90 | 20.09 |
| Propylene glycol | 9.90 | 19.80 | 28.39 | 19.80 | 19.80 | 20.21 | 20.21 | 19.80 | 19.94 | — | 14.48 | 28.39 |
| Ascorbic acid | 0.20 | — | — | — | — | — | — | — | — | — | — | — |

TABLE 6-continued

Further Compositions containing Ruboxistaurin mesylate monohydrate

| Excipients | NA1 modified control | NA13 | NA16 | NA17 | NA18 | NA19 | NA20 | NA21 | NA22 | NA25 | NA26 | NA28 |
|---|---|---|---|---|---|---|---|---|---|---|---|---|
| BHT | — | 0.10 | 0.10 | 0.10 | 0.10 | 0.10 | 0.10 | 0.20 | 0.10 | 0.20 | 0.10 | 0.10 |
| BHA | — | — | — | — | 0.10 | — | — | — | — | — | — | — |
| HPC GF | 3.00 | 3.00 | 3.00 | 3.00 | 3.00 | — | — | 3.00 | 3.00 | 3.00 | 3.00 | 3.00 |
| HPC HF | — | — | — | — | — | — | 1.00 | — | — | — | — | — |
| Carbopol 974 | — | — | — | — | — | 1.00 | — | — | — | — | — | — |
| pH adjustment | — | pH adjust to 5.5 | — | — | — | — | — | — | — | — | — | — |
| Q.S. to 100% | — | Q.S. with SRPEG400 | — | — | — | — | — | — | — | — | — | — |
| Total | 100.00 | 100.00 | 100.00 | 100.00 | 100.00 | 100.00 | 100.00 | 100.00 | 100.00 | 100.00 | 100.00 | 100.00 |

In accordance with Table 5, the following concentrations of excipients are provided in example formulations herein (for instance, within about +/−10-20% of values in Table 5): about 40-50% Transcutol (example solvent and/or penetration enhancer, alcohol), about 8-30% propylene glycol (example solvent and/or penetration enhancer, alcohol), about 12-24% glycerol (example solvent and/or penetration enhancer, alcohol, gelling agent), about 2-30% PEG (example solvent and/or penetration enhancer, alcohol, gelling agent), about 0.5-4% HPC (example gelling agent), about 0.5-2% Carbopol (example gelling agent), about 0.05-0.3% BHT (example antioxidant), and about 0.05-0.2% BHA (example antioxidant); wherein each of the excipients may be optional. In some cases, the composition comprises an organic solvent and/or penetration enhancer, and optionally the organic solvent and/or penetration enhancer is an alcohol and/or gelling agent; wherein optionally the total amount of organic solvent and/or penetration enhancer in the composition is about 80-100%, or about 86-99% of the composition. In some cases, the composition comprises an alcohol, and optionally the alcohol is an organic solvent/penetration enhancer and/or gelling agent; wherein optionally the total amount of alcohol in the composition is about 80-100%, or about 86%-99% of the composition. In some cases, the composition comprises an antioxidant; wherein optionally the total amount of the antioxidant is about 0.1-0.5%, or about 0.1-0.2% of the composition. In some cases, the composition comprises a gelling agent; wherein optionally the total amount of the gelling agent is about 16-64% of the composition, or about 21-42% of the composition. Accordingly, disclosed herein are compositions comprising the above example amounts of solvent and/or penetration enhancer, alcohol, gelling agent, and antioxidant, alone and in combination.

In accordance with Table 6, the following concentrations of excipients are provided in example formulations herein (for instance, within about +/−10-20% of values in Table 6): about 40-50% Transcutol (example solvent and/or penetration enhancer, alcohol), about 8-22% propylene glycol (example solvent and/or penetration enhancer, alcohol), about 3-12% ethanol (example solvent and/or penetration enhancer, alcohol), about 12-24% glycerol (example solvent and/or penetration enhancer, alcohol, gelling agent), about 2-45% PEG (example solvent and/or penetration enhancer, alcohol, gelling agent), about 0.5-4% HPC (example gelling agent), about 0.5-2% Carbopol (example gelling agent), about 0.1-0.3% ascorbic acid (example antioxidant), about 0.05-0.3% BHT (example antioxidant), and about 0.05-0.2% BHA (example antioxidant); wherein each of the excipients may be optional. In some cases, the composition comprises an organic solvent and/or penetration enhancer, and optionally the organic solvent and/or penetration enhancer is an alcohol and/or gelling agent; wherein optionally the total amount of organic solvent and/or penetration enhancer in the composition is about 65-100%, or about 86-98% of the composition. In some cases, the composition comprises an alcohol, and optionally the alcohol is an organic solvent/penetration enhancer and/or gelling agent; wherein optionally the total amount of alcohol in the composition is about 65-100%, or about 86-98% of the composition. In some cases, the composition comprises an antioxidant; wherein optionally the total amount of the antioxidant is about 0.2-0.8%, or about 0.1-0.2% of the composition. In some cases, the composition comprises a gelling agent; wherein optionally the total amount of the gelling agent is about 16-76% of the composition, or about 22-56% of the composition. Accordingly, disclosed herein are compositions comprising the above example amounts of solvent and/or penetration enhancer, alcohol, gelling agent, and antioxidant, alone and in combination.

In accordance with Tables 1, 2, 5, and 6, the following concentrations of excipients are provided in example formulations herein (for instance, within about +/−10-20% of values in Tables 1, 2, 5, and 6): about 40-50%, about 43-49%, about 47-49%, or about 47-48% Transcutol (example solvent and/or penetration enhancer, alcohol), about 8-30%, about 9-22%, about 18-22%, about 19-21% or about 19-20% propylene glycol (example solvent and/or penetration enhancer, alcohol), about 3-12%, about 4-6%, or about 9-11% ethanol (example solvent and/or penetration enhancer, alcohol), about 12-24%, about 14-20%, about 13-17%, about 14-16%, or about 14-15% glycerol (example solvent and/or penetration enhancer, alcohol, gelling agent), about 2-45%, about 3-24%, about 3-14%, about 13-15%, or about 13-14% PEG (example solvent and/or penetration enhancer, alcohol, gelling agent), about 0.5%-4%, or about 1-3% HPC (example gelling agent), about 2-4% or about 3% Sepineo (example gelling agent), about 0.5-2% or about 1% Carbopol (example gelling agent), and about 0.1-0.3% or about 0.2% ascorbic acid (example antioxidant), about 0.05-0.3% or about 0.1-0.2% BHT (example antioxidant), about 0.05-0.2% or about 0.1% BHA (example antioxidant), about 0.025-0.1% or about 0.05% propyl gallate (example antioxidant), about 0.001-0.003% or about 0.002% alpha-tocopheryl acetate (example antioxidant), about 0.01-0.03% or about 0.02% ascorbyl palmitate (example antioxidant); wherein each of the excipients may be optional. In some cases, the composition comprises an organic solvent and/or penetration enhancer, and optionally the organic solvent and/or penetration enhancer is an alcohol and/or gelling agent; wherein optionally the total amount of organic solvent and/or penetration enhancer in the composition is about 62-100%, or about 85-99% of the composition. In some cases, the composition comprises an alcohol, and optionally the alcohol is an organic solvent/penetration enhancer and/or gelling agent; wherein optionally the total amount of alcohol in the composition is about 62-100%, or about 85-99% of the composition. In some cases, the composition comprises an antioxidant; wherein optionally the total amount of the antioxidant is about 0.1-0.9%, or about 0.2-0.3% of the composition. In some cases, the composition comprises a gelling agent; wherein optionally the total amount of the gelling agent is about 16-76% of the composition, or about 18-56% of the composition. Accordingly, disclosed herein are compositions comprising the above example amounts of solvent and/or penetration enhancer, alcohol, gelling agent, and antioxidant, alone and in combination.

As a non-limiting example, the composition comprises about 40-50%, about 43-49%, about 47-49%, or about 47-48% Transcutol (example solvent and/or penetration enhancer, alcohol), about 2-45%, about 3-24%, about 3-14%, about 13-15%, or about 13-14% PEG (example solvent and/or penetration enhancer, alcohol, gelling agent), about 12-24%, about 14-20%, about 13-17%, about 14-16%, or about 14-15% glycerol (example solvent and/or penetration enhancer, alcohol, gelling agent), about 8-30%, about 9-22%, about 18-22%, about 19-21% or about 19-20% propylene glycol (example solvent and/or penetration enhancer, alcohol), about 0.05-0.3% or about 0.1-0.2% BHT (example antioxidant), about 0.05-0.2% or about 0.1% BHA (example antioxidant), about 0.5%-4%, or about 1-3% HPC (example gelling agent), or a combination of two or more thereof. As another non-limiting example, the composition comprises about 47-49% or about 47-48% Transcutol (example solvent and/or penetration enhancer, alcohol), about 13-15% or about 13-14% PEG (example solvent and/or penetration enhancer, alcohol, gelling agent), about 14-16% or about 14-15% glycerol (example solvent and/or penetration enhancer, alcohol, gelling agent), about 19-21% or about 19-20% propylene glycol (example solvent and/or penetration enhancer, alcohol), about 0.05-0.3% or about 0.1-0.2% BHT (example antioxidant), about 0.05-0.2% or about 0.1% BHA (example antioxidant), about 0.5%-4%, or about 1-3% HPC (example gelling agent), or a combination of two or more thereof. As another non-limiting example, the composition comprises about 47-48% Transcutol (example solvent and/or penetration enhancer, alcohol), about 13-14% PEG (example solvent and/or penetration enhancer, alcohol, gelling agent), about 14-15% glycerol (example solvent and/or penetration enhancer, alcohol, gelling agent), about 19-20% propylene glycol (example solvent and/or penetration enhancer, alcohol), about 0.1-0.2% BHT (example antioxidant), about 0.1% BHA (example antioxidant), about 3% HPC (example gelling agent), or a combination of two or more thereof.

In any of the examples or embodiments herein, ruboxistaurin, ruboxistaurin mesylate, or a salt thereof, is present in the composition at about 0.1%, about 0.8%, or about 1%.

Example 5: Short-Term Stability of Compositions of Example 4

The compositions of Table 5 and Table 6 were subjected to short-term physicochemical stability study following storage up to 5 months at 25° C. and 40° C. Parameters evaluated were content and purity of the compound (i.e., ruboxistaurin), apparent pH, macroscopic and microscopic observations.

Content and Purity of Compound

The content and purity of ruboxistaurin mesylate monohydrate in research and development compositions following storage up to 5 months are detailed in Table 7 and Table 8, respectively.

Percentage recovery (%) compares the response of drug peak to a standard of known concentration whereas percentage peak purity (% area) compares the area of the drug peak to the sum of the areas of all peaks in the chromatogram.

TABLE 7

Ruboxistaurin mesylate monohydrate content (% w/w from label claim) at t = 0 and following up to 4 weeks of stability testing at 25 and 40° C., average of n = 3 replicates (range in brackets).

Ruboxistaurin MM content (% w/w from label claim) at t = 0 and following up to 5 months of stability testing at 25 and 40° C.

| | | t = 2 weeks | | t = 4 weeks | | t = 12 weeks | | t = 5 months | |
|---|---|---|---|---|---|---|---|---|---|
| Formulation | t = 0 | 25° C. | 40° C. | 25° C. | 40° C. | 25° C. | 40° C. | 25° C. | 40° C. |
| NA01 ACT (modified control) | 98.11 (97.94-98.31) | | | | | | | | |
| NA13 ACT | 100.18 (99.59-100.55) | 99.93 (99.69-100.25) | 99.55 (99.47-99.62) | 99.01 (98.07-99.03) | 98.69 (98.65-98.73) | 96.40 (95.75-96.85) | 95.19 (95.02-95.29) | 100.23 (99.83-100.64) | 100.67 (99.83-101.27) |
| NA16 ACT | 99.49 (99.17-99.80) | 99.20 (98.71-99.45) | 99.56 (99.38-99.81) | 99.95 (99.43-100.31) | 97.75 (96.68-98.60) | | | | |
| NA17 ACT | 99.43 (99.25-99.54 | 99.42 (98.73-100.02) | 99.24 (99.07-99.43) | 99.46 (99 15-99.77) | 95.43 (93.43-97.35) | | | | |
| NA18 ACT | 100.10 (99.78-100.48) | 100.08 (99.66-100.41) | 100.07 (99.83-100.20) | 99 94 (99.66-100.29) | 97.18 (95.29-99.08)* | 96.59 (95.98-97.00) | 96.80 (96.60-97.17) | 99.90 (99.13-100.67)* | 99.56 (97.00-101.04) |
| NA19 AGT | 100.56 (100.42-100.66) | 100.67 (100.52-100.75) | 100.62 (100.26-100.98) | 101.23 (100.82-101.45) | 99.80 (99.70-99.97) | 98.36 (97.55-99.92) | 96.61 (95.70-97.91) | 100.29 (100 05-100.75) | 99.23 (98.44-100.01)* |

TABLE 7-continued

Ruboxistaurin mesylate monohydrate content (% w/w from label claim) at t = 0 and following up to 4 weeks of stability testing at 25 and 40° C., average of n = 3 replicates (range in brackets).

Ruboxistaurin MM content (% w/w from label claim) at t = 0 and following up to 5 months of stability testing at 25 and 40° C.

| Formulation | t = 0 | t = 2 weeks | | t = 4 weeks | | t = 12 weeks | | t = 5 months | |
|---|---|---|---|---|---|---|---|---|---|
| | | 25° C. | 40° C. | 25° C. | 40° C. | 25° C. | 40° C. | 25° C. | 40° C. |
| NA20 ACT | 101.18 (100.75-101.63) | 100.90 (100.78-101.01) | 100.82 (100.60-101.09) | 101.23 (100.84-101.73) | 98.73 (94.93-101.50) | | | | |
| NA21 ACT | 100.49 (99.80-100.92) | 99.00 (95.51-101.00) | 100.69 (100.53-100.81) | 100.74 (100.58-100.97) | 90.30 (97.38-99.12) | | | | |
| NA22 ACT | 98.78 (98.62-99.06) | 100.35 (98.28-104.42) | 98.36 (97.97-98.57) | 98.96 (98.35-99.58) | 97.17 (96.75-97.59) | 93.80 (92.34-94.98) | 93.89 (93.55-94.44) | 97.46 (96.78-98.01) | 94.15 (93.14-95.35) |
| NA25 ACT | 101.41 (101.09-101.67) | 100.91 (100.80-101.12) | 101.29 (100.90-101.68) | 101.96 (101.61-102.25) | 100.50 (99.05-101.44) | | | | |
| NA26 ACT | 98.86 (99.61-100.14) | 99.87 (99.68-100.18) | 99.70 (99.45-99.94) | 105.46 (105.10-105.66) | 98.46 (97.64-99.27)* | | | | |
| NA28 ACT | 100.41 (100.01-100.69) | 100.45 (100.25-100.76) | 99.87 (99.28-100.30) | 99.46 (98.92-100.00) | 99.57 (99.40-99.89) | 91.89 (90.02-92.95) | 94.29 (93.55-95.41) | 98.48 (97.54-100.28) | 97.56 (95.53-99.84) |

TABLE 8

Ruboxistaurin purity (% a/a) at t = 0 and following up to 4 weeks of stability testing at 25 and 40° C., average of n = 3 replicates (range in brackets).

Ruboxistaurin MM purity (% area) at t = 0 and following up to 4 weeks of stability testing at 25 and 40° C.

| Formulation | | Replica | t = 0 | t = 2 weeks | | t = 4 weeks | |
|---|---|---|---|---|---|---|---|
| | | | | 25° C. | 40° C. | 25° C. | 40° C. |
| NA01 ACT | Replicates | | 97.81 | | | | |
| | | | 97.53 | | | | |
| | | | 97.53 | | | | |
| | Average | | 97.62 | | | | |
| NA01 ACT (longer method to elute BHT) | | | 94.52 | | | | |
| NA13 ACT | Replicates | | 99.01 | Replicates 98.95 | Replicates 99.00 | Replicates 96.63 | Replicates 96.58 |
| | | | 99.02 | 98.84 | 99.04 | 96.62 | 96.46 |
| | | | 99.04 | 98.80 | 99.04 | 96.46 | 96.31 |
| | Average | | 99.01 | Average 98.96 | Average 98.73 | Average 96.57 | Average 96.45 |
| NA16 ACT (longer method to elute BHT) | | | 99.05* | Replicates 99.10 | Replicates 99.11 | Replicates 98.98 | Replicates 98.97 |
| | | | | 99.07 | 99.14 | 98.89 | 98.98 |
| | | | | 99.11 | 99.15 | 98.91 | 99.00 |
| | | | | Average 99.09 | Average 99.13 | Average 98.93 | Average 98.98 |
| NA17 ACT | Replicates | | 99.20 | Replicates | Replicates 99.11 | Replicates 98.97 | Replicates 98.96 |
| | | | 99.20 | 99.06 | 99.12 | 98.93 | 99.00 |
| | | | 99.18 | 99.00 | 99.11 | 98.94 | 99.01 |
| | Average | | 99.19 | Average 99.03 | Average 99.11 | Average 98.95 | Average 98.99 |
| NA17 ACT (longer method to elute BHT) | | | 99.02 | | | | |
| NA18 ACT | Replicates | | 99.09 | Replicates 98.99 | Replicates 99.08 | Replicates 98.92 | Replicates 98.86 |
| | | | 99.08 | 98.97 | 99.07 | 98.91 | 98.99 |
| | | | 99.09 | 98.98 | 99.07 | 98.91 | 98.99 |
| | Average | | 99.08 | Average 99.98 | Average 99.07 | Average 98.91 | Average 98.95 |
| NA18 ACT (longer method to elute BHT) | | | 98.97 | | | | |
| NA19 ACT | Replicates | | 99.12 | Replicates 98.95 | Replicates 99.22 | Replicates 98.11 | Replicales 99.15 |
| | | | 99.15 | 98.98 | 99.20 | 99.06 | 99.15 |
| | | | 99.14 | 99.00 | 99.18 | 99.06 | 99.15 |
| | Average | | 99.14 | Average 98.98 | Average 99.20 | Average 99.08 | Average 99.15 |
| NA19 ACT (longer method to elute BHT) | | | 98.99 | | | | |
| NA20 ACT | Replicates | | 99.18 | Replicates 99.05 | Replicates 99.19 | Replicates 95.05 | Replicates 99.09 |
| | | | 99.11 | 99.04 | 99.23 | 98.98 | 99.14 |
| | | | 99.17 | 99.00 | 99.22 | 99.01 | 99.10 |

TABLE 8-continued

Ruboxistaurin purity (% a/a) at t = 0 and following up to 4 weeks of stability testing at 25 and 40° C., average of n = 3 replicates (range in brackets).

Ruboxistaurin MM purity (% area) at t = 0 and following up to 4 weeks of stability testing at 25 and 40° C.

| Formulation | Replica | t = 0 | t = 2 weeks 25° C. | t = 2 weeks 40° C. | t = 4 weeks 25° C. | t = 4 weeks 40° C. |
|---|---|---|---|---|---|---|
| NA20 ACT (longer method to elute BHT) | Average | 99.15 99.08 | Average | 99.04 | Average | 99.21 | Average | 99.02 | Average | 99.11 |
| NA21 ACT | Replicates | 99.10 99.09 99.08 | Replicates | 99.01 98.97 97.59 | Replicates | 99.08 99.07 99.04 | Replicates | 98.89 98.83 98.92 | Replicates | 99.00 99.03 99.00 |
| NA21 ACT (longer method to elute BHT) | Average | 99.09 98.94 | Average | 98.52 | Average | 99.06 | Average | 98.88 | Average | 99.01 |
| NA22 ACT | Replicates | 98.75 98.72 98.69 | Replicates | 99.19 98.92 98.94 | Replicates | 98.95 98.92 98.94 | Replicates | 98.83 98.81 98.85 | Replicates | 98.38 98.37 98.36 |
| NA22 ACT (longer method to elute BHT) | Average | 98.72 98.55 | Average | 99.02 | Average | 98.94 | Average | 98.83 | Average | 98.37 |

It should be noted that, at t=0 data generated from both the initial implemented HPLC method and an HPLC method with the same gradient but extended in order to elute BHT is presented (for impurity data only). All other timepoints employed the HPLC analytical method with the longer run time.

At t=0 all drug recovery values were 98-102% of the label. Drug purity values were ca. >99% for all formulations. After 4 weeks of storage, the data suggests that drug recovery was consistent with t=0 at 25 and 40° C. (i.e., 100% of the label claim ±5%). Following 4 weeks of storage at 25 and 40° C., drug purity was slightly lower (ca. 0.1%-0.2% area) than was observed at t=0 and 2 weeks for the majority of formulations. Whilst this represents a minor downward trend, it is a huge improvement on the original formulations in which the ruboxistaurin mesylate monohydrate purity following storage for 4 weeks at 40° C. for non-aqueous gels was observed to be between 90.57 and 95.08%. It should be noted that the formulations which included 0.1% w/w ruboxistaurin mesylate monohydrate (i.e., NA22 and NA28) exhibited the lowest purity, and this may be due to the excipient: drug ratio in these formulations being higher than the formulations loaded with 0.8% w/w drug.

The recovery of ruboxistaurin mesylate monohydrate was within 100±5% for NA13, NA19, NA19, NA22 and NA28 following 5 months of storage, with the exception of NA22 ACT stored at 40° C. which had a recovery of 94.15% of the label claim (which was consistent with the lower purity of the drug observed from this formulation).

The average peak purity of ruboxistaurin mesylate monohydrate after 5 months ranged from 96.03% area (NA22, 40° C.) to 98.90% (NA19, 25° C.) and did not decrease by more than 1.6% peak area for any formulations following storage at either 25 or 40° C. It should be noted that the decrease of 1.6% was observed for the formulation NA22 which had a low drug loading (0.1%) and, as previously discussed, may be attributable to the higher excipient: drug ratio present in this formulation. For formulations with drug loading of ca. 0.8% (e.g. NA13, NA18 and NA19), a decrease of 1.5% peak purity was observed (NA13, stored at 40° C.) however both NA18 and NA19 exhibited a decrease in purity of <0.5%, with maximum decreases of 0.45% and 0.27% observed for NA18 and NA19, respectively, at both storage conditions. Notably, after 5 months, no individual impurity had a % a/a of greater than 0.8% following storage at 25 or 40° C. The peak purity of NA13 stored at 40° C. was higher than that observed at 25° C., and peaks at RT 4.2 and 5.2 appear to be smaller in size in the 40° C. than in the 25° C. sample. As such peaks were present in the 12 week 25 and 40° C. samples, the data generated for the 5 month time point suggests that the degradant products (i.e. peaks at RT 4.2 and RT 5.2) may be further degrading and are not observed using the current methodology.

The purity data, along with the drug recovery data, suggests that NA18 and NA19 are the most chemically stable formulations over a period of 5 months, and may as a result present as lead candidates for further development.

Apparent pH

The apparent pH of compositions with or without ruboxistaurin mesylate monohydrate up to t=5 months (2-8° C., 25° C., and 40° C.) is presented in Table 9.

TABLE 9

Apparent pH of Compositions under Stability Study

Apparent pH

| Formulation | t = 0 | t = 2 weeks 25° C. | t = 2 weeks 40° C. | t = 4 weeks 25° C. | t = 4 weeks 40° C. | t = 12 weeks 25° C. | t = 12 weeks 40° C. | t = 5 months 25° C. | t = 5 months 40° C. |
|---|---|---|---|---|---|---|---|---|---|
| NA01 ACT | 4.02 | | | | | | | | |
| NA01 PLB | 4.69 | | | | | | | | |

TABLE 9-continued

Apparent pH of Compositions under Stability Study

| | | Apparent pH | | | | | | | |
|---|---|---|---|---|---|---|---|---|---|
| | | t = 2 weeks | | t = 4 weeks | | t = 12 weeks | | t = 5 months | |
| Formulation | t = 0 | 25° C. | 40° C. | 25° C. | 40° C. | 25° C. | 40° C. | 25° C. | 40° C. |
| NA13 ACT | 5.71 | 5.75 | 5.80 | 5.17 | 5.27 | 4.88 | 5.02 | 4.79 | 4.95 |
| NA13 PLB | 5.26 | 5.29 | 4.92 | | | | 5.32 | 5.25 | N/A |
| NA16 ACT | 4.56 | 5.29 | 4.20 | 4.39 | 4.35 | | | | |
| NA16 PLB | 7.04 | 6.20 | 7.45 | 7.58 | 7.74 | | | | |
| NA17 ACT | 4.21 | 4.21 | 4.24 | 4.32 | 4.23 | | | | |
| NA17 PLB | 6.63 | 6.88 | 7.19 | 7.24 | 7.39 | | | | |
| NA18 ACT | 4.34 | 4.33 | 4.37 | 4.15 | 4.22 | 4.11 | 4.01 | 388 | 4.03 |
| NA18 PLB | 6.08 | 6.34 | 7.15 | 7.21 | 7.36 | 7.15 | 6.83 | 7.04 | 7.01 |
| NA19 ACT | 3.82 | 3.79 | 3.87 | 3.70 | 3.70 | 3.73 | 3.65 | 3.39 | 3.70 |
| NA19 PLB | 4.21 | 4.46 | 5.61 | 5.31 | 5.30 | 5.16 | 5.05 | 5.14 | 5.26 |
| NA20 ACT | 3.93 | 3.93 | 3.82 | 3.96 | 3.98 | | | | |
| NA20 PLB | 6.96 | 6.38 | 6.90 | 7.04 | 7.15 | | | | |
| NA21 ACT | 4.16 | 4.25 | 4.43 | 4.09 | 4.09 | | | | |
| NA21 PLB | 6.98 | 6.94 | 7.09 | 7.17 | 7.33 | | | | |
| NA22 ACT | 4.97 | 4.77 | 5.05 | 4.84 | 5.01 | 4.95 | 4.66 | 4.66 | 4.84 |
| NA22 PLB | 7.21 | 6.98 | 7.11 | 7.19 | 7.33 | 7.02 | 7.11 | 6.77 | 6.99 |
| NA25 ACT | 3.99 | 4.01 | 4.06 | 3.83 | 3.87 | | | | |
| NA25 PLB | 6.13 | 6.55 | 6.91 | 6.08 | 6.96 | | | | |
| NA26 ACT | 4.05 | 4.21 | 4.25 | 4.08 | 4.09 | | | | |
| NA26 PLB | 7.10 | 6.73 | 7.12 | 7.10 | 7.15 | | | | |
| NA28 ACT | 4.89 | | | 5.51 | 5.69 | 5.15. | 4.92 | 5.03 | 5.24 |

At t=0 the pH varied between 5.25-7.21 for placebo formulations and between 4.55-4.97 for active formulations. Notably the pH of 0.25% ruboxistaurin mesylate monohydrate formulations was lower than the equivalent 0.1% formulation. The pH of NA18 and NA19 containing 0.8% drug had pH values of 4.34 and 3.82, respectively at t=0 in the previous stability test, which further demonstrates the trend of higher drug level leading to a lower pH. After 12 weeks of storage, the apparent pH remained consistent (i.e. within 0.5 units) of the value reported at t=0 for all formulations.

Macroscopic Observations

At t=0, all of the active formulations appeared red due to the presence of ruboxistaurin mesylate monohydrate with all placebo appearing colourless. Notably, formulations in which there is a lower concentration of ruboxistaurin mesylate monohydrate, were clear and lighter in colour due to the lower concentration of ruboxistaurin mesylate monohydrate present. NA19 PLB was translucent and may be due to the nature of the gelling agent. This hypothesis is further evidenced by formulation NA19 being of low viscosity, suggesting that the gelling agent has not fully hydrated.

There was no notable change in macroscopic appearance after 4 weeks of storage. An additional timepoint at t=12 weeks and 5 months was performed in which the macroscopic appearance of NA13, NA18, NA19, NA22 and NA28 was assessed, after which time there was no notable change in the appearance.

Microscopic Observations

The microscopic appearance and microscopic images (non-polarised and polarised light) were accessed for all compositions including ruboxistaurin mesylate monohydrate and corresponding vehicles.

At t=0 the majority of formulation did not have excipient or drug crystals present. Notably, API was observed in active formulation NA25.

After 2 weeks of storage, formulations did not contain API crystals (excepting NA25 at 25 and 40° C., and NA16 at 40° C. only). After 4 weeks of storage no change was observed in NA13, NA18, NA19, NA20, NA22 and NA28, although crystals suspected to be API were evident in the following formulations:

NA16 (25 and 40° C.)

NA17 (25° C.)

NA21 (40° C.)

NA26 (25 and 40° C.)

To confirm the above observations, the NA16, NA17 and NA26 formulations were also analyzed for microscopic appearance at the 2-8° C. storage condition and crystals were observed.

While these crystals are suspected to be API, as they are not present in placebo formulations, based on the composition of the active formulations it is not apparent what is driving the crystallization observed. For example, NA17 and NA18 share identical formulation composition, with the exception of 0.1% w/w BHA in NA18, and API crystals are only observed in the former.

An additional timepoint at t=12 weeks and months 5 was performed in which the microscopic appearance of NA13, NA18, NA19, NA22 and NA28 was assessed following storage at 25 and 40° C. NA18, NA10, NA22 and NA28 did not appear to contain drug crystals after 5 months at 2-8, 25 or 40° C.

Based on the composition of formula NA18, 12 kg GMP batches of 0.8% w/w ruboxistaurin mesylate monohydrate gel (Lot #910006) and placebo gel (Lot #910008) were manufactured in bulk and filled into Montebello tubes at 12 g per tube, tested and released and placed on stability at 25° C./60% R/H and 40° C./75% R/H. The tables below present the 6-month data for the 0.8% w/w gel lot #910006.

TABLE 10

0.8% w/w Ruboxistaurin Mesylate Monohydrate Clinical Trial Lots Stability Results

| Lot #: 910006 | | | Results | | | |
|---|---|---|---|---|---|---|
| 0.8% w/w | | | 3 months | | 4 months | |
| Test | Specification | Release | 25° C./60% RH | 40° C./75% RH | 25° C./60% RH | 40° C./75% RH |
| Identity | HPLC Rt Corresponds to RS HPLC Rt | HPLC Rt Corresponds to RS HPLC Rt | HPLC Rt Corresponds to RS HPLC Rt | HPLC Rt Corresponds to RS HPLC Rt | HPLC Rt Corresponds to RS HPLC Rt | HPLC Rt Corresponds to RS HPLC Rt |
| Assay | 90-110% Label Claim | B: 93%, 94%, 93% M: 93%, 93%, 93% E: 93%, 93%, 93% Average: 93% | 95% | 95% | 95% | 96% |
| Related Substances | Report RRT/% Ind. Impur. ≥0.1% a/a | B: RRT 1.72; 0.23% a/a (n = 2) M: RRT 1.73; 0.24% a/a (n = 2) E: RRT 1.73; 0.23% a/a (n = 2) | RRT 1.72: 0.23% a/a | RRT 1.70: 0.25% a/a | RRT 1.73: 0.33% a/a | RRT 1.72: 0.30% a/a |
| | Total Impurities NMT 5.0% a/a | 0.23% a/a | 0.23% a/a | 0.23% a/a | 0.33% a/a | 0.30% a/a |
| Uniformity | USP <3> | Pass | Pass | Pass | Pass | Pass |
| Macroscopic Appearance | Orange to red to clear to translucent with smooth application and low viscosity | Red clear gel with a smooth application and medium viscosity | Red clear gel with a smooth application and medium viscosity | Red clear gel with a smooth application and medium viscosity | Red clear gel with a smooth application and medium viscosity | Red clear gel with a smooth application and medium viscosity |
| Microscopic Appearance | Absence of API particles | Absence of API particles | Absence of API particles | Absence of API particles | Absence of API particles | Absence of API particles |
| Apparent pH | Report Results | B: 4.96 M: 5.06 E: 5.04 | 4.40 | 4.55 | 5.26 | 4.87 |
| Apparent Viscosity | Report Results | Not Tested | 18590 cP | 19230 cP | 19870 cP | 15200 cP |
| USP<61> | TAMC: NMT 100 CFU/g | <10 CFU/g | NA | NA | NA | NA |
| | TYMC: NMT 10 CFU/g | <10 CFU/g | NA | NA | NA | NA |
| USP<62> | P. aeruginosa: Absent/1 g | Not Detected | NA | NA | NA | NA |
| | S. aureus: Absent/1 g | Not Detected | NA | NA | NA | NA |

| Lot #: 910006 | | Results | | | |
|---|---|---|---|---|---|
| 0.8% w/w | | 5 months | | 6 months | |
| Test | Specification | 25° C./60% RH | 40° C./75% RH | 25° C./60% RH | 40° C./75% RH |
| Identity | HPLC Rt Corresponds to RS HPLC Rt | HPLC Rt Corresponds to RS HPLC Rt | HPLC Rt Corresponds to RS HPLC Rt | HPLC Rt Corresponds to RS HPLC Rt | HPLC Rt Corresponds to RS HPLC Rt |
| Assay | 90-110% Label Claim | 95% | 95% | 96% | 95% |
| Related Substances | Report RRT/% Ind. Impur. ≥0.1% a/a | RRT 1.68: 0.32% a/a | RRT 1.66: 0.11% a/a; RRT 1.68: 0.29% a/a | RRT 1.71: 0.32% a/a | RRT 1.37: 0.10% a/a; RRT 1.68: 0.14% a/a; RRT 1.71: 0.30% a/a |
| | Total Impurities NMT 5.0% a/a | 0.32% a/a | 0.39% a/a | 0.32% a/a | 0.53% a/a |
| Uniformity | USP <3> | Pass | Pass | Pass | Pass |
| Macroscopic Appearance | Orange to red to clear to translucent with smooth application and low viscosity | Red clear gel with a smooth application and medium viscosity | Red clear gel with a smooth application and medium viscosity | Red clear gel with a smooth application and medium viscosity | Red clear gel with a smooth application and medium viscosity |
| Microscopic Appearance | Absence of API particles | Absence of API particles | Absence of API particles | Absence of API particles | Absence of API particles |
| Apparent pH | Report Results | 4.71 | 4.63 | 5.03 | 4.41 |
| Apparent Viscosity | Report Results | 19900 cP | 18500 cP | 19260 cP | 18530 cP |

TABLE 10-continued 0.8% w/w Ruboxistaurin Mesylate Monohydrate Clinical Trial Lots Stability Results

| | | | | | |
|---|---|---|---|---|---|
| USP<61> | TAMC: NMT 100 CFU/g | NA | NA | NA | <10 CFU/g |
| | TYMC: NMT 10 CFU/g | NA | NA | NA | <10 CFU/g |
| USP<62> | P. aeruginosa: Absent/1 g | NA | NA | NA | Not Detected |
| | S. aureus: Absent/1 g | NA | NA | NA | Not Detected |

After 6 months of storage in accordance with the International Conference on Harmonization (ICH) Guidance Q1A(R2) Stability Testing of New Drug Substances and Drug Products at ambient (25° C./60% Relative Humidity) and accelerated (40° C./75% Relative Humidity) temperature and conditions, the lots remained within specification from the time of lot release to the most recent timepoint. Moreover, per the ICH Q1A(R2) Guidance, the 6-month time point at the accelerated (40° C./75% Relative Humidity) conditions represent a significant success in the demonstration of stability for this drug product formulation as the guidance does not call for further testing under these conditions. Stability testing at the ambient (25° C./60% Relative Humidity) condition is ongoing.

Example 6: Clinical Trial

A randomized, observer-blinded, vehicle-controlled study on the safety and efficacy of twice daily application of 0.10% and 0.8% ruboxistaurin mesylate monohydrate gel with excipients of formula NA10, NA18, NA22, or NA28 (referred to as "ruboxistaurin Gel") vs. vehicle gel vs. hydroquinone cream on sun-exposed and sun-protected skin of adults is performed for 12 weeks.

The objectives of this study were to compare the effect of daily application of 0.10% and 0.8% ruboxistaurin Gel, 4% Hydroquinone cream, and Vehicle Gel. Efficacy assessments were summarized descriptively by treatment group and visits. The study was a two tranche randomized, observer-blinded and vehicle-controlled multi-dose, study in adult subjects with Fitzpatrick Skin Types IV-V and a colorimeter L* measurement between 57.8 and 46.1, as measured by the Chromometer CM-700. Subjects in the first tranche were randomized to one of 3 arms: (1) 0.8% ruboxistaurin Gel cohort (twice daily application for 12 weeks), (2) 4% Hydroquinone cream cohort (twice daily application for 12 weeks), or (3) Vehicle Gel cohort. In the second tranche, subjects were randomized to one of 2 arms: (1) 0.1% ruboxistaurin Gel or (2) Vehicle Gel cohort. One open-label sub-group includes subjects with dorsal hand solar lentigos, to receive twice daily applications of 0.8% ruboxistaurin Gel.

Approximately 90 subjects were enrolled, meeting the inclusion/exclusion criteria into the two randomized tranches. First tranche of approximately 45 subjects: 0.8% ruboxistaurin Gel, 4% Hydroquinone cream, or Vehicle Gel and Second tranche with approximately 30 subjects: 0.1% ruboxistaurin Gel or Vehicle Gel). Subjects in the two tranche cohorts received applications to unilateral upper volar arm and dorsal forearm, and approximately 15 subjects with dorsal hand solar lentigos were enrolled into a sub-cohort applying 0.8% ruboxistaurin gel to solar lentigos on unilateral dorsal hand and upper volar arm. Each subject in the two randomized tranches (First tranche: 0.8% ruboxistaurin Gel, 4% Hydroquinone cream, or Vehicle Gel and Second tranche: 0.10% ruboxistaurin Gel or Vehicle Gel) had two treatment sites and two contralateral untreated control sites. Subjects in the solar lentigo sub-cohort: the within-subject bilateral comparisons had two treatment sites using 0.8% ruboxistaurin Gel and two contralateral untreated control sites.

Primary outcome measurements included: decrease in pigmentation based on melanin index (change in L* and ITA colorimetry measurements, measured 12 weeks after first dose); and decrease in pigmentation based on digital imaging (change as measured with Canfield RBX software analysis, measured 12 weeks after first dose).

Secondary outcome measurements included: percent change in Investigator Dynamic Grading Assessment (IDGA), percent pigmentation differences between treated and contralateral Percent Change in Investigator Dynamic Grading Assessment (IDGA) (measured at 2, 4, 6, 8, 10, and 12 weeks from first dose); and proportion of subjects with Improved Investigator Dynamic Grading Scale (IDGA), proportion of subjects with less pigmentation at treated sites vs contralateral untreated sites (measured at 2, 4, 6, 8, 10, and 12 weeks from first dose).

Eligibility criteria included: Male or Female at least 18 years of age; must be Fitzpatrick Skin Type IV-V and have an L* measurement between 57.8 and 46.1, using the Chromometer CM-700; ability to understand, agree to, and sign the study informed consent form (ICF); agree to discontinue all agents used to treat hyperpigmentation, aging or exfoliate the skin during the course of the study (makeup and moisturizers are permitted); agree not to change their sun exposure at work, home, or leisure; technical ability and willingness to apply test articles; willing to allow digital photos of treatment and comparison areas to be taken and stored; Additional Inclusion Criterion for the solar lentigo Sub-Cohort: at least 4 solar lentigos at least 4 mm in diameter present on each dorsal hand.

Exclusion criteria included: Positive urine pregnancy test, pregnant, lactating, or female of childbearing potential who does not agree to use an active method of birth control for the duration of the study; conditions at baseline that would interfere with evaluation of UV-tanned skin, especially other pigmentary disorders including, but not limited to, melasma or vitiligo affecting the treatment and comparison sites; presence of known concomitant diseases associated with the development of hyperpigmentation (e.g., thyroid, liver, adrenal); current tanning booth exposure or any kind of phototherapy within 3 months of Screening; current or past use of monobenzyl ether or hydroquinone (Benoquin) to depigment the skin; Past or recent use of any skin bleaching treatment within 6 months of Screening; a chemical peel within 3 months of Screening; laser or light-based treatment of the treatment areas within 3 months of Screening; use of any photosensitizing medications within the past 6 months of Screening, including psoralens, sulfonamide drugs, tetracycline antibiotics, thiazide diuretics, phenothiazines, coal tar and derivatives, and tricyclic antidepressants; any dermatological conditions that could interfere with clinical evaluations or any disease state or physical condition which might expose the subject to an unacceptable risk by study participation; any underlying disease(s) or other dermatological conditions that require the use of exclusionary topical or systemic therapy (see Exclusion criteria 5 and 6); unwilling to discontinue applying any prescription or over the counter (OTC) topical product creams and ointments, other than makeup and moisturizers, on treatment area(s) at Baseline through their last day of study; treatment of any type of cancer within 6 months of Screening with the exception of superficial skin cancers such as basal cell or squamous cell carcinoma; known allergy to any of the test article(s) or any components in the test article(s) or history of hypersensitivity or allergic reactions to any of the study preparations as described in the Investigator's Brochure; history of active atopic dermatitis, as diagnosed by a physician, requiring treatment within the past 2 years; unable to meet the study attendance requirements; any history of psychiatric disease or history of alcohol or drug abuse that would interfere with the ability to comply with the study protocol; participation in any other trial of an investigational drug or device within 30 days prior to enrollment or participation in a research study concurrent with this study; Additional Exclusion Criterion for the Sub-Cohort: any previous treatment for solar lentigos on the dorsal hands.

This proposed proof of concept clinical trial tested the ability of topical ruboxistaurin Gel to prevent both UV-induced melanogenesis in facultative skin color and solar lentigos, and non-UV induced melanogenesis in constitutive skin color. Efficacy in this trial demonstrates proof of sufficient dermal penetration and mechanism of action which would enable future trials in melasma, lentigos, and other disorders related to increased melanin production.

Example 7: Clinical Trial Results

Materials and Methods

A Phase 2A, Observer-blinded, randomized study as described in Example 6 was conducted to evaluate the safety and efficacy of topically applied ruboxistaurin gel 0.8% with excipients of formula NA10, NA19, NA18, NA22, or NA28 (referred to as "ruboxistaurin gel") in healthy adult male and female subjects and a sub-cohort with the additional presence of dorsal hand solar lentigines.

The study comprised a 12-week twice daily dosing period. Sixty subjects who meet the eligibility criteria, notably Fitzpatrick Skin Types IV-V and corresponding Melanin Index parameters (colorimeter L* measurement between 57.8 and 46.1) were enrolled in the randomized tranche defined as (1) 60 subjects in a 1:1:1 ratio to one of three treatment arms: ruboxistaurin gel 0.8%, Hydroquinone cream 4%, or Vehicle Gel. Approximately 15 subjects meeting the above Fitzpatrick Skin Type and Melanin Index criteria were also assigned to a sub-cohort with dorsal hand lentigines to receive applications of 0.8% ruboxistaurin gel only.

Each subject applied daily approximately 0.2 g of the assigned study test article twice daily to exposed and sun protected skin. The randomized tranche required subjects to apply the test article twice daily to the upper volar (inner) arm and ipsilateral dorsal hand. The sub-cohort with dorsal hand solar lentigines applied the test article twice daily to the upper volar (inner arm) and ipsilateral dorsal hand that, at minimum, had 4 representative solar lentigines. The test article was applied to approximately 100 cm$^2$ in each treatment area, about the size of the palm of ones' hand. For the sub-cohort, 0.2 g of the assigned study test article was applied to the entire unilateral dorsal hand, to sufficiently cover all 4 solar lentigines, and separately, 0.2 g of the assigned study test article was applied to the unilateral upper volar (inner arm).

Skin pigmentation was assessed by a blinded (or unblinded for lentigines) Investigator using Investigator Dynamic Grading Assessment IDGA, Melanin Index, and Digital Imaging.

Safety and tolerability of the ruboxistaurin gel 0.8% was assessed at all visits and included monitoring of adverse events and local tolerability. Tolerability was evaluated through assessment of selected local signs and symptoms (pain/burning/stinging, pruritus, erythema, edema, erosion/ulceration, lichenification (dryness), exudation (scabbing crusting), desquamation (peeling) of skin to which the study test article is applied.

Results

Figure 2A:
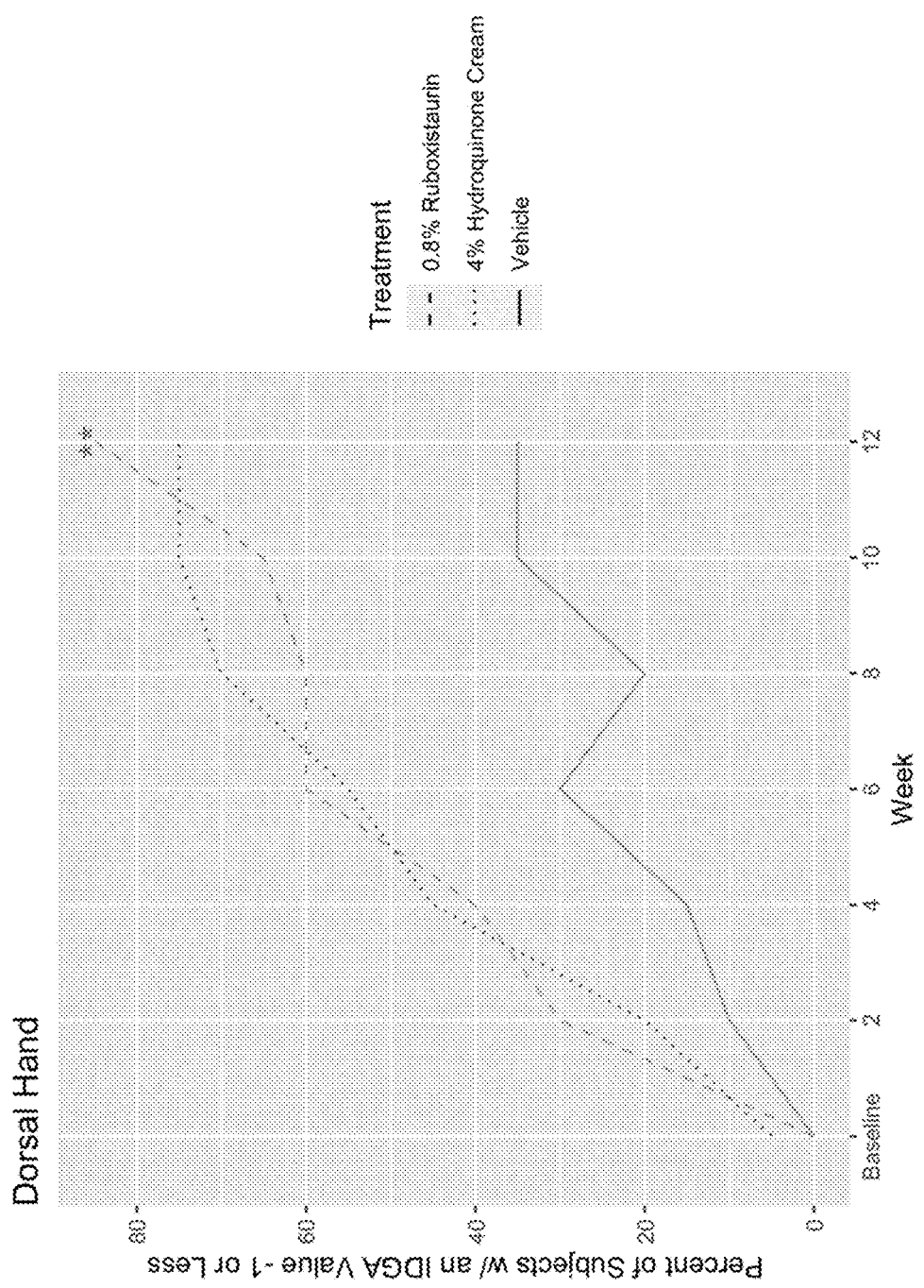
FIG. 2A Percent of Subjects with a −1 IDGA value (slightly lighter than untreated control) on the dorsal hand over 12 weeks of treatment with ruboxistaurin mesylate monohydrate gel 0.8% w/w, hydroquinone 4% w/w, or vehicle (** is $p<0.01$).
Figure 3A:
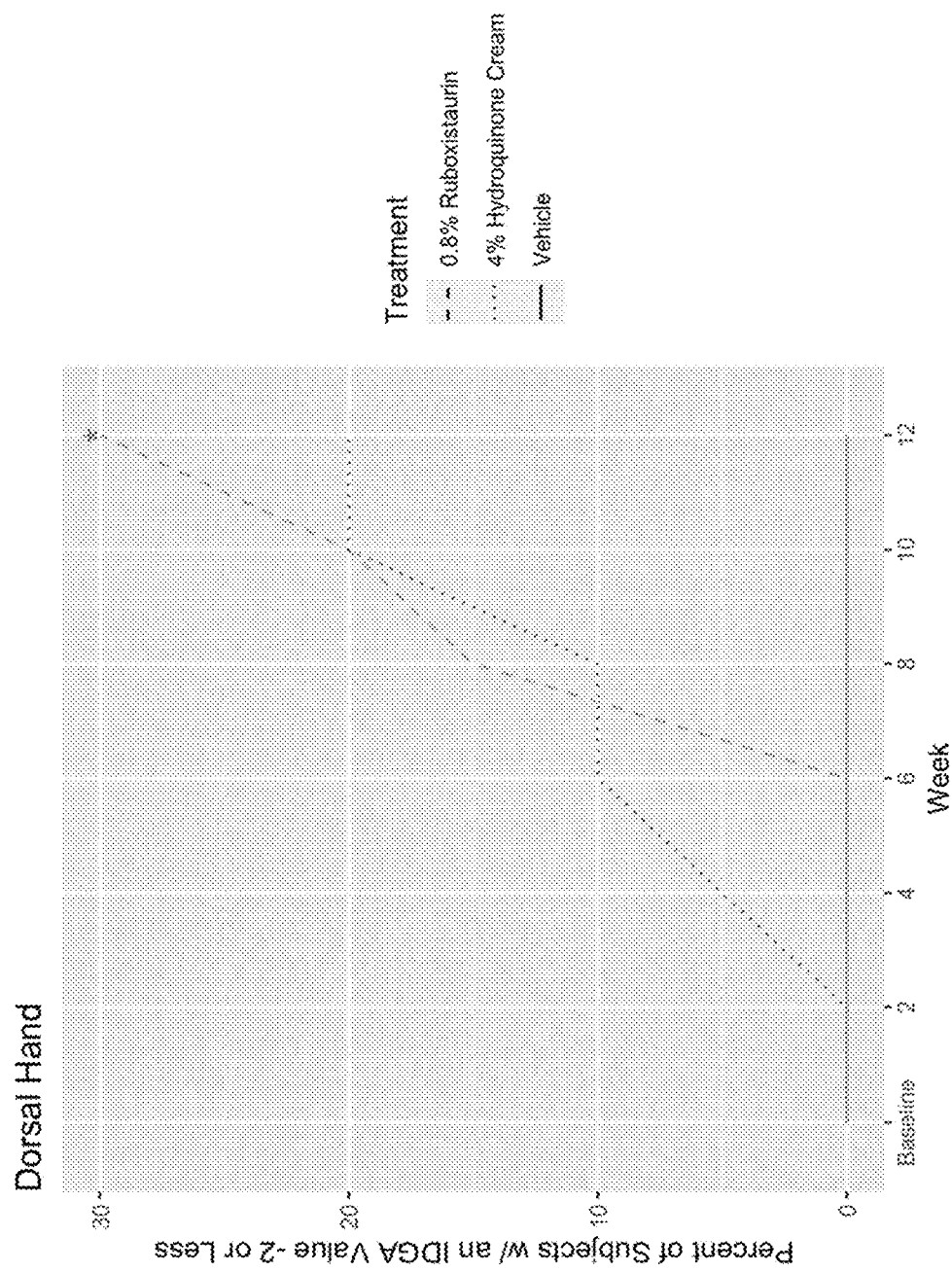
FIG. 3A Percent of Subjects with a −2 IDGA value (moderately lighter than untreated control) on the dorsal hand over 12 weeks of treatment with ruboxistaurin mesylate monohydrate gel 0.8% w/w, hydroquinone 4% w/w, or vehicle (* is $p<0.05$).

Dorsal Hand and Volar Arm Skin:

All treated sites were scored with the Investigator Dynamic Global Assessment (IDGA), which compares the relative pigmentation of a treated side to an untreated control side. For the dorsal hand, 85% of subjects treated with ruboxistaurin gel 0.8%, 75% treated with hydroquinone 4.0%, and 35% treated with vehicle gel achieved an IDGA of −1 or less (slightly less pigment than the untreated control side) ($p<0.01$ comparing ruboxistaurin gel 0.8% vs. vehicle) (Table 10; FIG. 2a). Thirty percent (30%) of subjects treated with ruboxistaurin gel 0.8%, 20% treated with hydroquinone 4%, and 0% treated with vehicle gel achieved an IDGA of −2 or less (moderately less pigment than the untreated control side) ($p<0.05$ comparing 0.8% ruboxistaurin gel vs. vehicle) (Table 11; FIG. 3a).

Figure 2B:
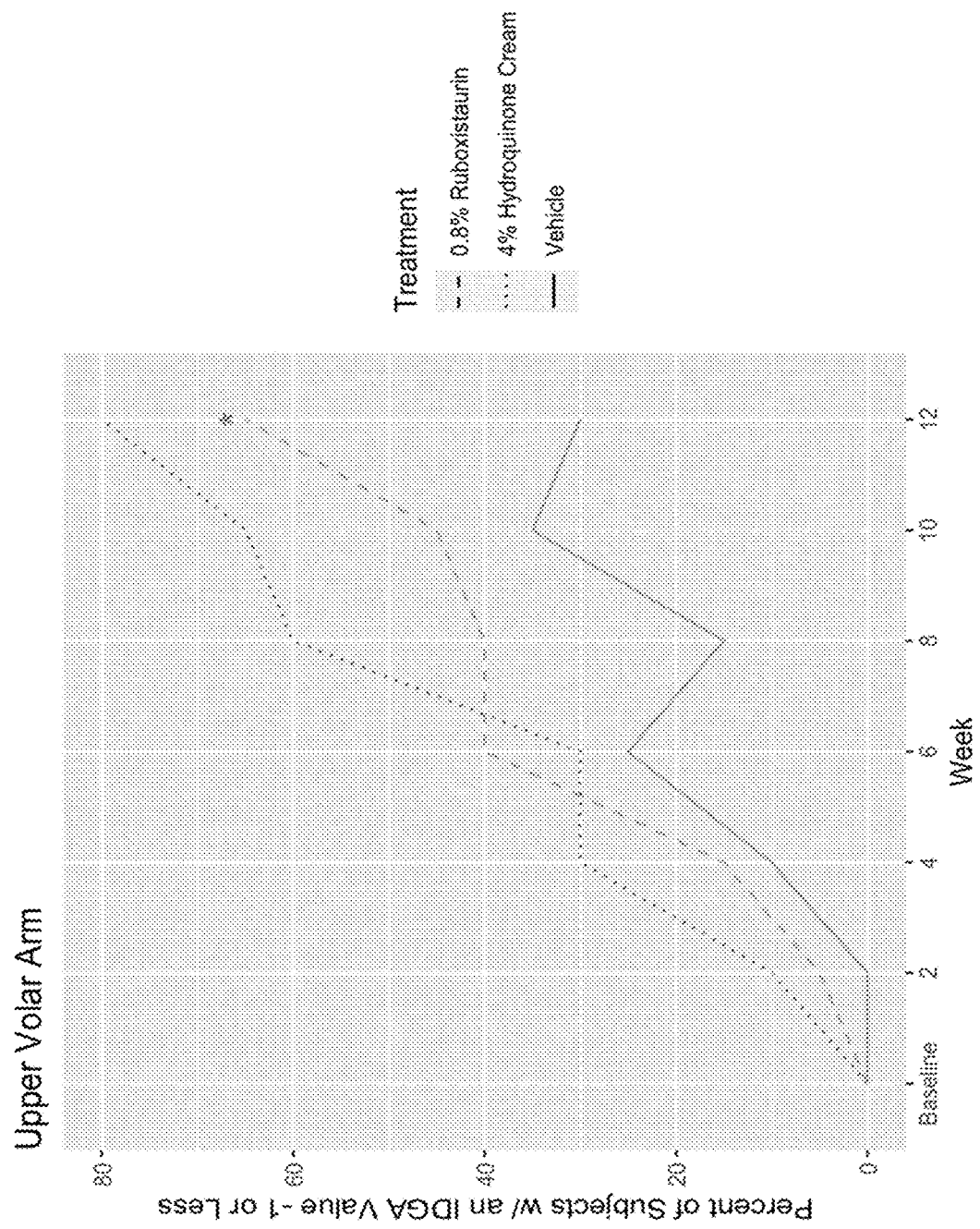
FIG. 2B Percent of Subjects with a −1 IDGA value (slightly lighter than untreated control) on the upper volar arm over 12 weeks of treatment with ruboxistaurin mesylate monohydrate gel 0.8% w/w, hydroquinone 4% w/w, or vehicle (* is $p<0.05$).
Figure 3B:
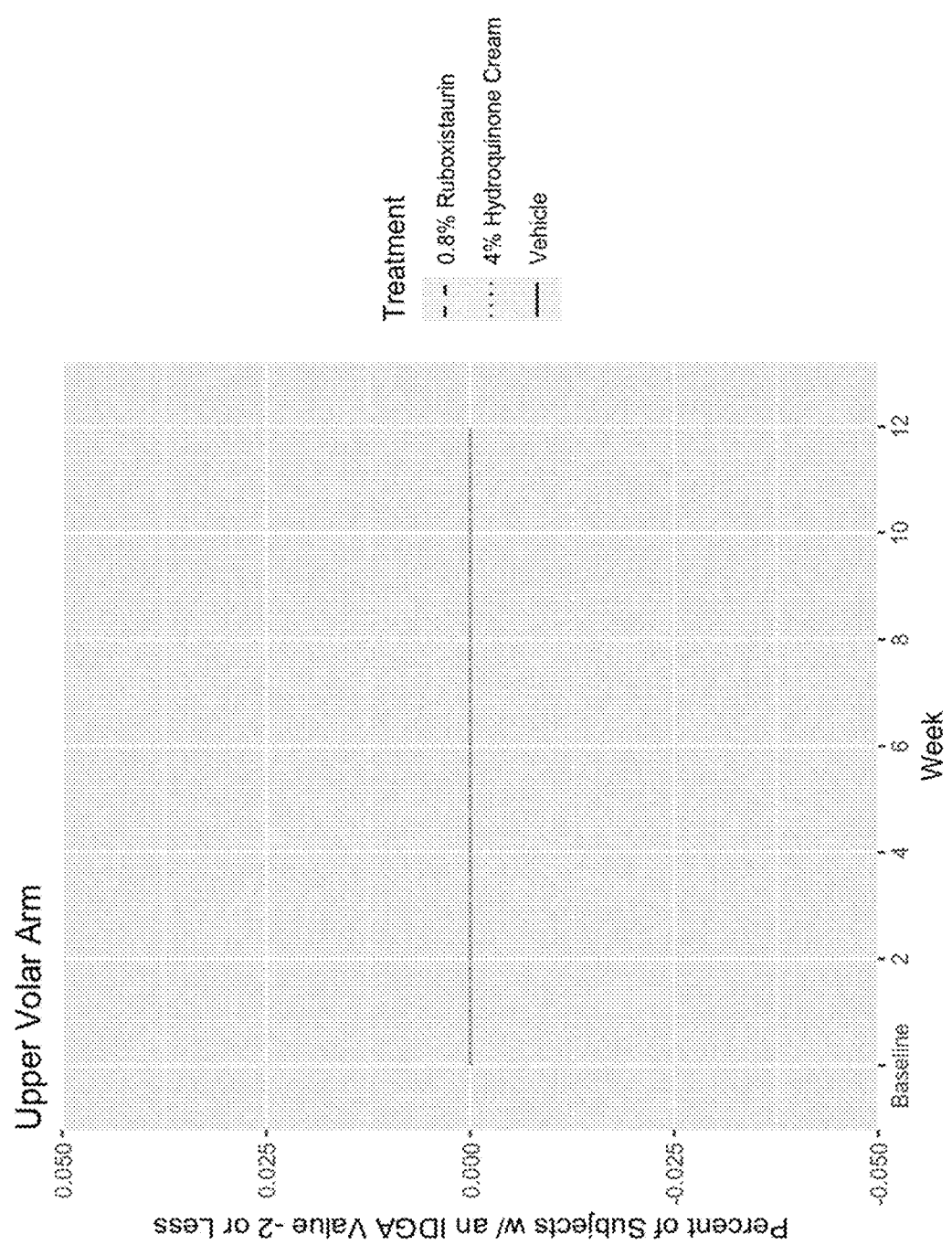
FIG. 3B Percent of Subjects with a −2 IDGA value (moderately lighter than untreated control) on the upper volar arm over 12 weeks of treatment with ruboxistaurin mesylate monohydrate gel 0.8% w/w, hydroquinone 4% w/w, or vehicle.

For the upper volar arm area, 65% of subjects treated with ruboxistaurin gel 0.8%, 85% treated with hydroquinone 4.0%, and 30% treated with vehicle gel achieved an IDGA of −1 or less (slightly less pigment than the untreated control side) ($p<0.05$ comparing ruboxistaurin gel 0.8% vs. vehicle) (Table 10: FIG. 2b). No subjects treated with ruboxistaurin gel 0.8%, hydroquinone 4%, or vehicle gel achieved an IDGA of −2 or less (moderately less pigment than the untreated control side) (Table 11; FIG. 3b).

TABLE 10

Percent of subjects treated on the dorsal hand or upper volar arm with an IDGA value of −1 or less.

| Week | Treatment | Percent |
| --- | --- | --- |
| Percent of Subjects w/an IDGA Value of −1 or Less for Dorsal Hand | | |
| Baseline | Hydroquinone Cream 4% | 5 |
| Baseline | Ruboxistaurin gel 0.8% | 0 |
| Baseline | Vehicle | 0 |
| 2 | Hydroquinone Cream 4% | 20 |
| 4 | Hydroquinone Cream 4% | 45 |
| 6 | Hydroquinone Cream 4% | 55 |
| 8 | Hydroquinone Cream 4% | 70 |
| 10 | Hydroquinone Cream 4% | 75 |
| 12 | Hydroquinone Cream 4% | 75 |
| 2 | Ruboxistaurin gel 0.8% | 30 |
| 4 | Ruboxistaurin gel 0.8% | 40 |
| 6 | Ruboxistaurin gel 0.8% | 60 |

TABLE 10-continued

Percent of subjects treated on the dorsal hand or upper volar arm with an IDGA value of −1 or less.

| Week | Treatment | Percent |
|---|---|---|
| 8 | Ruboxistaurin gol 0.8% | 60 |
| 10 | Ruboxistaurin gel 0.8% | 65 |
| 12 | Ruboxistaurin gel 0.8% | 85 |
| 2 | Vehicle | 10 |
| 4 | Vehicle | 15 |
| 6 | Vehicle | 30 |
| 8 | Vehicle | 20 |
| 10 | Vehicle | 35 |
| 12 | Vehicle | 35 |
| Percent of Subjects w/an IDGA Value of −1 or Less for Upper Volar Arm | | |
| Baseline | Hydroquinone Cream 4% | 0 |
| Baseline | Ruboxistaurin gel 0.8% | 0 |
| Baseline | Vehicle | 0 |
| 2 | Hydroquinone Cream 4% | 10 |
| 4 | Hydroquinone Cream 4% | 30 |
| 6 | Hydroquinone Cream 4% | 30 |
| 8 | Hydroquinone Cream 4% | 60 |
| 10 | Hydroquinone Cream 4% | 65 |
| 12 | Hydroquinone Cream 4% | 80 |
| 2 | Ruboxistaurin gel 0.8% | 5 |
| 4 | Ruboxistaurin gel 0.8% | 15 |
| 6 | Ruboxistaurin gel 0.8% | 40 |
| 8 | Ruboxistaurin gel 0.8% | 40 |
| 10 | Ruboxistaurin gel 0.8% | 45 |
| 12 | Ruboxistaurin gel 0.8% | 65 |
| 2 | Vehicle | 0 |
| 4 | Vehicle | 10 |
| 6 | Vehicle | 25 |
| 8 | Vehicle | 15 |
| 10 | Vehicle | 35 |
| 12 | Vehicle | 30 |

TABLE 11

Percent of subjects treated on the dorsal hand or upper volar arm with an IDGA value of −2 or less.

| Week | Treatment | Percent |
|---|---|---|
| Percent of Subjects w/an IDGA Value of −2 or Less for Dorsal Hand | | |
| Baseline | Hydroquinone Cream 4% | 0 |
| Baseline | Ruboxistaurin gel 0.8% | 0 |
| Baseline | Vehicle | 0 |
| 2 | Hydroquinone Cream 4% | 0 |
| 4 | Hydroquinone Cream 4% | 5 |
| 6 | Hydroquinone Cream 4% | 10 |
| 8 | Hydroquinone Cream 4% | 10 |
| 10 | Hydroquinone Cream 4% | 20 |
| 12 | Hydroquinone Cream 4% | 20 |
| 2 | Ruboxistaurin gel 0.8% | 0 |
| 4 | Ruboxistaurin gel 0.8% | 0 |
| 6 | Ruboxistaurin gel 0.8% | 0 |
| 8 | Ruboxistaurin gel 0.8% | 15 |
| 10 | Ruboxistaurin gel 0.8% | 20 |
| 12 | Ruboxistaurin gel 0.8% | 30 |
| 2 | Vehicle | 0 |
| 4 | Vehicle | 0 |
| 6 | Vehicle | 0 |
| 8 | Vehicle | 0 |
| 10 | Vehicle | 0 |
| 12 | Vehicle | 0 |
| Percent of Subjects w/an IDGA Value of −2 or Less for Upper Volar Arm | | |
| Baseline | Hydroquinone Cream 4% | 0 |
| Baseline | Ruboxistaurin gel 0.8% | 0 |
| Baseline | Vehicle | 0 |
| 2 | Hydroquinone Cream 4% | 0 |
| 4 | Hydroquinone Cream 4% | 0 |
| 6 | Hydroquinone Cream 4% | 0 |
| 8 | Hydroquinone Cream 4% | 0 |
| 10 | Hydroquinone Cream 4% | 0 |
| 12 | Hydroquinone Cream 4% | 0 |
| 2 | Ruboxistaurin gel 0.8% | 0 |
| 4 | Ruboxistaurin gel 0.8% | 0 |
| 6 | Ruboxistaurin gel 0.8% | 0 |
| 8 | Ruboxistaurin gel 0.8% | 0 |
| 10 | Ruboxistaurin gol 0.8% | 0 |
| 12 | Ruboxistaurin gel 0.8% | 0 |
| 2 | Vehicle | 0 |
| 4 | Vehicle | 0 |
| 6 | Vehicle | 0 |
| 8 | Vehicle | 0 |
| 10 | Vehicle | 0 |
| 12 | Vehicle | 0 |

Figure 4A:
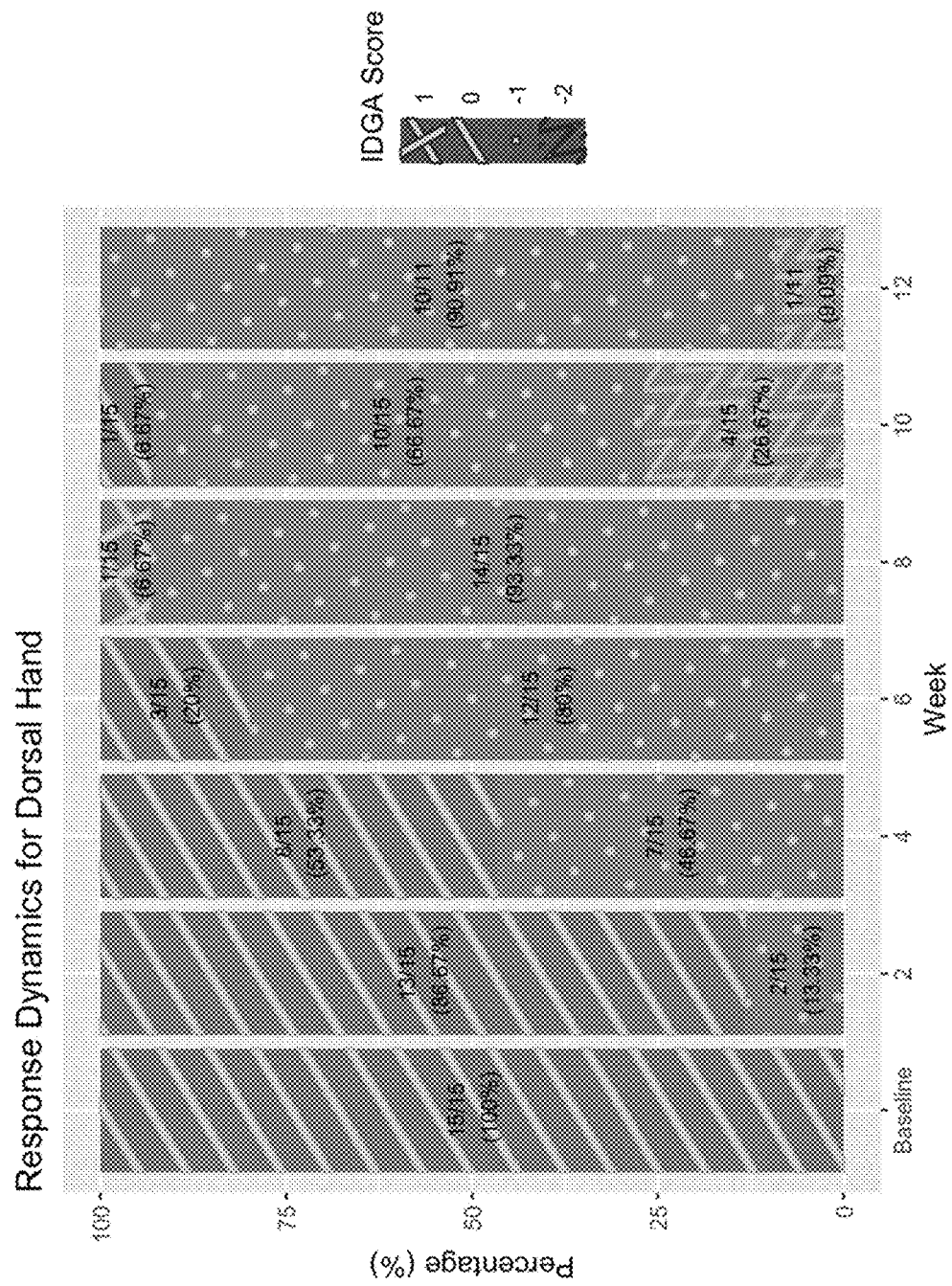
FIG. 4A Percentage of subjects with dorsal hand solar lentigos treated with ruboxistaurin mesylate monohydrate gel 0.8% w/w having IDGA values of −2, −1, 0, or 1.
Figure 4B:
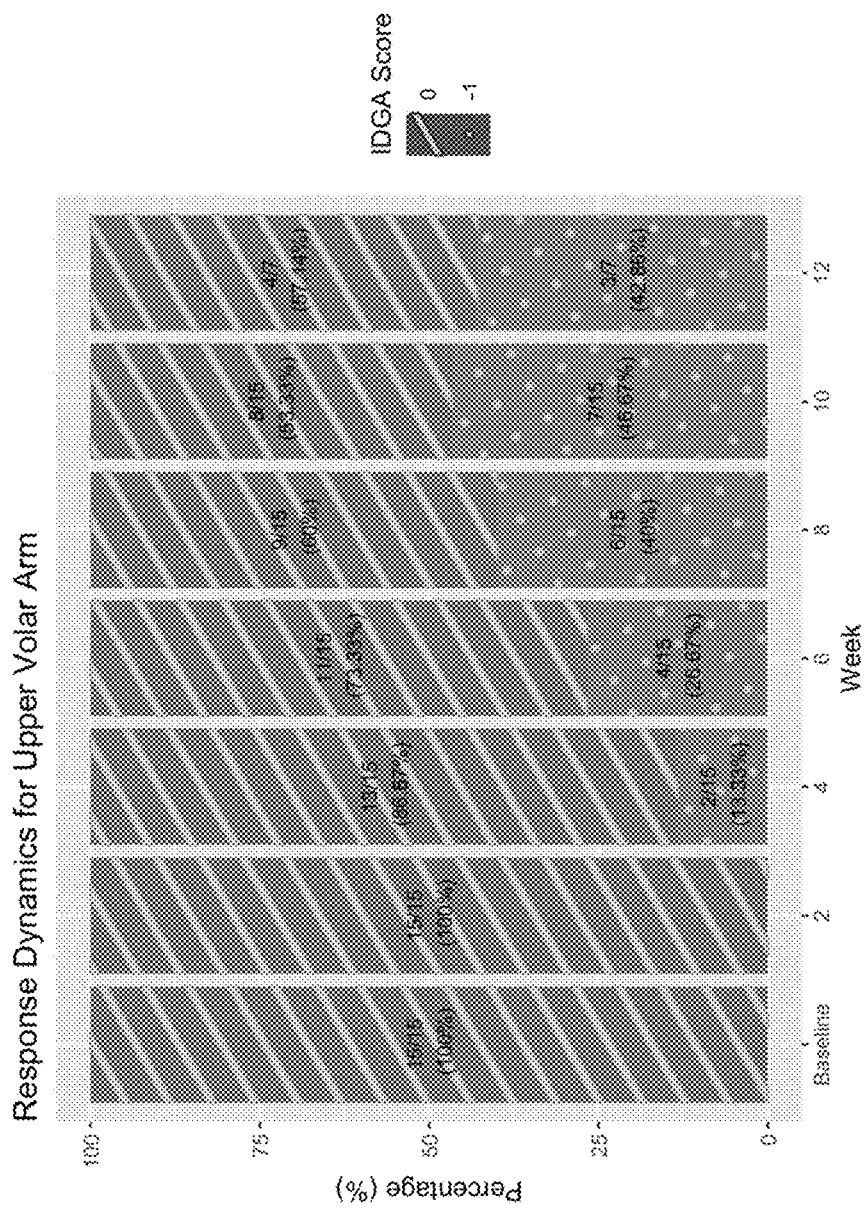
FIG. 4B Percentage of subjects with volar arm treated with ruboxistaurin mesylate monohydrate gel 0.8% w/w having IDGA values of −2, −1, 0, or 1.
Figure 4C:
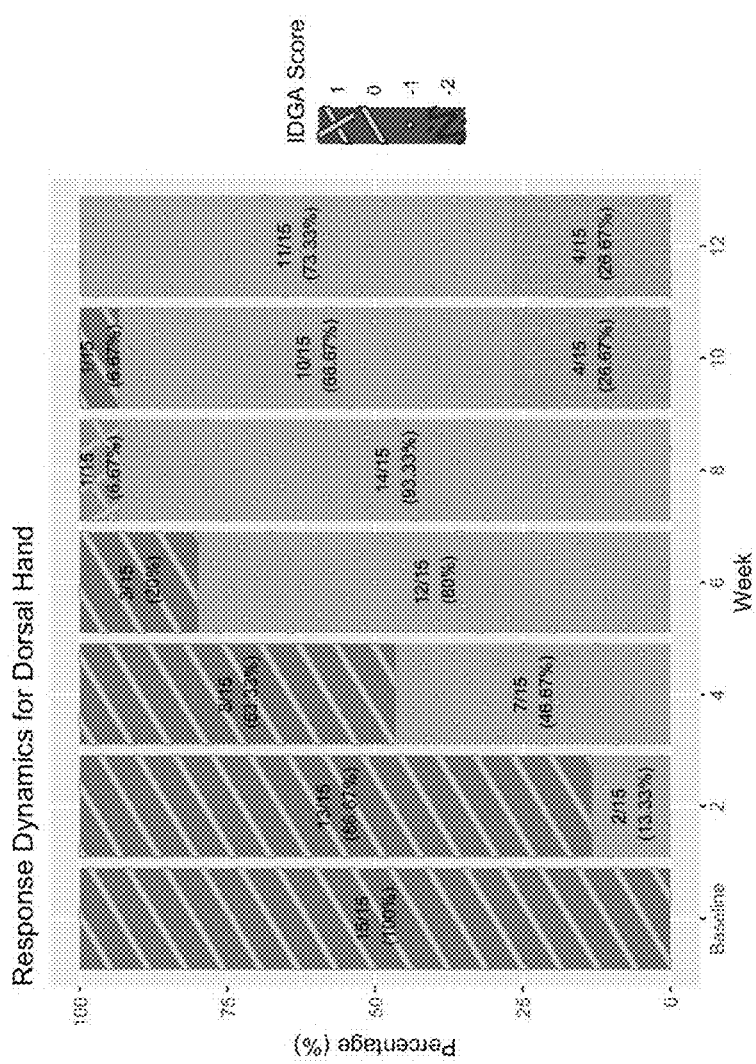
FIG. 4C Percentage of all subjects at all time points with dorsal hand solar lentigos treated with ruboxistaurin mesylate monohydrate gel 0.8% w/w having IDGA values of −2, −1, 0, or 1.
Figure 4D:
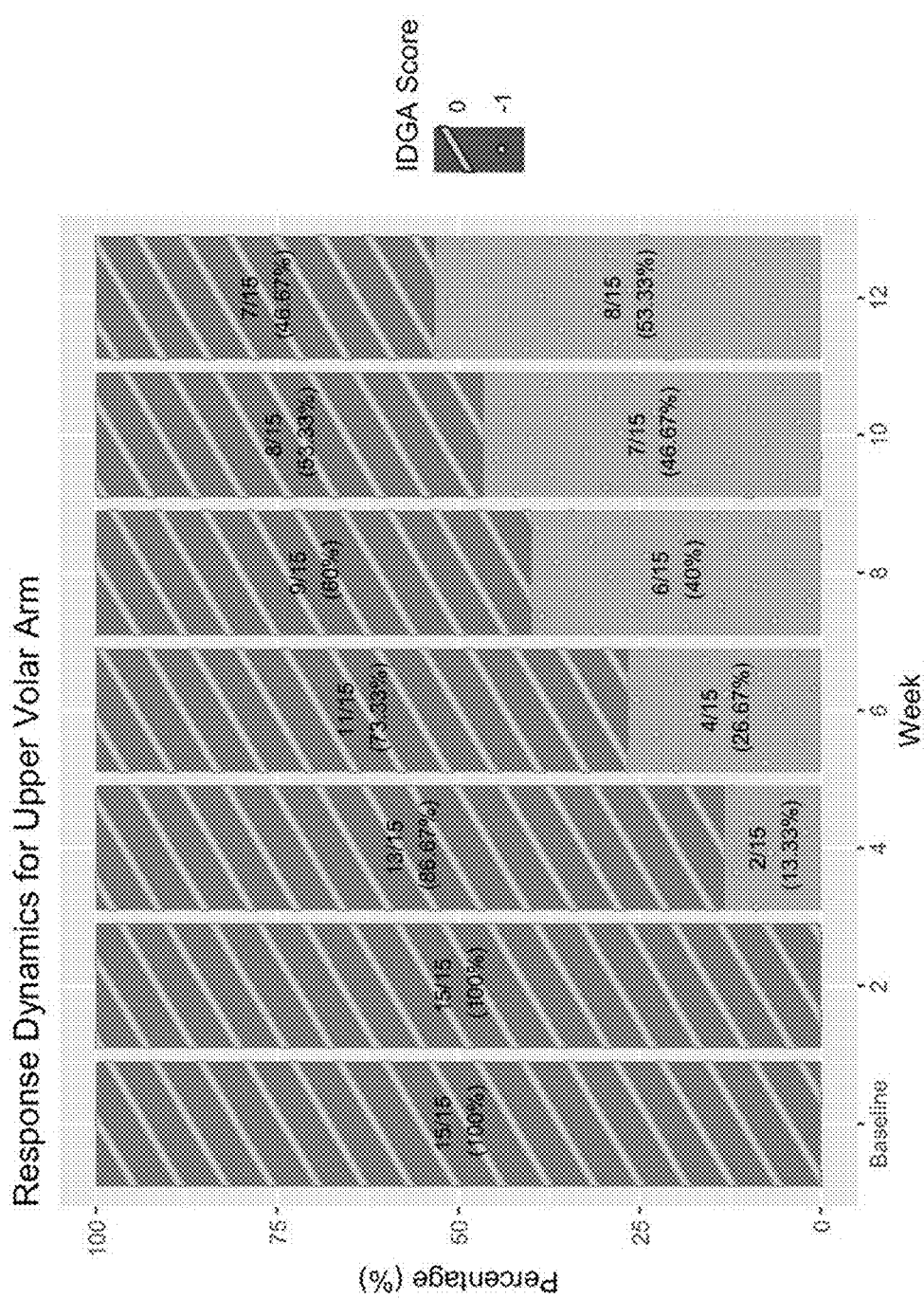
FIG. 4D Percentage of all subjects at all timepoints with volar arm treated with ruboxistaurin mesylate monohydrate gel 0.8% w/w having IDGA values of −2, −1, 0, or 1.

Lentigos:

A cohort of 15 subjects with four lentigos per subject on the dorsal hand were treated with ruboxistaurin gel 0.8%. Analysis of the complete data set from week 12 is pending, data available is presented here. The lentigos were scored using the Investigator Dynamic Global Assessment (IDGA), which compares the relative pigmentation of the treated lentigos to untreated areas/lentigos. In the group with treated lentigos, 100% of subjects with lentigos on their dorsal band treated with ruboxistaurin gel 1.8%. achieved an IDGA of −1 or less (slightly less pigment than the untreated control side) (Table 12: FIG. 4a). Forty six percent (46.474)) of subjects treated on their volar arm with ruboxistaurin gel 0.8%. achieved an IDGA of −1 or less (Table 12; FIG. 4a). Twenty six percent (26.27%) of subjects with lentigos on their dorsal band treated with ruboxistaurin gel 0.8% achieved an IDGA of −2 or less (moderately less pigment than the untreated control side) at week 10 (Table 13: FIG. 4b).

Figure 5A:
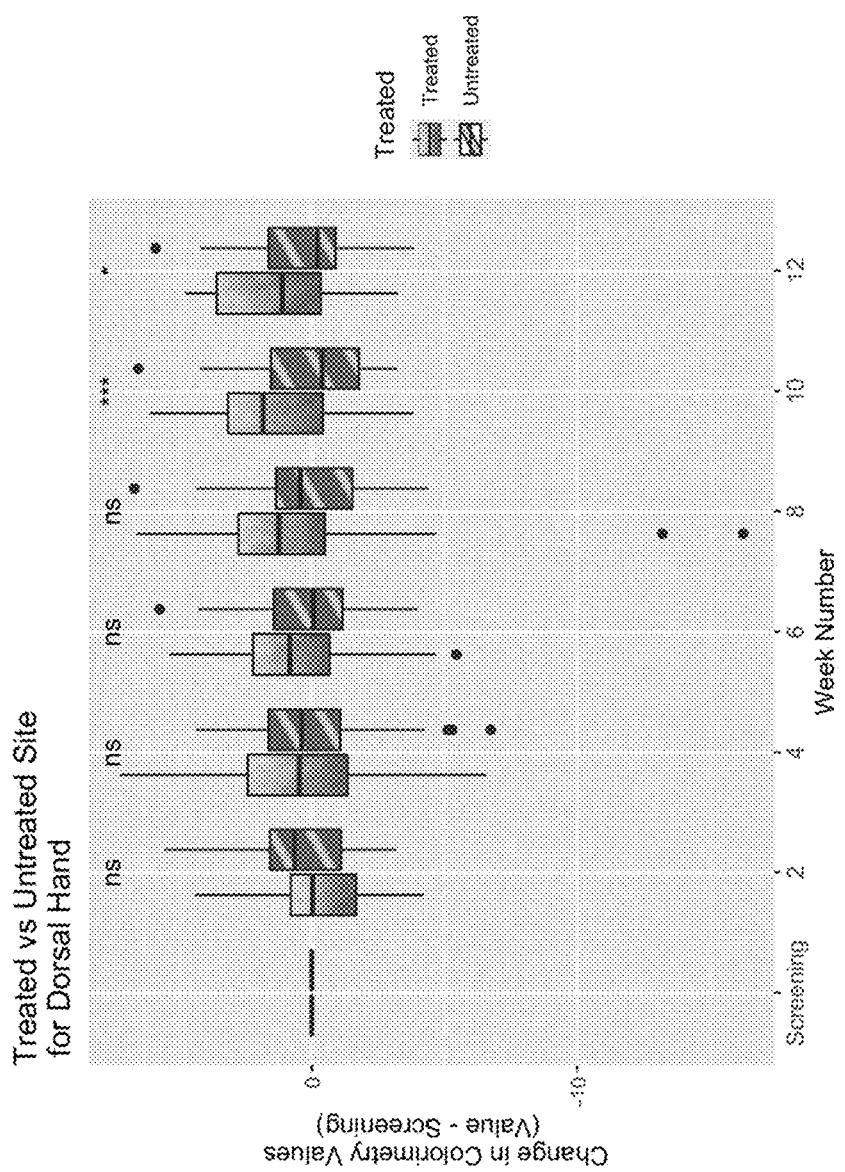
FIG. 5A Change in colorimetry values (as measured by value at visit−screening value) in subjects with lentigos treated on the dorsal hand with ruboxistaurin mesylate monohydrate gel 0.8% w/w compared to untreated sites, a positive value indicates a decrease in pigment (* is $p<0.05$ and *** is $p<0.001$).
Figure 5B:
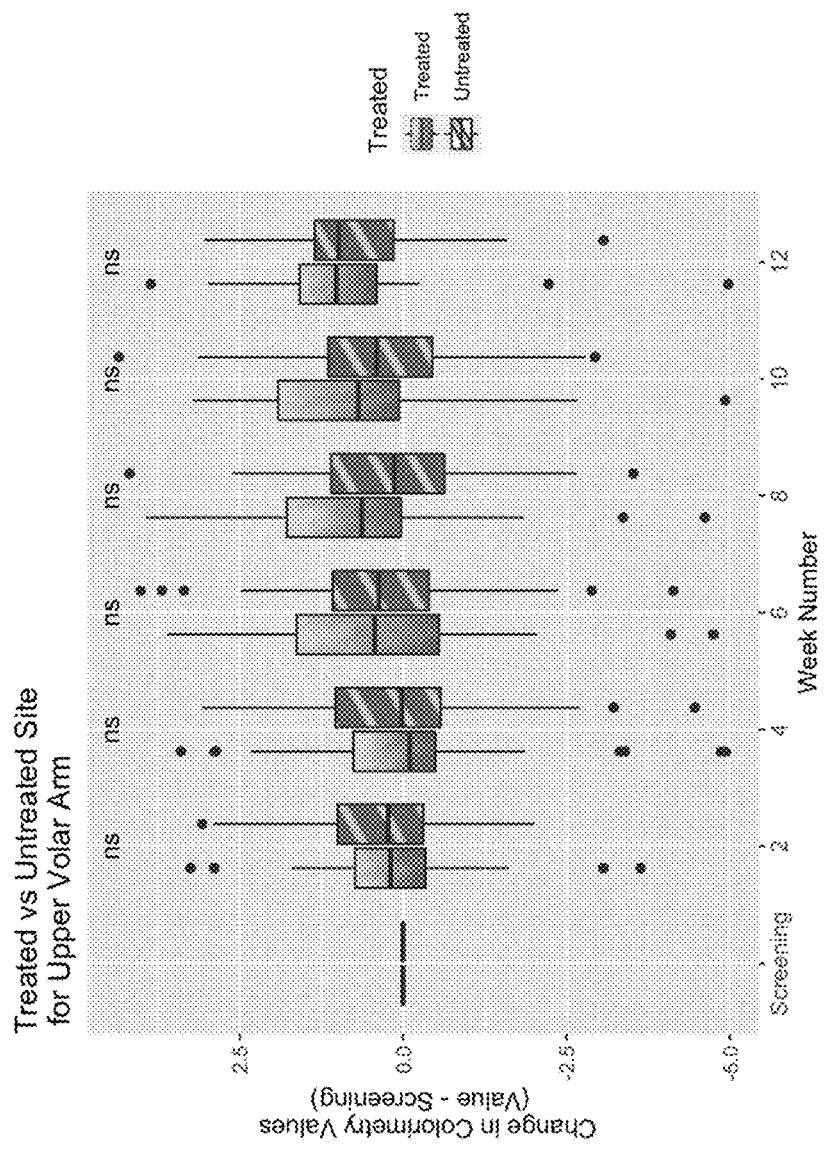
FIG. 5B Change in colorimetry values (as measured by value at visit−screening value) in subjects with lentigos treated on the upper volar arm with ruboxistaurin mesylate monohydrate gel 0.8% w/w compared to untreated sites, a positive value indicates a decrease in pigment.
Figure 5C:
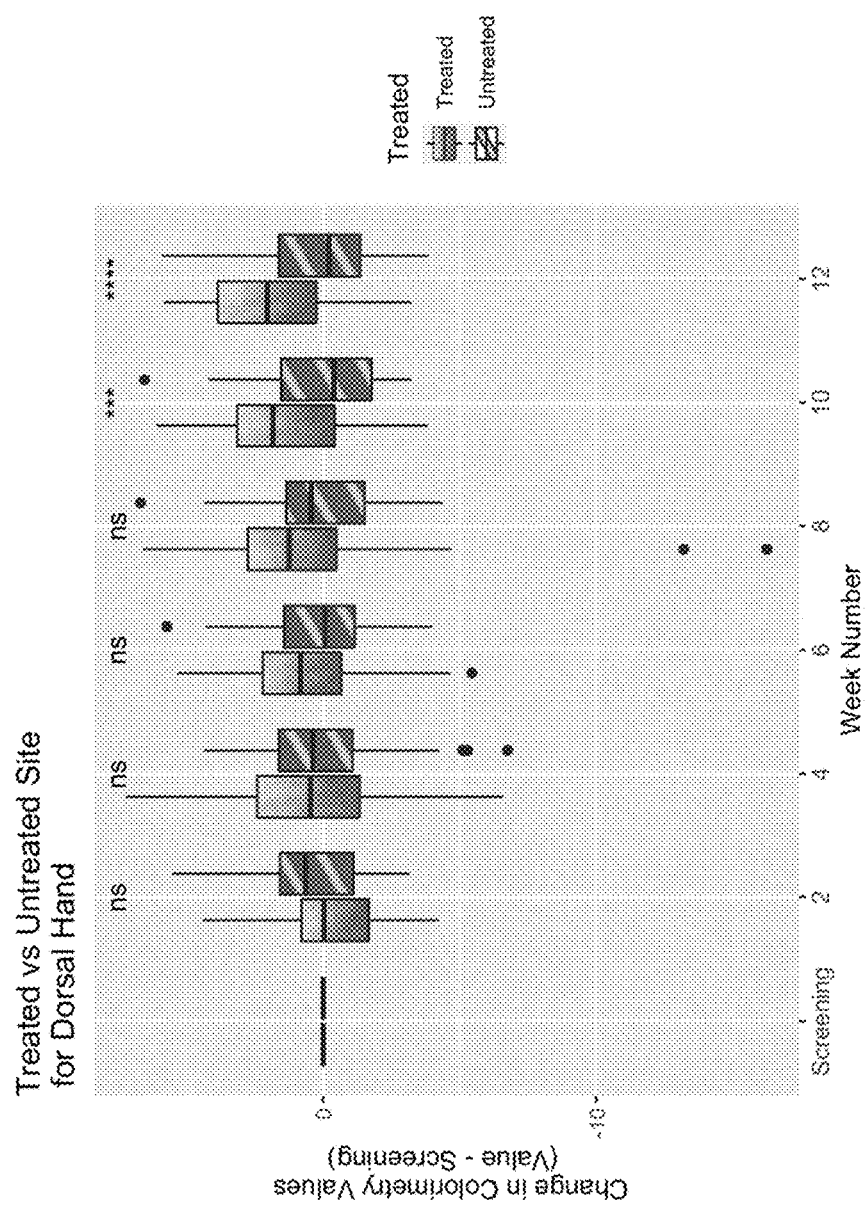
FIG. 5C Change in colorimetry values (as measured by value at visit−screening value) in all subjects at all time points with lentigos treated on the dorsal hand with ruboxistaurin mesylate monohydrate gel 0.8% w/w compared to untreated sites, a positive value indicates a decrease in pigment (* is $p<0.05$ and *** is $p<0.001$).
Figure 5D:
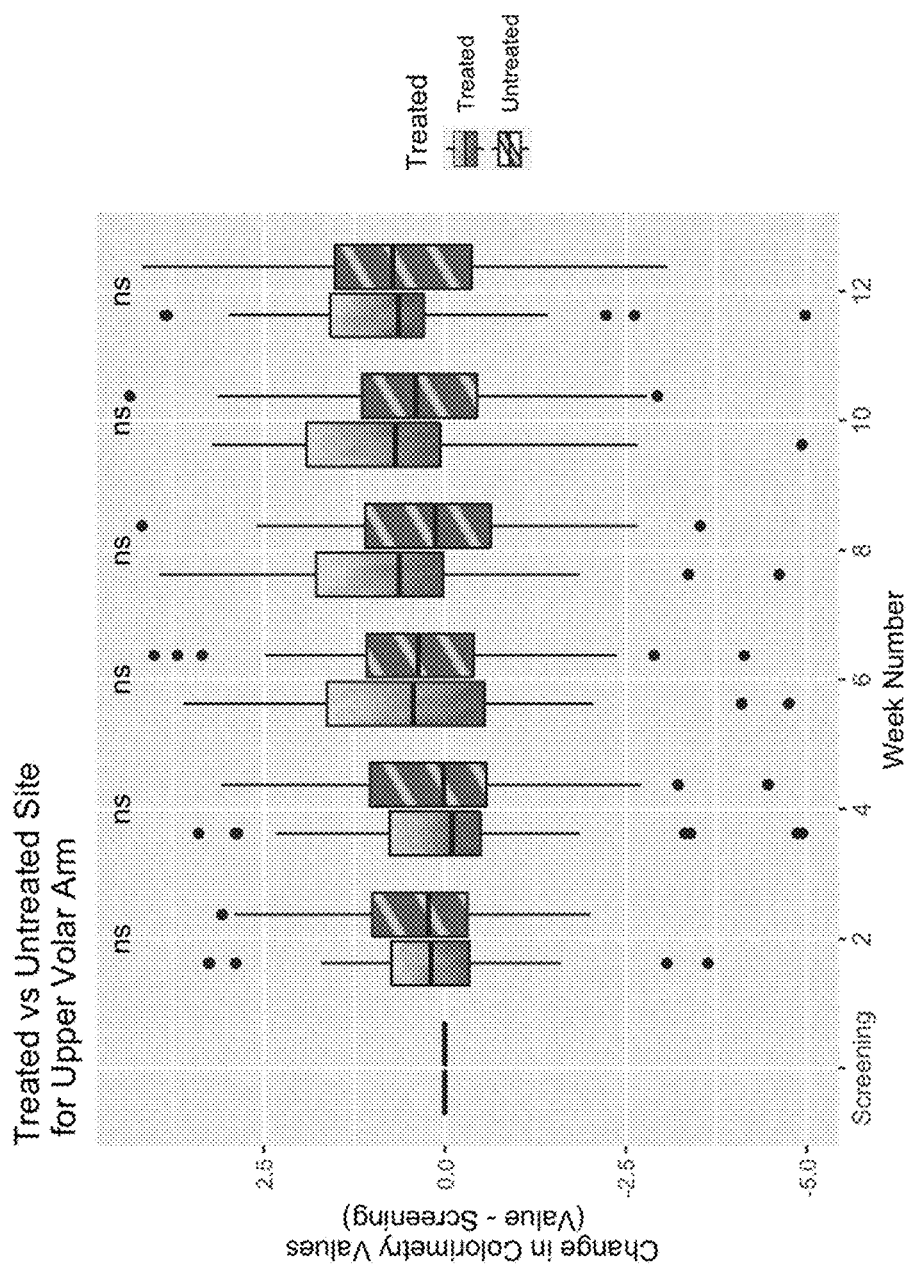
FIG. 5D Change in colorimetry values (as measured by value at visit−screening value) in all subjects at all time points with the upper volar arm treated with ruboxistaurin mesylate monohydrate gel 0.8% w/w compared to untreated sites, a positive value indicates a decrease in pigment.

Colorimetry was also measured for subjects treated with ruboxistaurin gel 0.8%. on the dorsal hand with lentigos or on the volar arm. Subjects with lentigos treated with ruboxistaurin had a significantly greater change in colorimetry, toward a lower colorimetry reading, than the subjects with untreated lentigos (FIG. 5a). A positive change indicates a decrease in pigmentation, No significant difference was seen between treated and untreated areas of the upper volar arm (FIG. 5b).

TABLE 12

Percent of subjects with lentigos treated on the dorsal hand and upper volar arm with 0.8% ruboxistaurin with an IDGA value of −1 or less.

| Week | Treatment | Percent |
|---|---|---|
| Percent of Subjects w/an IDGA Value of −1 or Less for Dorsal Hand | | |
| Baseline | Ruboxistaurin gel 0.8% | 0 |
| 2 | Ruboxistaurin gel 0.8% | 13.33 |
| 4 | Ruboxistaurin gel 0.8% | 46.67 |
| 6 | Ruboxistaurin gel 0.8% | 80 |
| 8 | Ruboxistaurin gel 0.8% | 93.33 |
| 10 | Ruboxistaurin gel 0.8% | 93.33 |
| 12 | Ruboxistaurin gel 0.8% | 100 |
| Percent of Subjects w/an IDGA Value of −1 or Less for Upper Volar Arm | | |
| Baseline | Ruboxistaurin gel 0.8% | 0 |
| 2 | Ruboxistaurin gel 0.8% | 0 |
| 4 | Ruboxistaurin gel 0.8% | 13.33 |

TABLE 12-continued

Percent of subjects with lentigos treated on the dorsal hand and upper volar arm with 0.8% ruboxistaurin with an IDGA value of −1 or less.

| Week | Treatment | Percent |
| --- | --- | --- |
| 6 | Ruboxistaurin gel 0.8% | 26.67 |
| 8 | Ruboxistaurin gel 0.8% | 40 |
| 10 | Ruboxistaurin gel 0.8% | 46.67 |
| 12 | Ruboxistaurin gel 0.8% | 42.86 |

TABLE 13

Percent of subjects with lentigos treated on the dorsal hand and upper volar arm with 0.8% ruboxistaurin with an IDGA value of −2 or less.

| Week | Treatment | Percent |
| --- | --- | --- |
| Percent of Subjects w/an IDGA Value of −2 or Less for Dorsal Hand | | |
| Baseline | Ruboxistaurin gel 0.8% | 0 |
| 2 | Ruboxistaurin gel 0.8% | 0 |
| 4 | Ruboxistaurin gel 0.8% | 0 |
| 6 | Ruboxistaurin gel 0.8% | 0 |
| 8 | Ruboxistaurin gel 0.8% | 0 |
| 10 | Ruboxistaurin gel 0.8% | 26.67 |
| 12 | Ruboxistaurin gel 0.8% | 0 |
| Percent of Subjects w/an IDGA Value of −2 or Less for Upper Volar Arm | | |
| Baseline | Ruboxistaurin gel 0.8% | 0 |
| 2 | Ruboxistaurin gel 0.8% | 0 |
| 4 | Ruboxistaurin gel 0.8% | 0 |
| 6 | Ruboxistaurin gel 0.8% | 0 |
| 8 | Ruboxistaurin gel 0.8% | 0 |
| 10 | Ruboxistaurin gel 0.8% | 0 |
| 12 | Ruboxistaurin gel 0.8% | 0 |

Tolerability:

The treatment was well tolerated with no serious adverse events, no drug-related adverse events, and only occasional and only mild local tolerability reactions. In the Ruboxistaurin gel 0.8% treatment group, no subjects experienced edema, exudation, lichenification, or erosion. There was one report of mild erythema at week 6 and one report of mild desquamation at week 4, but no other reports of these signs. There was one report of mild pruritus at weeks 2, 4, 6, and 8, but there were no reports of pruritus at weeks 10 or 12. Mild pain was the most common symptom in the Ruboxistaurin gel 0.8% group, with 3 reports at week 2, 4 reports at week 4, 5 reports at week 6, 5 reports at week 8, 2 reports at week 10, and 1 report at week 12. These reactions were out of 35 subjects total in the Ruboxistaurin gel 0.8% treatment group.

Example 8: Clinical Trial for Hair Removal

An Open label clinical trial will be conducted to evaluate the safety and efficacy of topically applied ruboxistaurin gel with excipients of formula NA10, NA19, NA18, NA22, or NA28 (referred to as "ruboxistaurin gel") in healthy adult male and female subjects for hair removal.

The study will comprise a 12-week twice daily dosing period. Up to sixty subjects who meet the eligibility criteria will be enrolled in the trial to receive ruboxistaurin gel or vehicle gel.

Each subject will apply daily approximately 0.2 g of the assigned study test article twice daily to an area of the skin containing unwanted hair. The test article will be applied to approximately 100 cm² in each treatment area, about the size of the palm of ones' hand.

Hair loss will be assessed by the investigator and subject using a hair loss measurement scale, quantification and visual assessment. Safety and tolerability of the ruboxistaurin gel 0.8% will be assessed at all visits and included monitoring of adverse events and local tolerability. Tolerability was evaluated through assessment of selected local signs and symptoms (pain/burning/stinging, pruritus, erythema, edema, erosion/ulceration, lichenification (dryness), exudation (scabbing crusting), desquamation (peeling) of skin to which the study test article is applied.

Example 9: Sunscreen and Sunblock Compatibility

A compatibility study is run to determine if combining sunscreens and ruboxistaurin gel results in degradants. As a preliminary study, equal quantities (50:50) of previously manufactured ruboxistaurin gel mm (0.8% w/w) with up to 6 commercial sunscreens are blended. These mixtures are assayed for ruboxistaurin and degradants in triplicate to assess method compatibility. Sunscreens are included as a specificity check. The sunscreens included in the study include Elta MD (UV sport and UV clear), ISDIN Eryfotona, Cetaphil sheer, La-Roche Posay Anthelios, and/or supergoop unseen After mixing Ruboxistaurin gel and sunscreens as above, samples are stored at two different temperatures (ambient and 50° C.) for various time intervals (T=0, 2, 4, 8, 16 and 24 hours), then assayed. Samples are withdrawn and stored at 5° C. and assayed together in a single run after 24 hours. HPLC is used to measure and assess degradants.

Example 8: Additional Research and Development Batches based on Formula NA18, with improved process conditions, 5 kg batches of 0.8% w/w Ruboxistaurin mesylate monohydrate (0.64% w/w Ruboxistaurin free base), 0.1% w/w Ruboxistaurin mesylate monohydrate (0.08% w/w Ruboxistaurin free base) and vehicle were prepared by Dow Development Laboratories and placed at ambient and accelerated (40° C.) conditions. The quantitative and qualitative compositions of each of the lots are in the table below.

TABLE 15

Quantitative and Qualitative Composition of Ruboxistaurin mesylate monohydrate and vehicle Research and Development Batches

| | Ruboxistaurin Strength | | |
| --- | --- | --- | --- |
| Ingredient | 0.80% % w/w | 0.10% % w/w | Vehicle % w/w |
| Transcutol HP | 47.00 | 47.70 | 48.00 |
| BHT | 0.10 | 0.10 | 0.10 |
| BHA | 0.10 | 0.10 | 0.10 |
| SR PEG 400 | 14.00 | 14.00 | 14.00 |
| Propylene Glycol | 20.00 | 20.00 | 20.00 |
| Glycerin | 15.00 | 15.00 | 15.00 |
| Klucel GF | 3.00 | 3.00 | 3.00 |
| Ruboxistaurin MM | 0.80 | 0.01 | |

The stability of each of the lots is presented in the tables below.

TABLE 16

0.8% w/w Ruboxistaurin Mesylate Monohydrate (0.64% w/w Ruboxistaurin Free Base) Research and Development Batch Stability

| Lot #: 2022-082-10 | 0.8% w/w (0.64% w/w Free Base) | Results | | | | | |
|---|---|---|---|---|---|---|---|
| | | 1 months | | 2 months | | 3 months | |
| Test | T0 | Ambient | 40° C. | Ambient | 40° C. | Ambient | 40° C. |
| % Label Claim | 100.2% | 100.4% | 99.7% | 99.3% | 99.2% | 100.2% | 99.2% |
| Total Related Substances | 0.50% | 0.30% | 0.50% | 0.50% | 0.80% | 0.60% | 1.00% |
| Appearance | Dark red, smooth pourable gel | Dark red, smooth pourable gel | Dark red, smooth pourable gel | Dark red, smooth pourable gel | Dark red, smooth pourable gel | Dark red, smooth pourable gel | Dark red, smooth pourable gel |
| pH (neat) | 5.5 | 5.70 | 5.2 | 4.9 | 4.9 | 5.5 | 5.5 |
| Viscosity | 23670 cP | 21420 cP | 20540 cP | 24920 cP | 24920 cP | 23250 cP | 22960 cP |

TABLE 17

0.1% w/w Ruboxistaurin Mesylate Monohydrate (0.08% w/w Ruboxistaurin Free Base) Research and Development Batch Stability

| Lot #: 2022-082-6 | 0.1% w/w (0.08% w/w Free Base) | Results | | | | | |
|---|---|---|---|---|---|---|---|
| | | 1 months | | 2 months | | 3 months | |
| Test | T0 | Ambient | 40° C. | Ambient | 40° C. | Ambient | 40° C. |
| % Label Claim | 101.2% | 100.1% | 100.0% | 99.1% | 99.1% | 100.3% | 99.1% |
| Total Related Substances | 0.6% | 0.6% | 0.90% | 0.70% | 1.2% | 0.9% | 1.4% |
| Appearance | Red, smooth pourable gel | Red, smooth pourable gel | Red, smooth pourable gel | Red, smooth pourable gel | Red, smooth pourable gel | Red, smooth pourable gel | Red, smooth pourable gel |
| pH (neat) | 6.7 | 9.9 | 7.5 | 5.8 | 5.8 | 6.3 | 6.4 |
| Viscosity | 22420 cP | 21330 cP | 20880 cP | 24170 cP | 24080 cP | 22790 cP | 23250 cP |

TABLE 18

Vehicle Research and Development Batch Stability

| Lot #: 2022-082-17 | Vehicle | Results | | | | | |
|---|---|---|---|---|---|---|---|
| | | 1 months | | 2 months | | 3 months | |
| Test | T0 | Ambient | 40° C. | Ambient | 40° C. | Ambient | 40° C. |
| Appearance | Colorless, smooth pourable gel | Colorless, smooth pourable gel | Colorless, smooth pourable gel | Colorless, smooth pourable gel | Colorless, smooth pourable gel | Colorless, smooth pourable gel | Colorless, smooth pourable gel |
| pH (neat) | 8.6 | 9.2 | 9.1 | 8.2 | 7.7 | 7.8 | 7.7 |
| Viscosity | 20500 cP | 27790 cP | 17130 cP | 27040 cP | 20670 cP | 20540 cP | 20040 cP |

After 3 months of storage at ambient (18-25° C.) and accelerated (40° C.) temperature conditions, the research and development lots remained within specification from the time of lot release to the most recent timepoint and overall reproduce the same stability trends as observed with the clinical lots. Additionally, the 3-month time point at the accelerated (40° C.) conditions reproduces that same trend and success in the demonstration of stability for this drug product formulation as observed with the lots used in the clinical studies. Stability testing at ambient (18-25° C.) and accelerated (40° C.) temperature conditions is ongoing.

Example 9: 25 kg Scale Up Research and Development Batches based on Formula NA18A 25 kg batch of 0.1% w/w Ruboxistaurin mesylate monohydrate (0.08 w/w Ruboxistaurin free base) was prepared by Dow Development Laboratories. The quantitative and qualitative compositions of the lot is in the table below

TABLE 19

| Quantitative and Qualitative Composition of a 25 kg Scale Up Batch of 0.1% w/w Ruboxistaurin mesylate monohydrate Research and Development BatchLot #: 2022-082-47 Ingredient | Ruboxistaurin 0.1% w/w % w/w |
|---|---|
| Transcutol HP | 47.68 |
| BHT | 0.10 |
| BHA | 0.10 |
| SR PEG 400 | 14.00 |
| Propylene Glycol | 20.00 |
| Glycerin | 15.00 |
| Klucel GF | 3.00 |
| Ruboxistaurin MM | 0.10 |

During manufacturing of the 25 kg Research and Development Scale Up lot, in process sampling at different locations (top, middle and bottom) in replicate from the manufacturing vessel were within the label claim specification of 90-110%. Results are presented in the table below.

TABLE 20

25 kg Research and Development In Process Label Claim Test Results

| | | | 0.1% w/w (0.08% w/w Free Base) | |
|---|---|---|---|---|
| 25 kg Batch | | | | In Process |
| Test | Specification | Location | Results | Test Results |
| % Label Claim | 90-110% | Top | 95.8%, 95.1% | 95.1% |
| | | Middle | 95.1%, 94.9% | |
| | | Bottom | 95.3%, 94.4% | |

Full testing and stability testing at ambient 18-25° C. and accelerated 40° C. temperature conditions are ongoing.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A topical composition comprising:
ruboxistaurin or a salt thereof;
2-(2-ethoxyethoxy)ethanol;
polyethylene glycol (PEG);
propylene glycol;
glycerin;
hydroxypropyl cellulose; and
one or more antioxidants,
wherein (i) the 2-(2-ethoxyethoxy)ethanol is 40% to 50% of the topical composition by weight; (ii) the polyethylene glycol is 10% to 20% of the topical composition by weight; (iii) the propylene glycol is 8% to 30% of the topical composition by weight; and (iv) the ruboxistaurin or a salt thereof is 0.01% to 1% of the topical composition by weight; and wherein average molecular weight of the polyethylene glycol is from 200 to 900 Daltons.

2. The topical composition of claim 1, wherein the ruboxistaurin or a salt thereof is about 0.1%, or about 0.80% of the topical composition by weight.

3. The topical composition of claim 1, wherein:
(i) the 2-(2-ethoxyethoxy)ethanol is about 43% to about 49%, about 47% to about 49%, or about 47% to about 48% of the topical composition by weight;
(ii) the polyethylene glycol is about 13% to about 15%, or about 13% to about 14% of the topical composition by weight;
(iii) the propylene glycol is about 9% to about 22%, about 18% to about 22%, about 19% to about 21% or about 19% to about 20% of the topical composition by weight;
(iv) the glycerin is about 10% to about 20% or about 15% of the topical composition by weight;
(v) the hydroxypropyl cellulose is about 1% to about 3% of the topical composition by weight;
(vi) the one or more antioxidants is about 0.01% to about 1.0% of the topical composition by weight; or
(vii) two or more selected from (i) to (vi).

4. The topical composition of claim 1, wherein the ruboxistaurin or a salt thereof is ruboxistaurin mesylate monohydrate.

5. The topical composition of claim 1, wherein the ruboxistaurin or a salt thereof comprises ruboxistaurin hydrochloride, ruboxistaurin sulfate, ruboxistaurin tartrate, ruboxistaurin succinate, ruboxistaurin acetate, or ruboxistaurin phosphate.

6. The topical composition of claim 1, wherein the ruboxistaurin or a salt thereof is present in the topical composition in an amount of about 0.001 mg to about 10 g.

7. The topical composition of claim 1, further comprising Cocoylcaprylocaprate, Decyl oleate, Dimethyl isosorbide, Glyceryl monooleate, Isopropyl myristate, medium chain triglyceride (MCT), Octyldodecanol, Oleyl alcohol, Oleyl oleate, Polyoxyethylene alkyl ether, Polyoxyethylene stearate, Propylene glycol monolaurate, Lecithin, cyclodextrin, docusate sodium, glyceryl monostearate, hydrogenated vegetable oil, cottonseed oil, palm kernel oil, N-methyl-2-pyrrolidone, poloxamer, polysorbate, PEG castor oil derivative, polyoxylglyceride, sodium lauryl sulfate, sucrose ester, ethanol, propanol, isopropanol, n-butanol, isobutanol, 2-butanol, tert-butanol, hydroxypropyl cellulose, hydroxyethyl cellulose, carbopol, carbomer, or carboxymethyl cellulose, or a combination of two or more thereof.

8. The topical composition of claim 1, wherein the hydroxypropyl cellulose is HPC GF, HPC CF, HPC MF, Klucel EF, Klucel LF, Klucel JF, or HPC HF, or a combination of two or more thereof.

9. The topical composition of claim 1, wherein the one or more antioxidants is about 0.01% to 0.5% by weight of the topical composition.

10. The topical composition of claim 1, wherein the topical composition is formulated as a gel.

11. A method of treating a skin discoloration disorder, comprising administering a topical composition to a subject in need thereof, wherein the topical composition comprises:
ruboxistaurin or a salt thereof;
2-(2-ethoxyethoxy)ethanol;
polyethylene glycol (PEG);
propylene glycol;
glycerin;
hydroxypropyl cellulose; and
one or more antioxidants, wherein (i) the 2-(2-ethoxyethoxy)ethanol is 40% to 50% of the topical composition by weight; (ii) the polyethylene glycol is 10% to 20% of the topical composition by weight; (iii) the propylene glycol is 8% to 30% of the topical composition by weight; and (iv) the ruboxistaurin or a salt thereof is 0.01% to 1% of the topical composition by weight; and wherein average molecular weight of the polyethylene glycol is from 200 to 900 Daltons.

12. The method of claim 11, wherein the skin discoloration disorder is a hyperpigmentation disorder.

13. The method of claim 11, wherein the skin discoloration disorder is a melasma.

14. The method of claim 11, wherein the ruboxistaurin or a salt thereof is about 0.1%, or about 0.80% of the topical composition by weight.

15. The method of claim 11, wherein:
 (i) the 2-(2-ethoxyethoxy)ethanol is about 43% to about 49%, about 47% to about 49%, or about 47% to about 48% of the topical composition by weight;
 (ii) the polyethylene glycol is about 13% to about 15%, or about 13% to about 14% of the topical composition by weight;
 (iii) the propylene glycol is about 9% to about 22%, about 18% to about 22%, about 19% to about 21%, or about 19% to about 20% of the topical composition by weight;
 (iv) the glycerin is about 10% to about 20% or about 15% of the topical composition by weight;
 (v) the hydroxypropyl cellulose is about 1% to about 3% of the topical composition by weight;
 (vi) the one or more antioxidants is about 0.01% to about 1.0% of the topical composition by weight; or
 (vii) two or more selected from (i) to (vi).

16. The method of claim 11, wherein the ruboxistaurin or a salt thereof comprises ruboxistaurin mesylate monohydrate, ruboxistaurin free base, ruboxistaurin hydrochloride, ruboxistaurin sulfate, ruboxistaurin tartrate, ruboxistaurin succinate, ruboxistaurin acetate, or ruboxistaurin phosphate.

17. The method of claim 11, wherein the ruboxistaurin or a salt thereof is present in the topical composition in an amount of about 0.001 mg to about 10 g.

18. The method of claim 11, wherein the hydroxypropyl cellulose is HPC GF, HPC CF, HPC MF, Klucel EF, Klucel LF, Klucel JF, or HPC HF, or a combination of two or more thereof.

19. The method of claim 11, wherein the one or more antioxidants comprises about 0.05% to 0.5% by weight of the topical composition.

20. The method of claim 11, wherein the topical composition is formulated as a gel.

21. A topical composition comprising:
ruboxistaurin mesylate monohydrate;
2-(2-ethoxyethoxy)ethanol;
polyethylene glycol (PEG); and
propylene glycol;
 wherein (i) the 2-(2-ethoxyethoxy)ethanol is 40% to 50% of the topical composition by weight; (ii) the polyethylene glycol is 10% to 20% of the topical composition by weight; (iii) the propylene glycol is 8% to 30% of the topical composition by weight, and (iv) the ruboxistaurin mesylate monohydrate is 0.01% to 1% of the topical composition by weight; and
 wherein average molecular weight of the polyethylene glycol is from 200 to 900 Daltons.

\* \* \* \* \*